(12) United States Patent
Chang

(10) Patent No.: US 12,188,042 B2
(45) Date of Patent: *Jan. 7, 2025

(54) ELECTROPORATION DEVICES AND METHODS OF CELL TRANSFECTION

(71) Applicant: NanoCav, LLC, Culver City, CA (US)

(72) Inventor: Chih-Wei Chang, Los Angeles, CA (US)

(73) Assignee: NanoCav, LLC, Culver City, CA (US)

( * ) Notice: Subject to any disclaimer, the term of this patent is extended or adjusted under 35 U.S.C. 154(b) by 960 days.

This patent is subject to a terminal disclaimer.

(21) Appl. No.: 16/923,606

(22) Filed: Jul. 8, 2020

(65) Prior Publication Data

US 2020/0340014 A1    Oct. 29, 2020

Related U.S. Application Data

(63) Continuation-in-part of application No. 16/506,190, filed on Jul. 9, 2019, now Pat. No. 11,377,652.

(60) Provisional application No. 62/695,436, filed on Jul. 9, 2018.

(51) Int. Cl.
| | | |
|---|---|---|
| A61K 48/00 | (2006.01) | |
| A61N 1/18 | (2006.01) | |
| B01L 3/00 | (2006.01) | |
| C12M 1/42 | (2006.01) | |
| C12M 3/06 | (2006.01) | |
| C12N 15/11 | (2006.01) | |
| C12N 15/87 | (2006.01) | |

(52) U.S. Cl.
CPC ........ *C12N 15/87* (2013.01); *B01L 3/502715* (2013.01); *C12M 23/16* (2013.01); *C12M 35/02* (2013.01); *B01L 2300/06* (2013.01); *B01L 2300/0645* (2013.01); *B01L 2300/12* (2013.01)

(58) Field of Classification Search
None
See application file for complete search history.

(56) References Cited

U.S. PATENT DOCUMENTS

| | | | |
|---|---|---|---|
| 6,074,605 A | 6/2000 | Meserol et al. | |
| 6,969,604 B1 | 11/2005 | Yakovenko | |
| 11,278,606 B2 * | 3/2022 | Soon-Shiong | ..... A61K 39/0011 |
| 11,377,652 B2 * | 7/2022 | Chang | ..... A61N 1/327 |
| 2004/0197883 A1 | 10/2004 | Dzekunov et al. | |
| 2005/0118705 A1 | 6/2005 | Rabbitt et al. | |
| 2009/0053813 A1 | 2/2009 | Evans | |
| 2014/0004501 A1 | 1/2014 | Talebpour et al. | |
| 2017/0037357 A1 | 2/2017 | Cattaruzzi et al. | |
| 2017/0283761 A1 | 10/2017 | Corso | |
| 2019/0136224 A1 | 5/2019 | Garcia Dominguez et al. | |
| 2020/0017847 A1 | 1/2020 | Chang | |
| 2020/0340014 A1 | 10/2020 | Chang | |

FOREIGN PATENT DOCUMENTS

| | | |
|---|---|---|
| CN | 1265144 A | 8/2000 |
| CN | 102656260 A | 9/2012 |
| CN | 101928666 B | 4/2013 |
| CN | 103451097 A | 12/2013 |
| CN | 106995783 A | 8/2017 |
| CN | 208250332 U | 12/2018 |
| JP | S62265982 | 11/1987 |
| JP | 2007532093 A | 11/2007 |
| WO | 2006112870 A1 | 10/2006 |
| WO | 2011089953 A1 | 7/2011 |
| WO | 2020014264 A1 | 1/2020 |
| WO | 2021007315 A1 | 1/2021 |

OTHER PUBLICATIONS

Ding et al., "High-throught neclear delivery and repid expression of DNA via mechanical and electrical cell-membrane disruption," Nature biomedical engineering, 1(39): 1-7 (2017).

Selmeczi et al., "Efficient large volume electroporation of dendritic cells through micrometer scale manipulation of flow in a disposable polymer chip," Biomed Microdevices, 13: 383-392 (2011).

Choi et al., "A high throughput microeletroporatin device to introduce a chimeric antigen receptor to redirect the specificity of human T cells," Biomed Microdevices, 12: 855-863 (2010).

Andresen et al., "Injection molded chips with integrated conducting polymer electrodes for electroporation of cells," Journal of Micromechanics and Microengineering, 20: 1-9 (2010).

Selmeczi et al., "Large scale mRNA Transfection of Dendritic Cells by Electroporation in Ccontinuous Flow Systems," Methods in Molecular Biology, 1428 (Chapter 10) : 151-161 (2016).

Zhao, D., et al., "A Flow-Through Cell Electroporation Device for Rapidly and Efficiently Transfecting Massive Amounts of Cells in vitro and ex vivo , " Scientific Reports, 6: 1-9 (2016).

Jiang, W., et al., "Functional characterization of interleukin-15 gene transduction into the human natural killer cell line NKL," Cytotherapy, 10(3): 265-274 (2008).

Boissel, L., et al., "Transfection with mRNA for CD19 specific chimeric antigen receptor restores NK cell mediated killing of CLL cells," Leuk Res., 33(9): 1255-1259 (2009).

Moffett, H.F., et al., "Hit-and-run programming of therapeutic cytoreagents using mRNA nanocarriers," Nature Communications, 8(389): 1-13 (2017).

(Continued)

*Primary Examiner* — Maria Marvich
(74) *Attorney, Agent, or Firm* — Harness Dickey & Pierce P.L.C.

(57) ABSTRACT

Systems and methods are provided for transfecting cells, such as mammalian cells and nonmammalian cells, using an electroporation apparatus having an electroporation chamber including a first electrode, a second electrode and a path defined in the electroporation chamber. The electroporation apparatus includes a first input allowing passage of cells and cargo into the electroporation chamber and a first output allowing passage of electroporated cells from the electroporation chamber.

38 Claims, 44 Drawing Sheets

(15 of 44 Drawing Sheet(s) Filed in Color)

(56) References Cited

OTHER PUBLICATIONS

Young, J.L. & Dean, D.A., "Electroporation-Mediated Gene Delivery," Adv. Genet, 89: 49-88 (2015).

Li, S., "Electroporation Protocols: Preclinical and clinical gene medicine," Shulin Li (Ed.), Methods in Molecular Biology, 423: 1-511 (2008).

MaxCyte, "MaxCyte VLX® Large-Scale Transfection System," (2017).

MaxCyte, "ExPERT GTx," (2020).

MaxCyte, "ExPERT STx," (2020).

Wei, Z., et al., "A Laminar Flow Electroporation System for Efficient DNA and siRNA Delivery," Analytical Chemistry, 83: 5881-5887 (2011).

Office Action from Chinese Application No. 202080003926.x dated Nov. 2, 2023.

Office Action from German Application No. 112019003498.7 dated Nov. 18, 2023.

Office Action from U.S. Appl. No. 17/380,799 dated Mar. 28, 2024.

\* cited by examiner

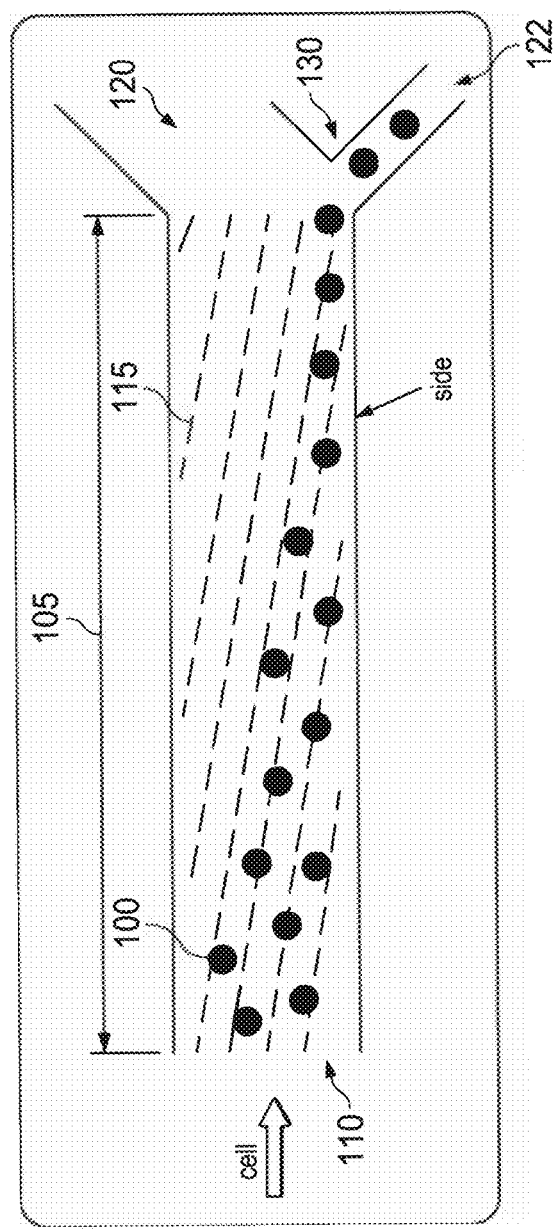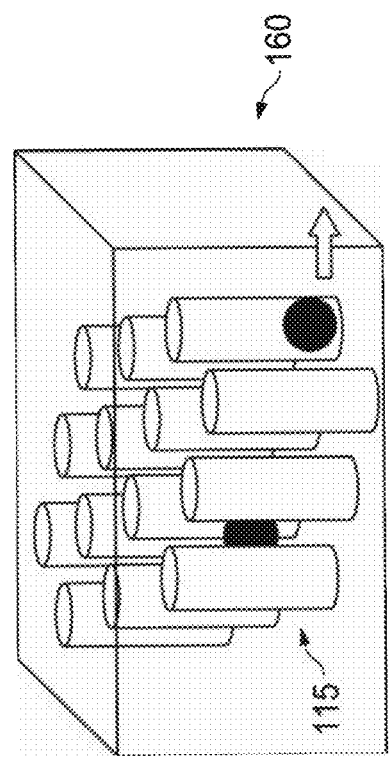
FIG. 3K
FIG. 3L

| | Channel Offset Electroporation Device | Prior Art |
|---|---|---|
| Configuration | Offset | Regular |
| Buffer | Cw100: 110mS/m, 128 mOSM/L | BTX T media: 8mS/m, 270mOSM/L |
| Cell line, density | NK cell ($1.7 \times 10^7$ cells/ml) EC.7 ($4 \times 10^7$ cells/ml) | Dendritic cell ($1 \times 10^7$ cells/ml) |
| Average flow rate | 0.44mL/min | 0.45mL/min |
| Pulse shape | Exponential discharging waveform | Square waveform |
| Number of pulses | 4 | 1 |
| Flow scheme | Stepping (see below) | Continuous |

FIG. 4

| | stimulus | | | | | | | cells | | | cargo vol | cargo % | final cell % | Pump | | | | |
|---|---|---|---|---|---|---|---|---|---|---|---|---|---|---|---|---|---|---|
| | E | V actual | V set | Cp | Rp | T | t | cell# | volume | cell % | | | | step volume | Q step | pause | pulse# | Qave |
| CTL | 0 | 0 | 0 | 0 | 0 | 0 | 0 | 16m | 0.4ml | 40m/ml | 0 | 0ug/ml | 40m/ml | | | | 0 | |
| AD5gfp | 1kv | 30v | ~36v | 10uF | 200 | 0.4s | ~1ms | 16m | 0.4ml | 40m/ml | 50ug/50ul | 111ug/ml | 35m/ml | 5ul | 25ul/s | 0.5s | 7p | 428ul/min |
| AD5gfp | 1kv | 30v | | 10uF | 200 | 0.4s | ~1ms | 16m | 0.4ml | 40m/ml | 100ug/100ul | 200ug/ml | 32m/ml | 5ul | 25ul/s | 0.5s | 7p | 428ul/min |
| AD5gfp | 1kv | 30v | | 10uF | 200 | 0.4s | ~1ms | 16m | 0.4ml | 40m/ml | 150ug/150ul | 272ug/ml | 29m/ml | 5ul | 25ul/s | 0.5s | 7p | 428ul/min |

(was 4p)

6 days post haNK: GFP mRNA
0.127 billion cells/min
Viability: >90%
*Efficiency: >95%*

CHO: GFP Pmax DNA
15 million cells/min
Viability: >50%
*Efficiency: >90%*

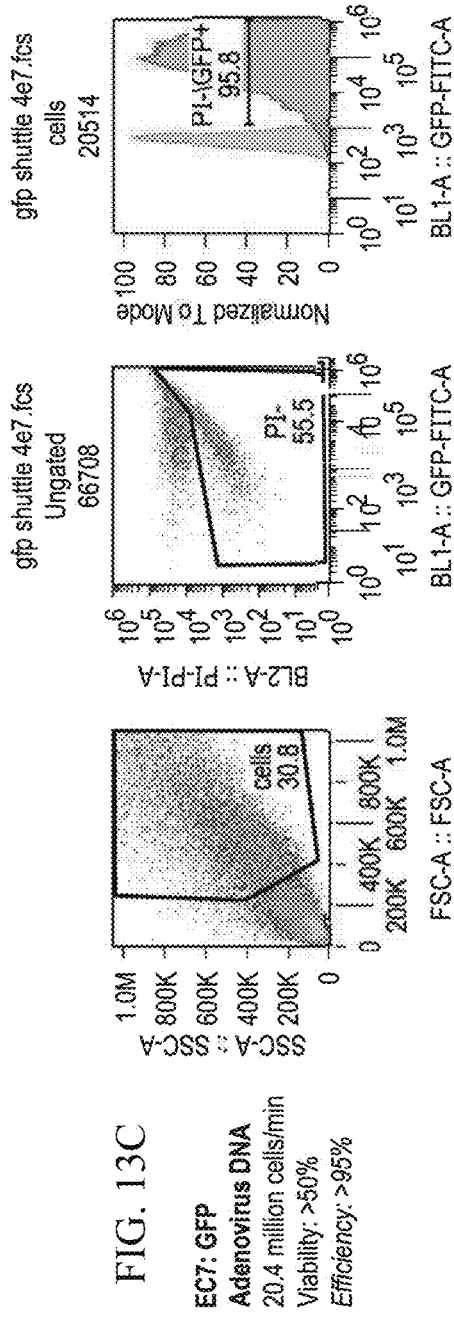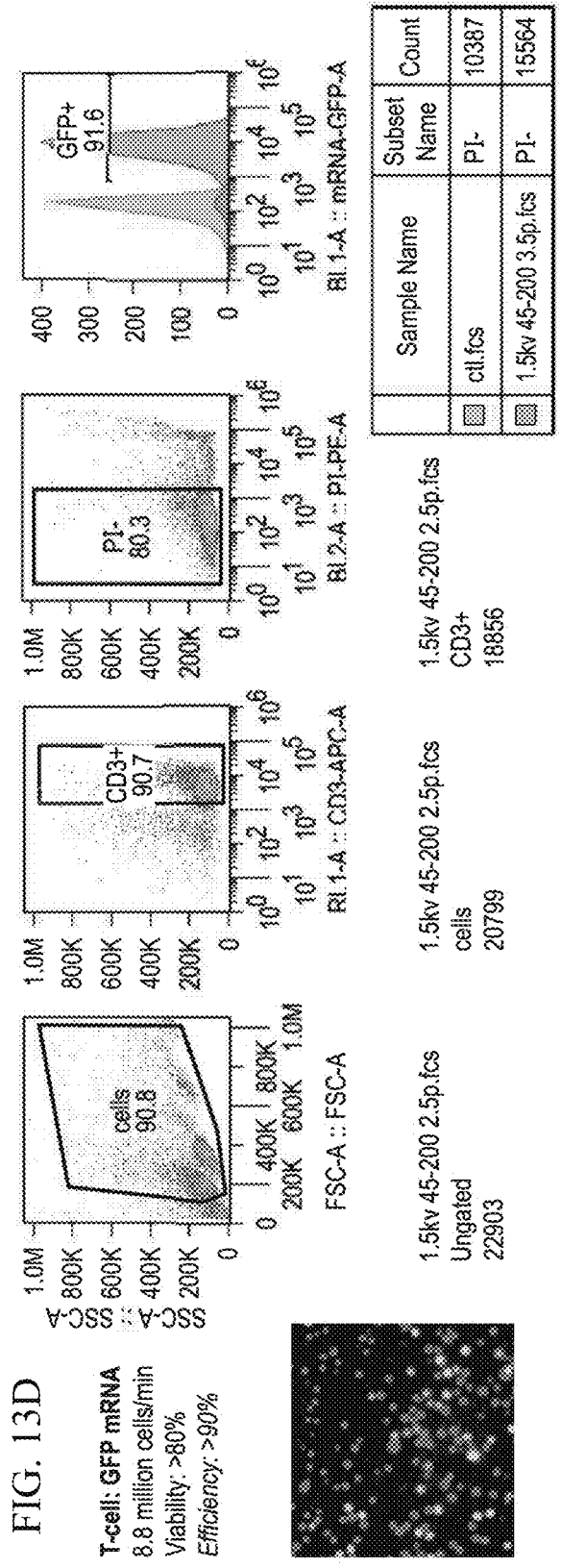
FIG. 13C
EC7: GFP
Adenovirus DNA
20.4 million cells/min
Viability: >50%
Efficiency: >95%
FIG. 13D
T-cell: GFP mRNA
8.8 million cells/min
Viability: >80%
Efficiency: >90%

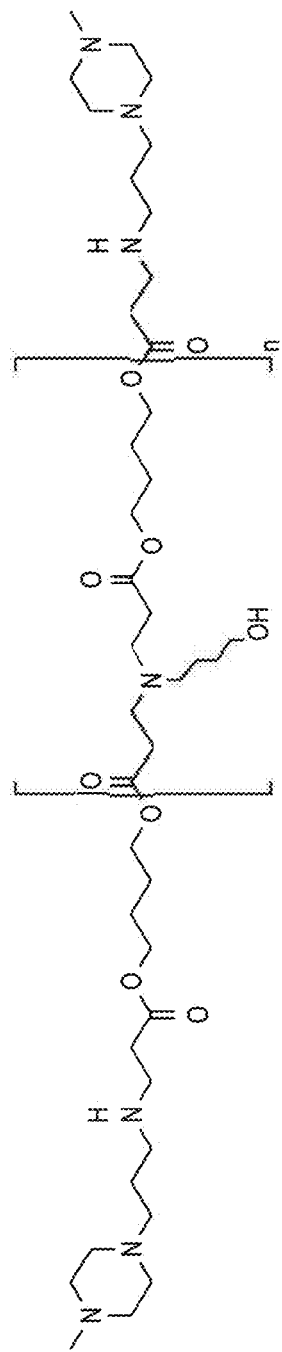
FIG. 14A
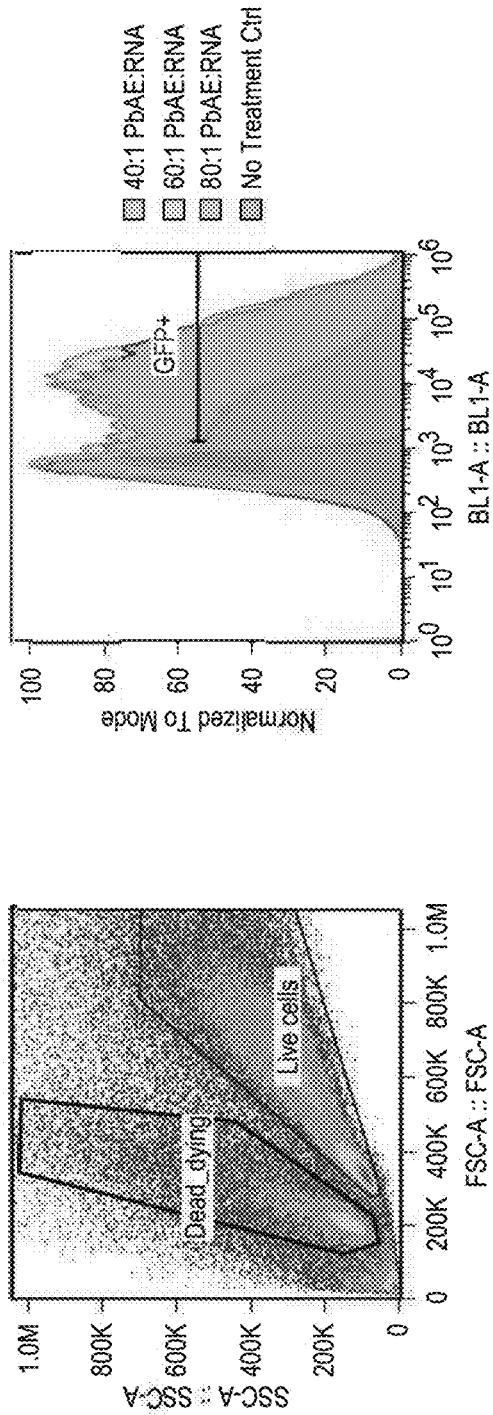
FIG. 14B
FIG. 14C

ELECTROPORATION DEVICES AND METHODS OF CELL TRANSFECTION

CROSS REFERENCE TO RELATED APPLICATIONS

This application is a continuation-in-part of U.S. patent application Ser. No. 16/506,190 filed on 9 Jul. 2019, which claims the benefit of U.S. Provisional Patent Application Ser. No. 62/695,436 filed on 9 Jul. 2018. The entire disclosures of each of the above recited applications are incorporated herein by reference.

FIELD OF THE INVENTION

The field of the invention relates to transfection systems and methods, and in particular, electroporation systems and methods.

BACKGROUND OF THE INVENTION

The background description includes information that may be useful in understanding the methods and techniques presented herein. It is not an admission that any of the information provided herein is prior art or relevant to the subject matter presented herein, or that any publication specifically or implicitly referenced is prior art.

Transfection may be used to introduce nucleic acids into cells to produce genetically modified cells. Various physical, chemical and viral methods exist for transfecting cells, including optoperforation, polymer based methods utilizing calcium phosphate, microinjection, electroporation, viral transduction, and lipid mediated methods (e.g., using liposome-DNA complexes).

Electroporation involves applying a controlled direct current (DC) electrical pulse to a cell for a relatively short duration of time. The electrical pulse is thought to induce a transmembrane potential that causes a reversible breakdown of the ordered structure of a cell membrane, leading to the formation of pores in the membrane. Molecules of interest can then enter the cell through the pores until the pores close, typically within milliseconds to seconds. Pore formation can be controlled by adjusting various parameters, especially gap width (e.g., distance between parallel electrode plates), electrical pulse wave form, electric field strength, temperature, and electrical pulse length.

Electroporation is commonly used at the laboratory scale (e.g., using small cuvettes with a capacity of about 0.5 mL), but such laboratory based techniques are not suitable for large scale, clinical grade production, due to lack of efficiency and high cost. Other transfection methods, such as lipid-based techniques using Lipofectamine 2000™, are also frequently used, but have similar drawbacks due to high cost. Additionally, lipid based methods do not work well with some cell types of clinical interest, e.g., NK cells such as haNKs. NK cells have been transfected using mRNA and electroporation, for example, to genetically manipulate primary NK cells to express chimeric antigen receptors (CARs—see *Leuk Res.* (2009) 33:1255-9) or to express cytokines for autocrine growth stimulation (*Cytotherapy* (2008) 10:265-74). While commercial products exist such as Maxcyte for large scale transfection, e.g., reaction sizes of greater than 1 mL, these products are also expensive and/or lack a high-throughput capability. Similarly, these commercial products are not optimal for transfecting NK cells, often leading to poor yield and/or issues with low cell viability. Typical electroporation rates may yield 2-5% DNA transfection efficiencies with about 10-20% cell viability.

With conventional techniques, as shown in FIG. 1A, electroporation is performed using two parallel plate electrodes. In this configuration, the cells typically flow between the two parallel plates. However, the electric field is non-uniform, with cells in the middle of the chamber, shown as (a), experiencing a more uniform electric field while cells near an electrode, shown as (b), experience a non-uniform electric field and in particular, experience an electric field spike present at the boundary of the electrode. Other techniques utilize parallel plates of micromesh electrodes, as shown in FIG. 1B (Selmeczi, D. et al., "Efficient large volume electroporation of dendritic cells through micrometer scale manipulation of flow in a disposable polymer chip," Biomed Microdevices, 13: 383-392 (2011)), in which the cells pass through an upper micromesh electrode and a lower micromesh electrode. While this technique provides a more uniform electric field than passing between two parallel electrode plates, as shown by the similar trajectories of cells in the middle of the chamber (a) and near the boundary of the chamber (b), the chamber width or distance between the upper micromesh electrode and lower micromesh electrode is limited, leading to a low transfection efficiency. The configurations shown in FIGS. 1A and 1B utilize an electric field strength of about 1-1.3 kV/cm (e.g., 200V/2 mm for parallel plates, 40V/400 um for parallel micromesh electrodes).

In other aspects, single cell electroporation chips have been used for transfection. In this technique, a silicon chip may comprise a plurality of linear channels, with each channel having opposing electrodes placed on opposite sides of the channel. The cells pass through the channel and are exposed to an electric field. With this type of technique, DNA transfection efficiencies of about 68% with cell viability of about 79% have been achieved.

Even though various transfection systems and methods exist for mammalian cells, such techniques suffer from one or more disadvantages. Accordingly, there is still a need to provide improved electroporation systems and methods, especially for high throughput, large scale manufacturing processes.

SUMMARY

The techniques presented herein are directed to various devices, systems, and methods for electroporation of cells, such as mammalian cells and nonmammalian cells, for example, for large scale continuous manufacturing processes. In particular, systems and methods for electroporation of cells using an electroporation apparatus including a first input separated from a first output by an offset distance can provide for high efficiency and viability.

In some aspects, a method of electroporating cells with a cargo is provided. The method includes flowing the cells with the cargo into an electroporation chamber. The electroporation chamber includes a first electrode, a second electrode, a first input allowing passage of the cells and the cargo into the electroporation chamber, a first output allowing passage of electroporated cells from the electroporation chamber, and a fluid channel region having a path defined therein between the first electrode and the second electrode for the cells and the cargo to flow. Further, the cells are suspended in an electroporation medium and may have a cell density of about $1 \times 10^6$ cells/ml to about $500 \times 10^6$ cells/ml. The method further includes applying multiple electrical pulses to the cells within the electroporation chamber, wherein: (i) each electrical pulse has a form of an exponentially discharging waveform or a square waveform, (ii) the multiple electrical pulses are applied at a field strength of about 0.3 kV/cm to about 3 kV/cm; (iii) the field strength is applied at a voltage of about 15 V to about 100 V; (iv) a time duration between each electrical pulse is about 0.1 seconds to about 10 seconds; and (v) each electrical pulse has a pulse width of about 10 us to about 10,000 μs.

In another aspect, an apparatus for electroporating cells with a cargo is provided. The apparatus includes one or more electroporation chambers. Each electroporation chamber includes a first electrode, a second electrode, a first input allowing passage of the cells and the cargo into the electroporation chamber, a first output allowing passage of electroporated cells from the electroporation chamber, and a fluid channel region having a path defined therein between the first electrode and the second electrode for the cells and the cargo to flow.

In another aspect, a kit for cell transfection is provided. The kit includes the apparatus for electroporation as described herein, a first container for containing the cells for transfection and the cargo, a second container for containing the electroporated cells, tubing for fluidly connecting the first container and the second container to the apparatus for electroporating cells, and optionally, reagents such as cells for transfection, an electroporation medium, or a combination thereof.

Various objects, features, aspects and advantages of the subject matter described herein will become more apparent from the following detailed description of preferred embodiments, along with the accompanying drawing figures in which like numerals represent like components.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows an illustration of the structure of the input output chamber offset electroporation device. FIG. 3B shows an illustration of the electric field of the input output chamber offset electroporation device. FIG. 3C shows the electric field strength as a function of cell traveling distance through the input output chamber offset electroporation device. FIG. 3D shows an alternative configuration of an electroporation apparatus according to some embodiments provided herein.

FIGS. 3K-3L illustrate example microfluidics chambers for sorting cells according to some embodiments provided herein.

FIG. 4 shows a table of parameters associated with the chamber offset electroporation device, according to some embodiments provided herein.

FIGS. 13A-13D show various transfection efficiencies for different cell lines, using the methods and devices described herein.

FIGS. 14A-14E show results of transfection experiments for introducing mRNA into T-cells, using PbAE as described herein.

DETAILED DESCRIPTION

Systems and methods are provided for electroporation of cells, for example, mammalian cells (e.g., NK cells, EC-7 cells, T cells, etc.) and nonmammalian cells along with corresponding electroporation protocols that provide for high efficiency and viability, are provided. In some aspects, the electroporation protocol involves subjecting cells to multiple electrical pulses, a stepping fluid flow, a low conductivity and low osmolarity electroporation buffer, relatively moderate capacitance, and/or a relatively moderate time constant.

In various aspects, an apparatus for electroporating mammalian cells with a cargo is provided. The apparatus can include one or more electroporation chambers, wherein each electroporation chamber includes a first electrode, a second electrode, and a fluid channel region having a path defined therein between a first electrode and a second electrode. Each of the first electrode and the second electrode can be a solid electrode or a mesh electrode, such as a micromesh electrode. The apparatus also includes a first input allowing passage of the cells and cargo into the electroporation chamber, and a first output allowing passage of electroporated cells from the electroporation chamber. As used herein, "electroporated cells" include transfected cells, dead cells, and non-transfected cells. In some embodiments, the first input and the first output can be separated by an offset distance. The first electrode can be bounded by a first material and the second electrode can be bounded by a second material, which may be the same or different.

Figure 2A:
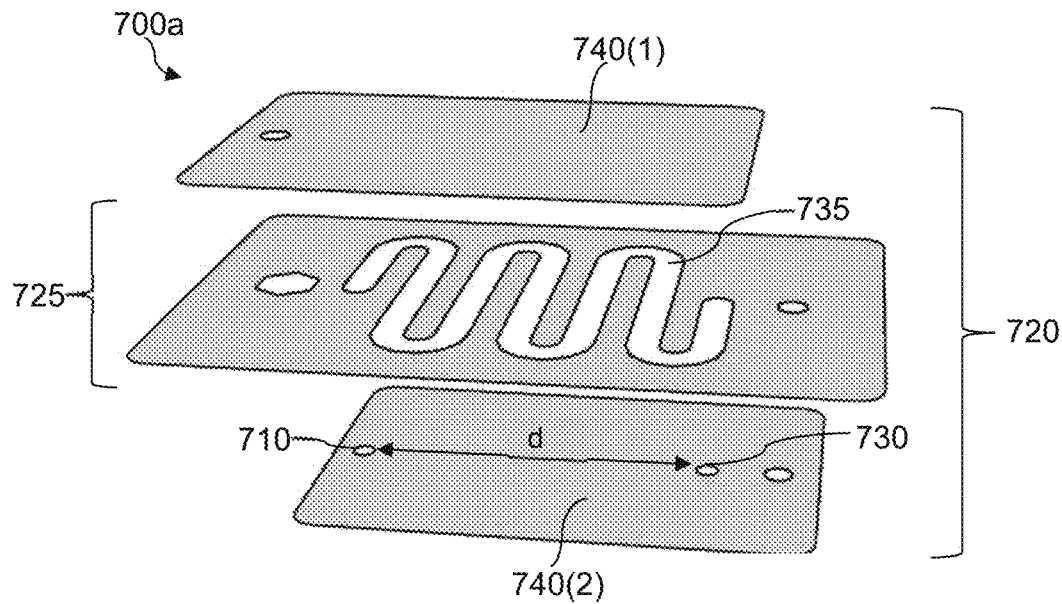
FIGS. 2A and 2B show aspects of an apparatus for electroporation according to some embodiments provided herein.

For example, FIG. 2A illustrates an exemplary apparatus for electroporating cells with cargo, which includes an electroporation apparatus 700a. The electroporation apparatus 700a includes an electroporation chamber 720 comprising two electrodes, a first electrode 740(1) and a second electrode 740(2), for example, shown here in alignment with one another. The electroporation apparatus 700a further includes a first input 710 allowing passage of the cells and the cargo into the electroporation chamber 720 and a first output 730 allowing passage of electroporated cells from the electroporation chamber 720. The first input 710 and the first output 730 may be separated by an offset distance (d) to facilitate flow of cells laterally through the electroporation chamber 720. A fluid channel region 725 is present in the electroporation chamber 720, and the fluid channel region 725 includes a path 735 defined therein between the first electrode 740(1) and the second electrode 740(2) for the cells and the cargo to flow. Although not shown, the path 735 may have a path inlet corresponding to the first input to allow passage of the cells and the cargo into the path 735 as well as a path outlet corresponding to the first output 730 to allow passage of electroporated cells from the path 735.

In any embodiment, a first input may be present or defined in a first electrode, a second electrode, or a fluid channel region. Additionally, a first output may be present or defined in a first electrode, a second electrode, or a fluid channel region. A first input and a first output both can be present in either a first electrode or a second electrode. For example, as shown in FIG. 2A, the first input 710 and the first output 730 are both present in the second electrode 740(2). Alternatively, a first input may be present in a first electrode and a first output may be present in a second electrode or a first input may be present in a second electrode and a first output may be present in a first electrode. For a fluid channel region, it is contemplated herein that a first input, a first output, or both may be present, for example in a sidewall of a fluid channel region.

Figure 2B:
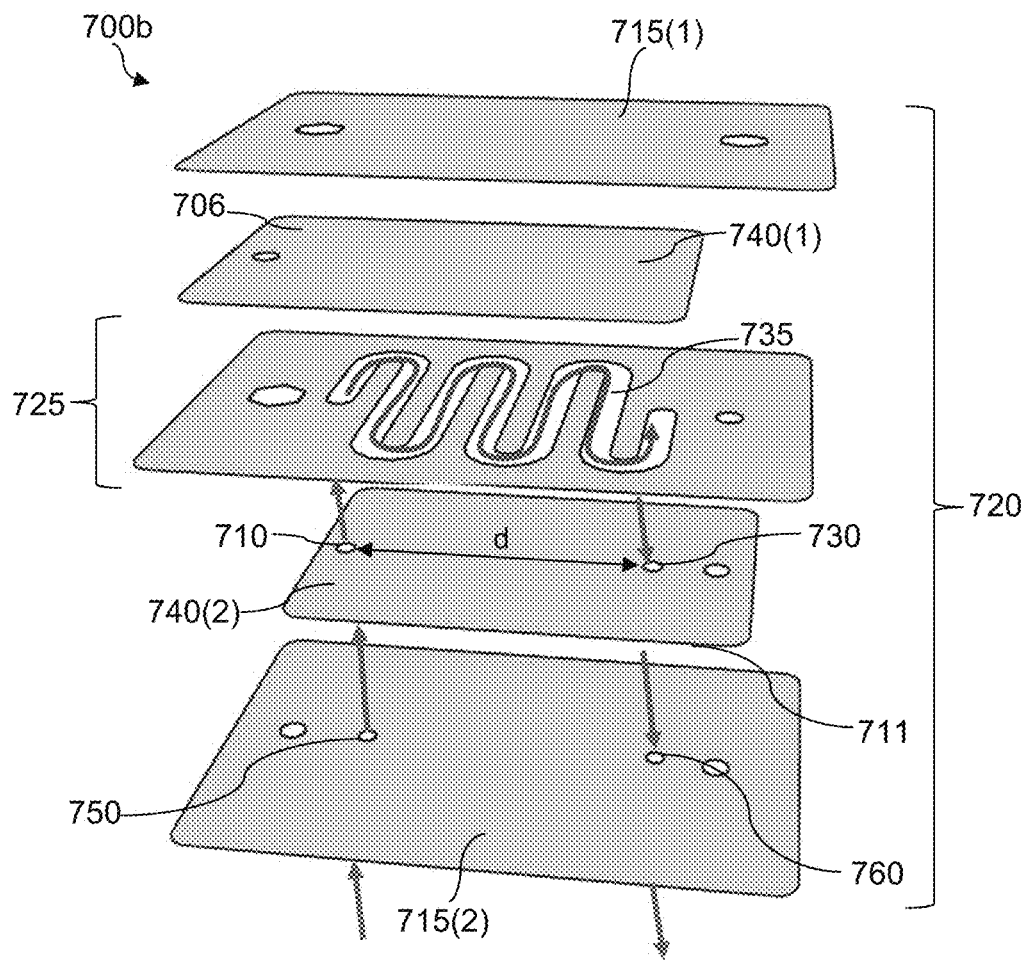

As further illustrated in FIG. 2B, an upper surface 706 of the first electrode 740(1) may be bounded by or connected to a first material 715(1) and a lower surface 711 of the second electrode 740(2) may be bounded by or connected to a second material 715(2) in electroporation apparatus 700b. For example, a first material and a second material may be a non-porous material, e.g., such as polydimethylsiloxane (PDMS) acrylic, polyethylene, polypropylene, or acrylic glass, to contain cells within the interior chamber of the electroporation device, and in particular, within the electroporation chamber between the parallel first electrode and second electrode. Additionally or alternatively, the electroporation apparatus 700b may further include a first outer input 750 for further allowing passage of the cells and the cargo into the electroporation chamber 720 and a first outer output 760 for further allowing passage of the electroporated cells from the electroporation chamber 720. A first outer input can be present or defined in a first material, and a first outer output can be present or defined in a second material. Alternatively, a first outer input can be present or defined a second material and a first outer output can be present or defined in a first material. In a further embodiment, a first outer input and a first outer output can both be present or defined in a first material or in a second material. For example, as illustrated in FIG. 2B a first outer input 750 and a first outer output 760 are both present or defined in the second material 715(2) with the arrows indicating flow direction of the cells and cargo through the electroporation device and electroporated cells exiting the electroporation device. The other openings or holes shown in FIGS. 2A and 2B and not labeled represent openings for connecting the various components of the electroporation apparatus, for example, via screws and/or plugs, as known by those of skill in the art.

Figure 2C:
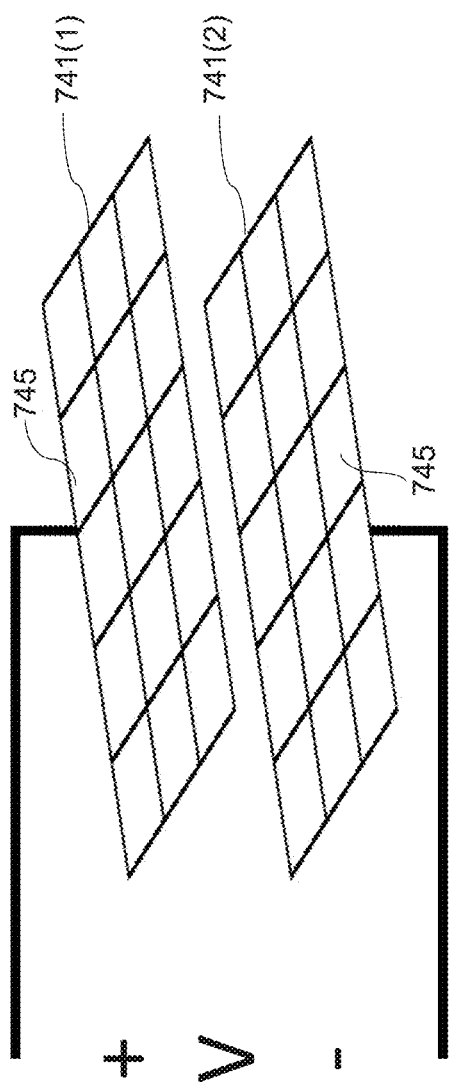
FIG. 2C show aspects of a first electrode and a second electrode according to some embodiments provided herein.

The first electrode and the second electrode each may be a solid electrode, such as a solid plate electrode, or a mesh electrode having a porosity, such as a micromesh electrode. In one embodiment, the first electrode and the second electrode are both solid electrodes, such as solid plate electrodes. In any embodiment, when the first electrode, the second electrode, or both are a solid electrode, the first electrode, the second electrode, or both comprise a plurality or an array of solid metal plates. For example, as illustrated in FIG. 2C, a first electrode 741(1) and a second electrode (741)(2) include a plurality of solid metal plates 745. Each solid metal plate 745 may be configured to apply an independent electrical field to make a specific electrical field pattern. Suitable materials that the first electrode and the second electrode may be formed from include, but are not limited to, stainless steel, polyimide, silicon, a noble metal, a Group 4 metal, a conductive material, and combinations thereof. Examples of suitable noble metals include, but are not limited to, ruthenium (Ru), rhodium (Rh), palladium (Pd), silver (Ag), osmium (Os), iridium (Ir), platinum (Pt), and gold (Au). Examples of Group 4 metals include titanium (Ti), zirconium (Zr), hafnium (Hf) and rutherfordium (Rf). Examples of suitable conductive materials include, but are not limited, to indium tin oxide (ITO), carbon nanotubes (CNTs) and conductive polymers, such as poly(3,4-ethylenedioxythiophene) polystyrene sulfonate (PEDOT:PSS).

Figure 2D:
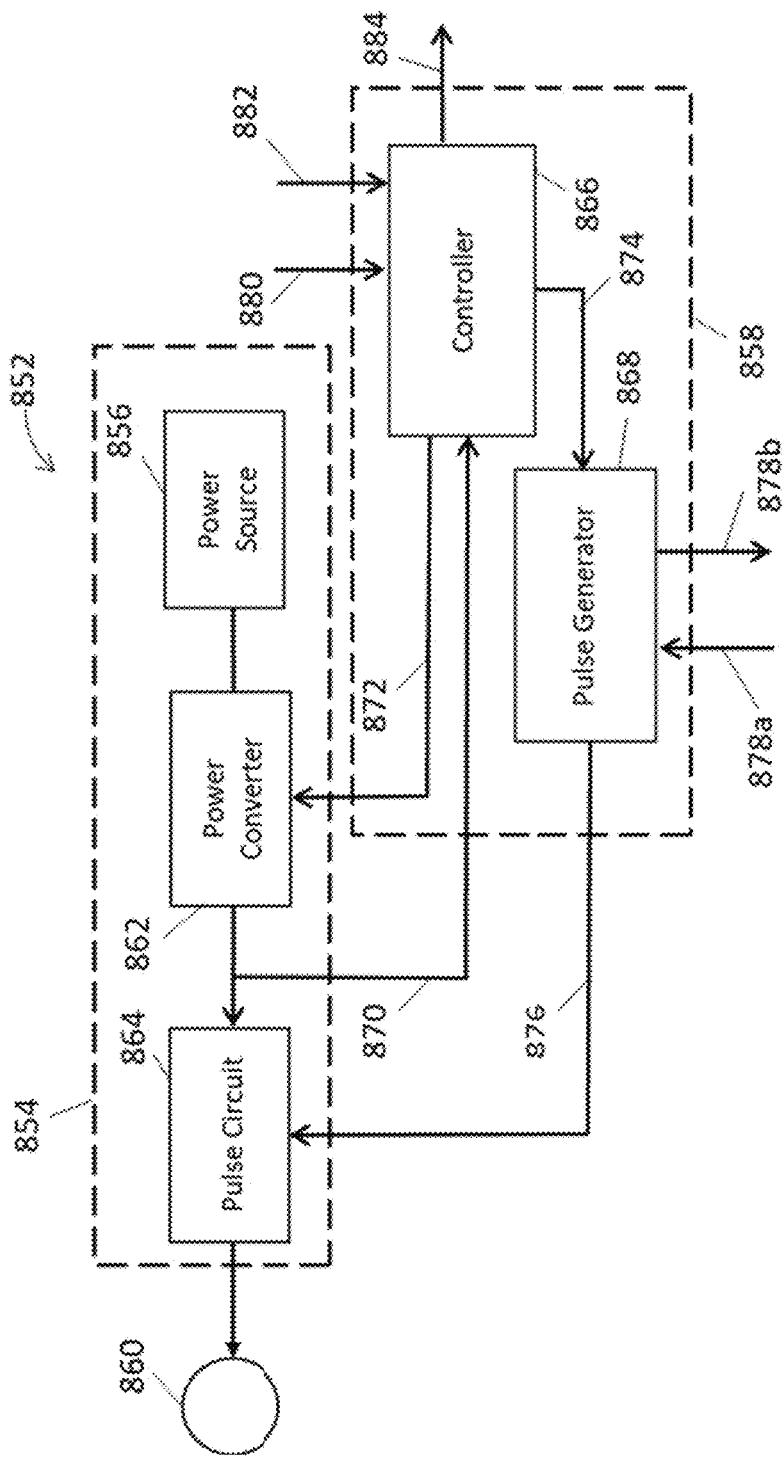
FIG. 2D is a block diagram of an apparatus for generating and providing electrical pulses to cells in an electroporation apparatus as described herein according to some embodiments provided herein.

In any embodiment, any one of the electroporation apparatuses disclosed herein may include components for providing electrical pulses to cells during an electroporation process with the electroporation parameters described herein. For example, FIG. 2D illustrates an apparatus 852 for generating and providing electrical pulses to cells, as explained herein. Specifically, and as shown in FIG. 2D, the apparatus 852 includes a power supply 854 and a control circuit 858 coupled to the power supply 854. The power supply 854 provides electrical pulses to an electroporation apparatus 860 (e.g., any one of the example electroporation apparatuses disclosed herein). For example, In the example of FIG. 2D, the power supply 854 includes a power source 856, a power converter 862 coupled to the power source 856, and a pulse circuit 864 coupled between the power converter 862 and the electroporation apparatus 860. The power converter 862 may include DC-DC power conversion circuitry and/or AC-DC power conversion circuitry depending on, for example, the type of power provided by the power source 856. For example, the power converter 862 may receive DC power from the power source 856 (e.g., one or more batteries), and output a regulated DC voltage to the pulse circuit 864. In such examples, the power converter 862 may include DC-DC power conversion circuitry having any suitable converter topology (e.g., buck, boost, etc.). In other examples, the power converter 862 may receive AC power from the power source 856 (e.g., AC mains). In such examples, the power converter 862 may include AC-DC power conversion circuitry having any suitable converter topology (e.g., AC-DC rectifier, PFC boost, etc.).

The pulse circuit 864 of FIG. 2D receives a DC voltage from the power converter 862, and converts the DC voltage into DC electrical pulses for the electroporation apparatus 860. For example, the pulse circuit 864 may include one or more switching devices (not shown) for interpreting the DC voltage from the power converter 862 and creating the electrical pulses. In other examples, the pulse circuit 864 may include other suitable circuitry for generating the electrical pulses for the electroporation apparatus 860.

As shown in FIG. 2D, the control circuit 858 includes a controller 866 and a pulse generator 868 coupled to the controller 866. The controller 866 receives a feedback signal 870 representing an output parameter (e.g. the output voltage) of the power converter 862, and generates one or more control signals 872 for the power converter 862 to control one or more switching devices (not shown) in the power converter 862 based on the feedback signal 870. For example, the controller 866 may control the power converter's switching devices to regulate the output voltage of the power converter at a defined value (e.g., a desired amplitude of the electrical pulses). In some examples, the controller 866 may decrease or increase the output voltage based on the feedback signal 870 and/or other signals disclosed herein.

Additionally, and as shown in FIG. 2D, the controller 866 may generate a signal 874 for the pulse generator 868, and the pulse generator 868 may generate one or more control signals 876 for the pulse circuit 864 to generate the electrical pulses based on the received signal from the controller 866. For example, the signal 874 may be start and/or stop signals instructing the pulse generator 868 to begin generating the electrical pulses. In some examples, the pulse generator 868 may adjust the frequency, pulse width, duty cycle, etc., of the electrical pulses based on the received signal from the controller 866.

In some examples, the control circuit 858 may receive one or more additional signals for controlling the power converter 862 and/or the pulse generator 868. For example, and as shown in FIG. 2D, the pulse generator 868 in the control circuit 858 may optionally receive one or more signals 878a. The signal(s) 878a may be feedback signals from the pulse circuit 864, the electroporation apparatus 860, etc., and used for controlling the pulse circuit 864 to generate the electrical pulses. Additionally, and as shown in FIG. 2D, the controller 866 in the control circuit 858 may optionally receive one or more signals 880 representing feedback signals from the pulse circuit 864, the electroporation apparatus 860, etc., and/or one or more signals 882 representing user defined instructions from a user interface. In such examples, the signal(s) 880 and/or the signal(s) 882 may be used for controlling the pulse circuit 864 and/or the power converter 862, monitoring the pulse timing, etc. In some examples, the apparatus 852 may include one or more sensing devices (not shown) for monitoring a chip voltage and/or a chip current associated with the electroporation apparatus 860. In such examples, the pulse generator 868 and/or the controller 866 may receive the sensed chip voltage and/or the sensed chip current via the signal(s) 878a, 880, and then control the pulse circuit 864 and/or the power converter 862 based on the sensed chip voltage and/or current.

The control circuit 858 may also generate one or more additional signals for control purposes. For example, the controller 866 may optionally generate one or more signals 884 for other components of the electroporation apparatus, and/or components external to the electroporation apparatus. In such examples, the signal(s) 884 may represent user feedback provided to a user interface, control signals for controlling a motor (e.g., a stepper motor) of a fluid pump, a peristaltic pump, pinch valves in the apparatus, etc. Additionally, the pulse circuit 864 may optionally generate one or more signals 878b for other components of the electroporation apparatus, and/or components external to the electroporation apparatus. For example, the pulse circuit may generate the signal(s) 878b for the sensing devices to instruct the sensing devices to begin voltage and current monitoring.

Figure 2E:
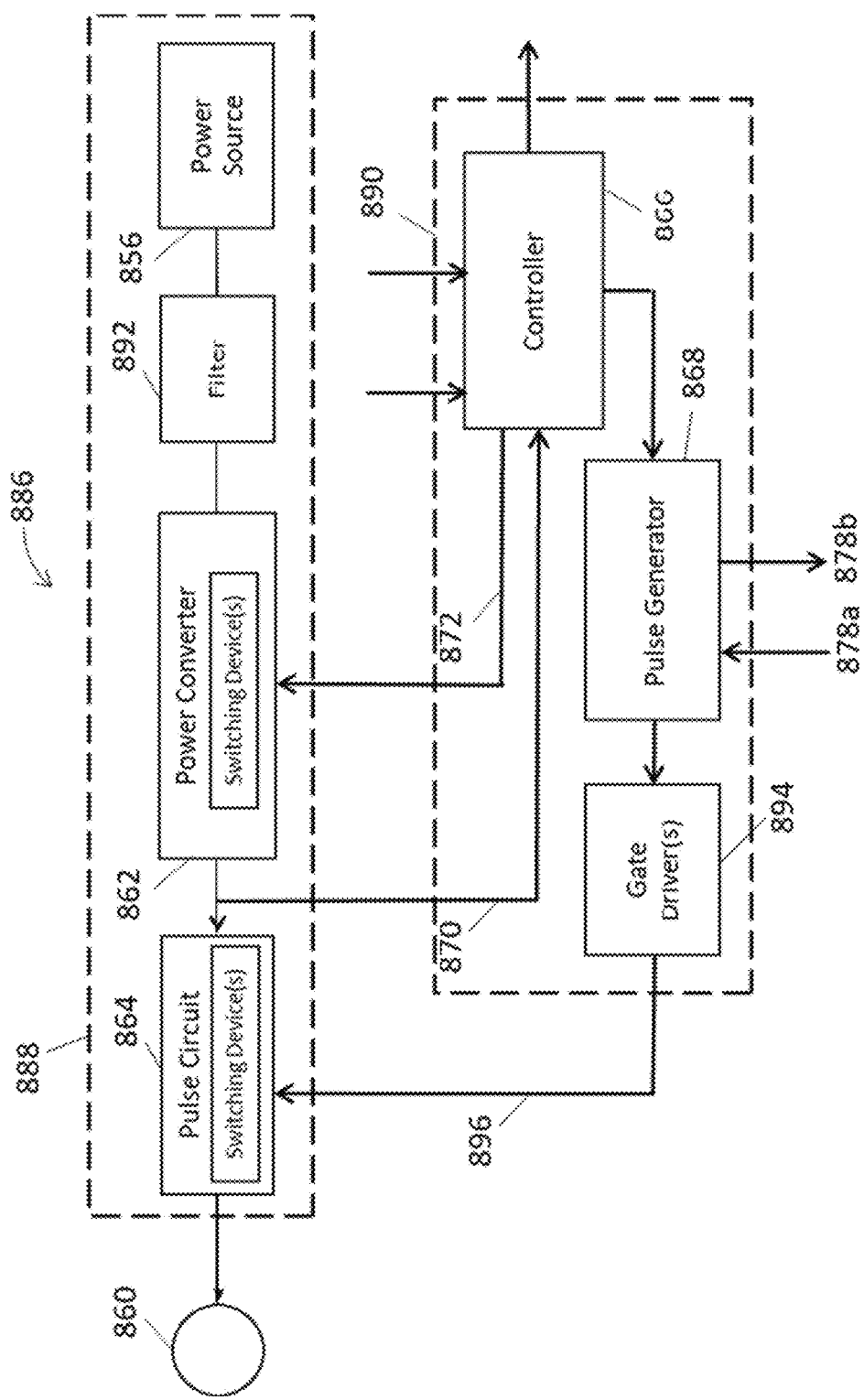
FIG. 2E is a block diagram of a further apparatus for generating and providing electrical pulses to cells in an electroporation apparatus as described herein according to some embodiments provided herein.

FIG. 2E illustrates another example apparatus 886 for generating and providing electrical pulses to cells, as explained herein. As shown, the apparatus 886 includes a power supply 888 coupled to the electroporation apparatus 860 and a control circuit 890 for controlling the power supply 888. The power supply 888 and the control circuit 890 of FIG. 2E are similar to the power supply 854 and the control circuit 858 of FIG. 2D, but include additional components. For example, the power supply 888 includes the power source 856, the power converter 862 and the pulse circuit 864 of FIG. 2D, and a filter 892 coupled between the power source 856 and the power converter 862. The filter 892 may include one or more components such as capacitors, inductors, etc. (not shown) for smoothing an electrical signal from the power source 856.

Additionally, and shown in FIG. 2E, the control circuit 890 includes the controller 866 and the pulse generator 868 of FIG. 2D, and one or more gate drivers 894 coupled to the pulse generator 868. In the example of FIG. 2E, the gate driver(s) 894 receive a signal from the pulse generator 868, and generate one or more pulse width modulated (PWM) control signals 896 for controlling one or more switching devices (e.g., MOSFETs) in the pulse circuit 864. Additionally, the control circuit 890 may receive and/or generate any one or more of the various signals referenced in FIG. 2D. For example, the controller 866 may receive the feedback signal 870, and generate the control signal(s) 872 for controlling one or more switching devices (e.g., MOSFETs) in the power converter 862, as explained above.

The control circuit disclosed herein may include hardware components and/or programmed software components for performing various functions, including the functions disclosed herein. For example, any one of the control circuits 858, 890 of FIGS. 2D and 2E may include one or more sensors for monitoring parameters of the power supplies 854, 888 (as explained herein), parameters associated with the electroporation apparatus 860, etc. The parameters may include electrical parameters associated with the power supplies 854, 888 and/or the electroporation apparatus 860, fluidic parameters associated with the electroporation apparatus 860, etc. In such examples, the control circuits 858, 890 may control the power supplies 854, 888, and/or other components of the apparatuses 852, 886 (e.g., a fluid pump, etc.) based on the parameters. It is contemplated herein that the any one of power supplies 854, 888 described herein and any one of control circuits 858, 890 can provide electrical pulses and electroporation parameters as further described below, for example, waveform, field strength, voltage, a time duration between each electrical pulse, pulse width, duration of each electrical pulse, etc. For example, any one of control circuits 858, 890 can provide one or more of the following: (i) each electrical pulse has a form of an exponentially discharging waveform or a square waveform; (ii) the multiple electrical pulses are applied at a field strength of about 0.3 kV/cm to about 3 kV/cm; (iii) the field strength is applied at a voltage of about 15 V to about 100 V; (iv) a time duration between each electrical pulse is about 0.1 seconds to about 10 seconds; and (v) each electrical pulse has a pulse width of about 10 μs to about 10,000 μs.

In some embodiments, the first electrode may be an upper micromesh electrode and the second electrode may be a lower micromesh electrode. In such embodiments, an electroporation chamber may include an upper micromesh electrode, a lower micromesh electrode, and a path defined between the upper micromesh electrode and the lower micromesh electrode for the cells and the cargo to flow. The upper micromesh electrode and the lower micromesh electrode each have a porosity, for example to allow passage of cells through the micromesh electrodes either into or out of the electroporation chamber. For example, an upper micromesh electrode and lower micromesh electrode can each have a porosity of open area of about 30% to about 50%. A width of a pore opening of an upper micromesh electrode and a lower micromesh electrode can be about 70 μm to about 140 μm. The upper micromesh electrode can be bounded by a first material, and the lower micromesh electrode can be bounded by a second material. The first material includes a first input allowing passage of cells into the electroporation chamber, and the second material includes a first output allowing passage of electroporated cells from the electroporation chamber. Additionally or alternatively, instead of the cells and/or cargo traveling through pores of the upper micromesh electrode to enter the electroporation chamber, the upper micromesh electrode may optionally include a second input to allow passage of cells and/or cargo into the electroporation chamber. The second input may be substantially aligned with the first input in the first material. Additionally or alternatively, instead of the electroporated cells traveling through pores of the lower micromesh electrode to exit the electroporation chamber, the lower micromesh electrode may include a second output to allow passage of electroporation out of the electroporation chamber. The second output may be substantially aligned with the first output in the second material.

Figure 3A:
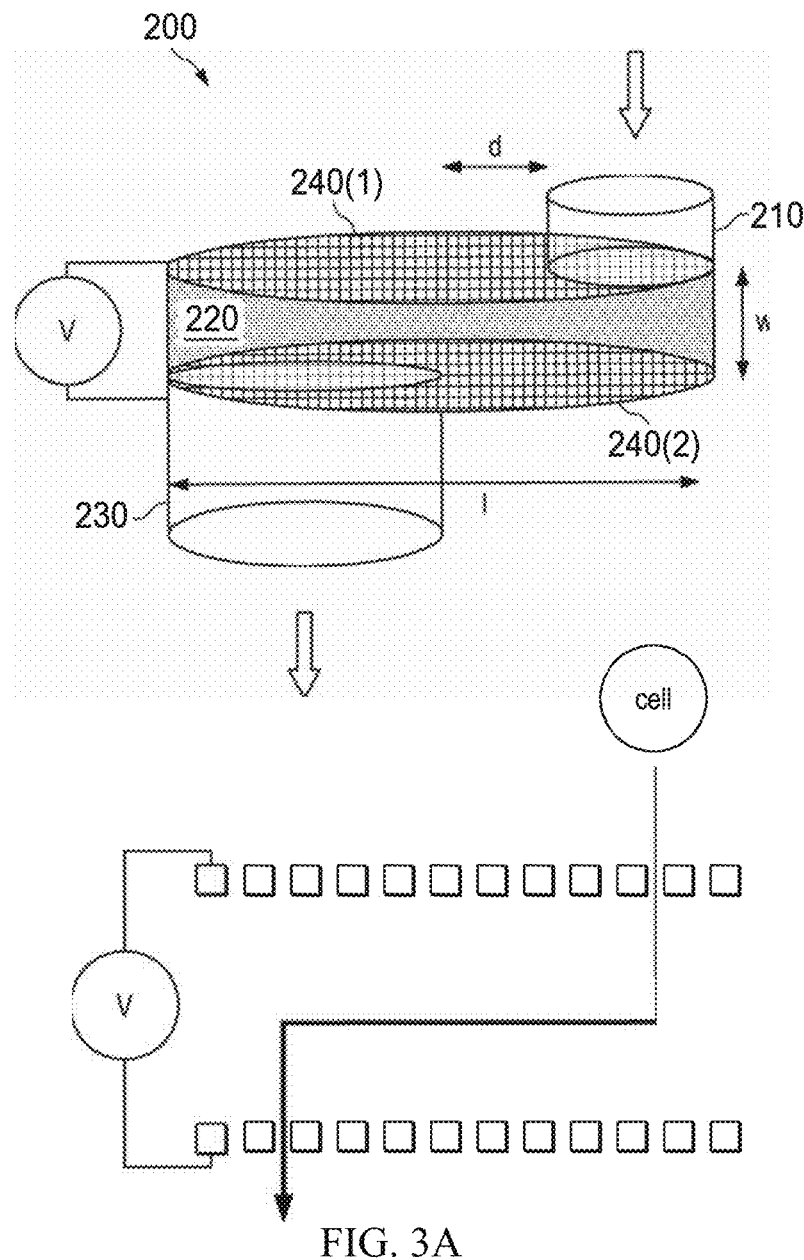
FIGS. 3A-3D show aspects of an apparatus for electroporation including an electroporation device according to some embodiments provided herein.

For example, FIG. 3A illustrates an exemplary apparatus for electroporating cells with cargo, which includes an IOCO electroporation device 200 including micromesh electrodes. The IOCO electroporation device 200 comprises two micromesh electrodes, an upper micromesh electrode 240(1) and a lower micromesh electrode 240(2), shown here in alignment with one another. The upper surface of the upper micromesh electrode 240(1) may be bounded a first material and the lower surface of the lower micromesh electrode 240(2) may be bound be a second material. For example, the first material and the second material may be a non-porous material, e.g., such as polydimethylsdoxane (PDMS) acrylic, polyethylene, polypropylene, to contain cells within the interior chamber of the electroporation device, and in particular, within the chamber 220 between the two parallel micromesh electrodes. A first input 210 is formed (a region without PDMS) on the upper micromesh electrode 240(1), and a first output 230 is formed (a region without PDMS) on the lower micromesh electrode 240(2). Thus, in this example, the upper and lower micromesh electrodes 240(1) 240(2) span the length of the electroporation chamber 220, bounded by a first material (an upper PDMS layer) and a second material (a lower PDMS layer), to direct the flow of cells along a lateral distance of the chamber. An opening (first input 210) in the first material (upper PDMS layer) and an opening (first output 230) in the second material (lower PDMS layer) is separated by an offset distance (d) to facilitate flow of cells laterally through the electroporation chamber 220.

In any embodiment, an electroporation chamber as described above may have any desired shape, including but not limited to circular, oval, square, rectangular, or a polygon.

In any embodiment, an electroporation chamber width (w) may range from about 0.01 mm to about 15 mm, 0.01 mm to about 10 mm, 0.01 mm to about 7.5 mm, 0.01 mm to about 5 mm, about 0.05 mm to about 5 mm, about 0.1 mm to about 15 mm, 0.1 mm to about 10 mm, 0.1 mm to about 7.5 mm, about 0.1 mm to about 5 mm, about 1 mm to about 15 mm, about 1 mm to about 10 mm, about 1 mm to about 7.5 mm, about 1 mm to about 5 mm, about 2 mm to about 10 mm, about 2 mm to about 5 mm, about 0.01 mm to about 4 mm, about 0.1 mm to about 4 mm, about 1 mm to about 4 mm, about 0.01 mm to about 2 mm, about 0.05 mm to about 1 mm, about 0.1 mm to about 0.5 mm, or about 0.2 mm to about 0.4 mm. In some aspects, the chamber width (w) is about 0.3 mm or about 4 mm.

In some aspects, an offset distance (d) between the first input and first output may range from about 0.1 cm to about 10 cm, from about 0.1 cm to about 5 cm, from about 0.1 cm to about 4 cm, from about 1 cm to about 3 cm, In some aspects, the offset distance (d) about 2 cm. In some aspects, there is no overlap between the input and the output.

The first input and/or second input are in fluid communication with the electroporation chamber, and the electroporation chamber is in fluid communication with the first output and/or second output. The input(s), output(s), and electroporation chamber may additionally comprise one or more valves, regulators, pumps, or any other microfluidic components, for controlling the flow of cells through the electroporation chamber.

In some aspects, both the first input and first output may be positioned in the first material on the upper micromesh electrode, provided that a suitable offset distance is maintained between the first input and the first output. Additionally or alternatively, both the second input and the second output may be present in the upper micromesh electrode. In other aspects, both the first input and first output may be positioned in the second material on the lower micromesh electrode, provided that a suitable offset distance is maintained between the first input and the first output. Additionally or alternatively, both the second input and the second output may be present in the lower micromesh electrode.

In some embodiments, the cells may enter the first input flowing in a first direction. Once passing through the first electrode or the second electrode, the flow of the cells can change direction, flowing laterally in a path along the length of electroporation chamber in a direction perpendicular or substantially perpendicular to the first direction. Once reaching the first output, the flow of the cells can change direction again, exiting the electroporation chamber, in a second direction parallel to the first direction.

In some aspects a voltage is applied across the parallel first and second electrodes, suitable to produce an electric field in the range from about 0.3 kV/cm to about 3 kV/cm. Typical electric fields range from about 1-1.3 kV/cm (e.g., 40V/300 um) for haNKS, and about 0.3-1 kV/cm for EC-7 cells. In some aspects, the voltage may be about 10V, about 20V, about 30V, about 40V, about 50V, about 75V, about 100V, or about 200V, or any suitable range therein, or more.

In some aspects, the diameters of the first input, the second input, the first output and the second output may be about the same. In other aspects, the diameter of the first input may be greater or lesser than the diameter of the first output and/or the diameter of the second input may be greater or lesser than the diameter of the second output. For example, the diameter of the first input and/or the second input may range from about 0.1 mm to about 10 mm, from about 1 mm to about 7 mm, from about 3 mm to about 5 mm, or may be about 4 mm. The diameter of the first output and/or the second output may range from about 0.1 mm to about 10 mm, from about 1 mm to about 7 mm, from about 3 mm to about 5 mm, or may be about 4 mm.

In any embodiment, a length (l) of the electroporation chamber may range from about 2 mm to about 100 mm, about 2 mm to about 80 mm, about 2 mm to about 60 mm, about 2 mm to about 40 mm, about 2 mm to about 20 mm, about 5 mm to about 100 mm, about 5 mm to about 80 mm, about 5 mm to about 60 mm, about 5 mm to about 40 mm, about 5 mm to about 20 mm about 5 mm to about 15 mm, from about 8 mm to about 12 mm, or may be about 10 mm.

In any embodiment, a height (h) of the electroporation chamber may range from about 100 μm to about 1000 μm, about 100 μm to about 750 μm, about 100 μm to about 500 μm, about 100 μm to about 300 μm, about 100 μm to about 200 μm, about 200 μm to about 1000 μm, about 200 μm to about 750 μm, about 200 μm to about 500 μm, or about 200 μm to about 300 μm. In some aspects, the chamber height (h) is about 284 μm.

In any embodiment, a ratio of length (l) to width (w) (l/w) can be about 1 to about 50, about 1 to about 40, about 1 to about 20 or about 1 to about 10.

Figure 3B:
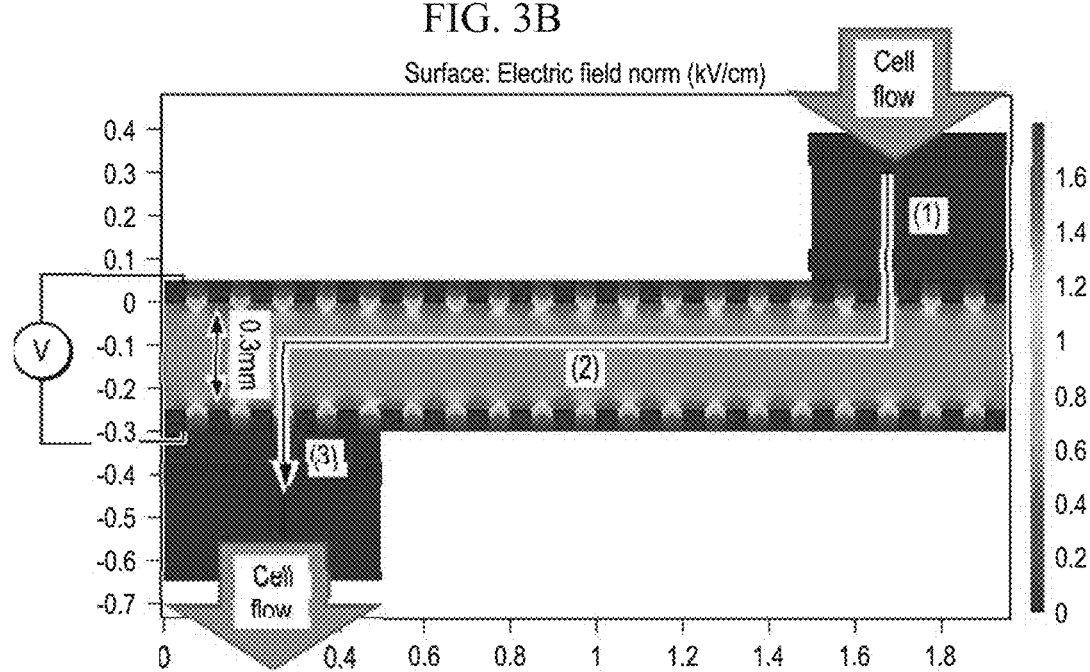

In any embodiment, once the cells enter the electroporation chamber, the cells are exposed to a uniform electrical field until exiting the electroporation chamber. For example, FIG. 3B is an illustration of the electric field in the IOCO electroporation device 200. Position (1) refers to a cell in the input (first input 210), position (2) refers to a cell in the electroporation chamber, and position (3) refers to a cell in the output (first output 230).

Figure 3C:
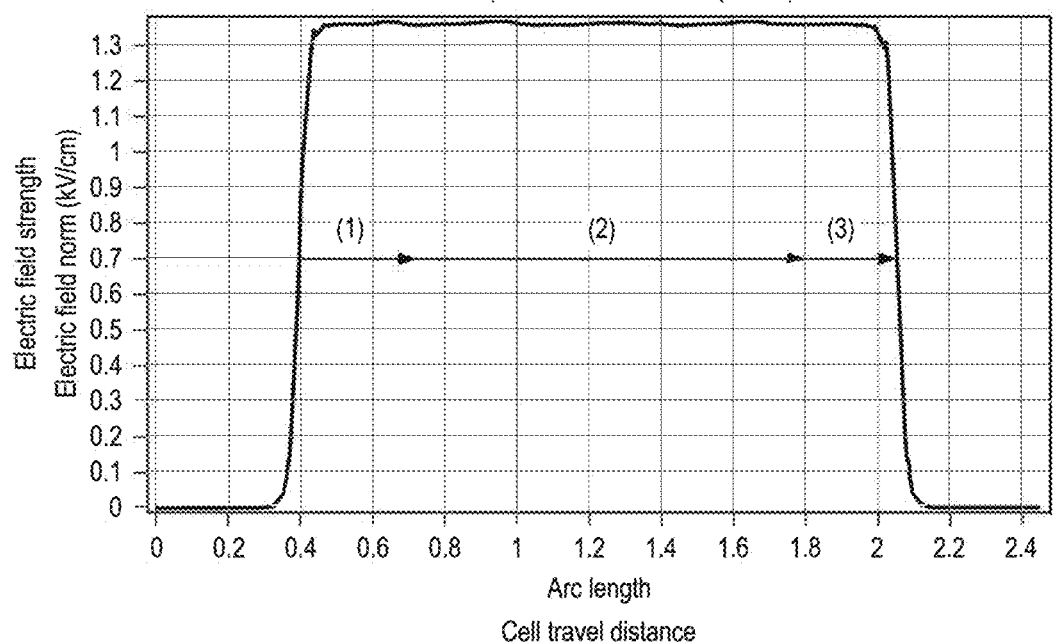

FIG. 3C is a plot of the electric field strength versus cell travel distance through the IOCO electroporation device 200. Cells in the input (first input 210), shown at position (1), are not exposed to an electric field until they have passed through the micromesh electrode into the electroporation chamber. Within the electroporation chamber, shown as position (2), the cells experience a uniform (maximum strength) electric field while traveling along the length of the chamber. Once in the output (first output 230), shown at position (3), cells are not exposed to an electric field.

Figure 3D:
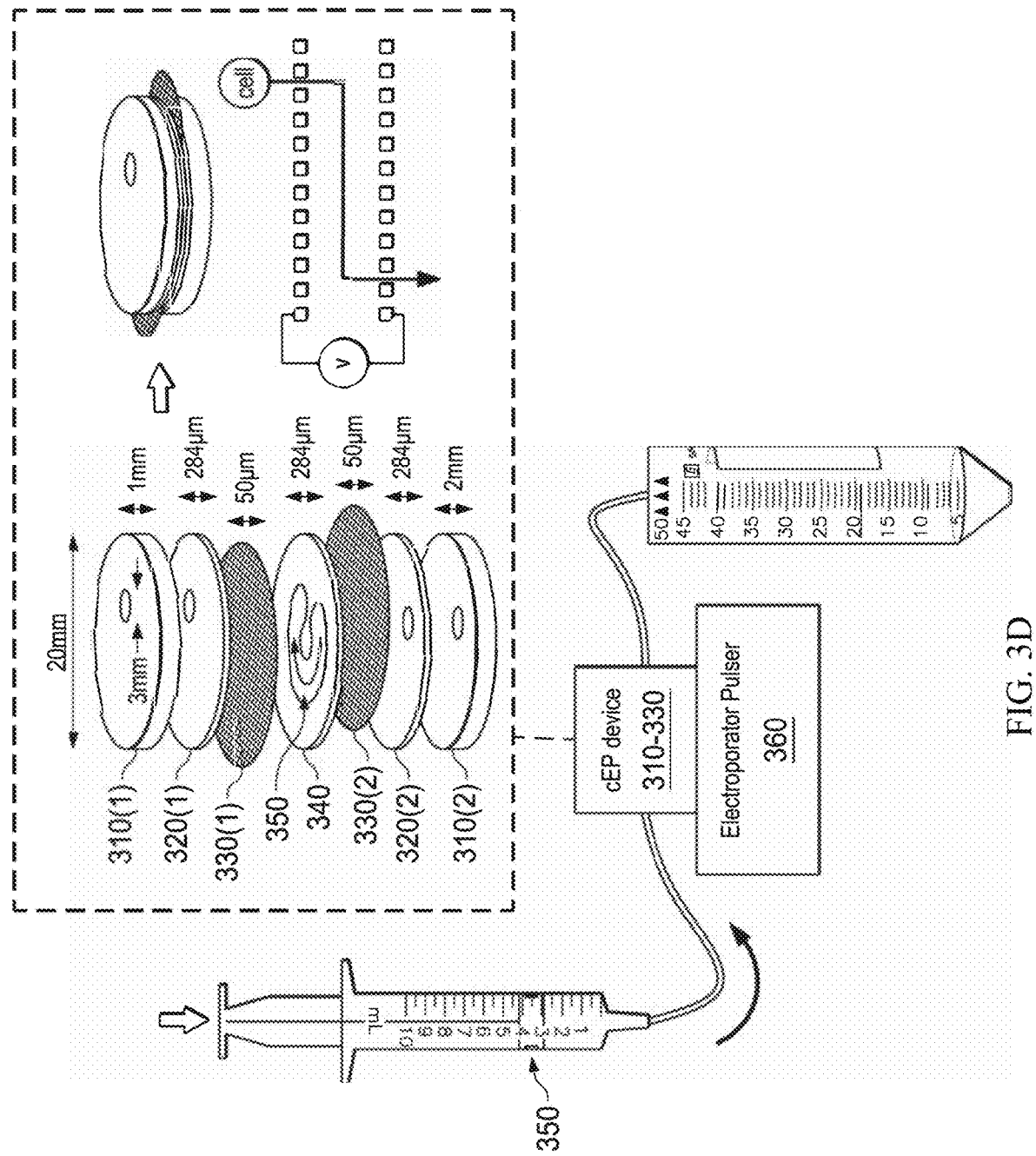

FIG. 3D shows an alternative configuration of an electroporation apparatus presented herein including an electroporation device 310-330. In this embodiment, instead of having a linear (horizontal) flow path between the upper and lower meshes, the cells may take a curved or circular (horizontal) flow path between the upper and lower meshes. The linear flow path and the curved flow path may each include at least one segment that extends parallel to a plane defined by a surface of at least one of the upper and lower meshes.

In this example, the various layers of an electroporation device 310-330 are shown in FIG. 3D. Solid outer plates 310(1) and 310(2) (e.g., plastic, metal, or any other suitable material) encapsulate the device. An adhesive layer or other suitable material (e.g., double sided tape, pressure sensitive adhesive material, etc.) 320(1) (first material) is placed between the upper solid outer plate 310(1) and the upper mesh 330(1), and an adhesive layer or other suitable material (e.g., double sided tape, pressure sensitive adhesive layer, etc.) 330(2) (second material) is placed between the lower outer plate 310(2) and the lower mesh 330(2). Another adhesive layer (e.g., pressure sensitive adhesive material or double sided tape, etc.) (340) comprising a curved channel or curved path 335 through which the cells and cargo may flow is positioned between the upper and the lower meshes 330(1) 330(2). Fluid may be driven through the electroporation device 310-330 by a syringe 350. The electroporation device 310-330 may also interface with an electroporator pulser 360. In any embodiment, the electroporation device 310-330 may be a continuous electroporation device wherein cells flow through the device in a continuous manner.

Figure 3E:
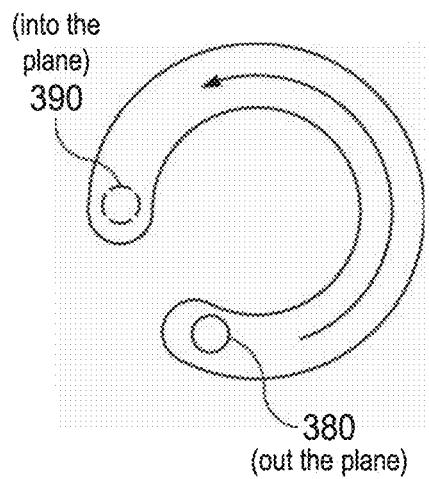
FIGS. 3E-3G show aspects of a path in an electroporation chamber according to some embodiments provided herein.
Figure 3F:
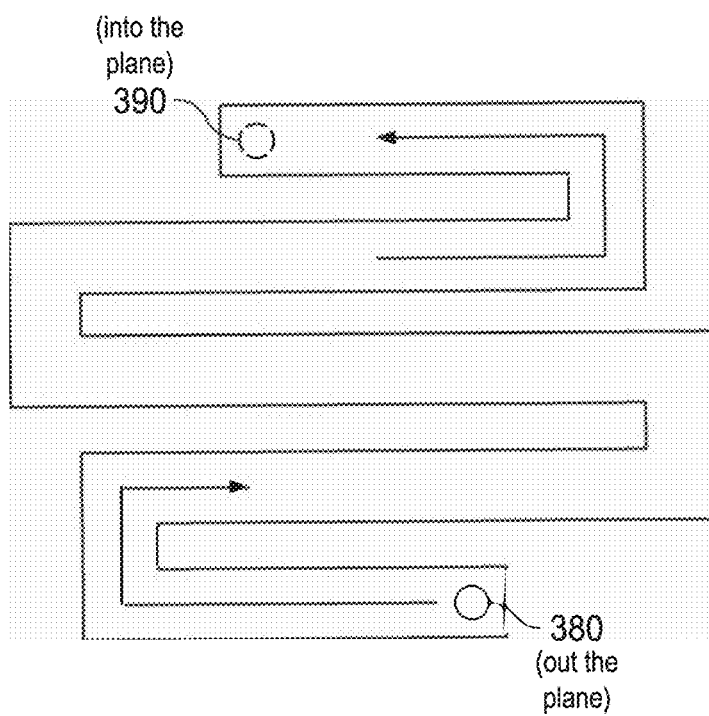
Figure 3G:
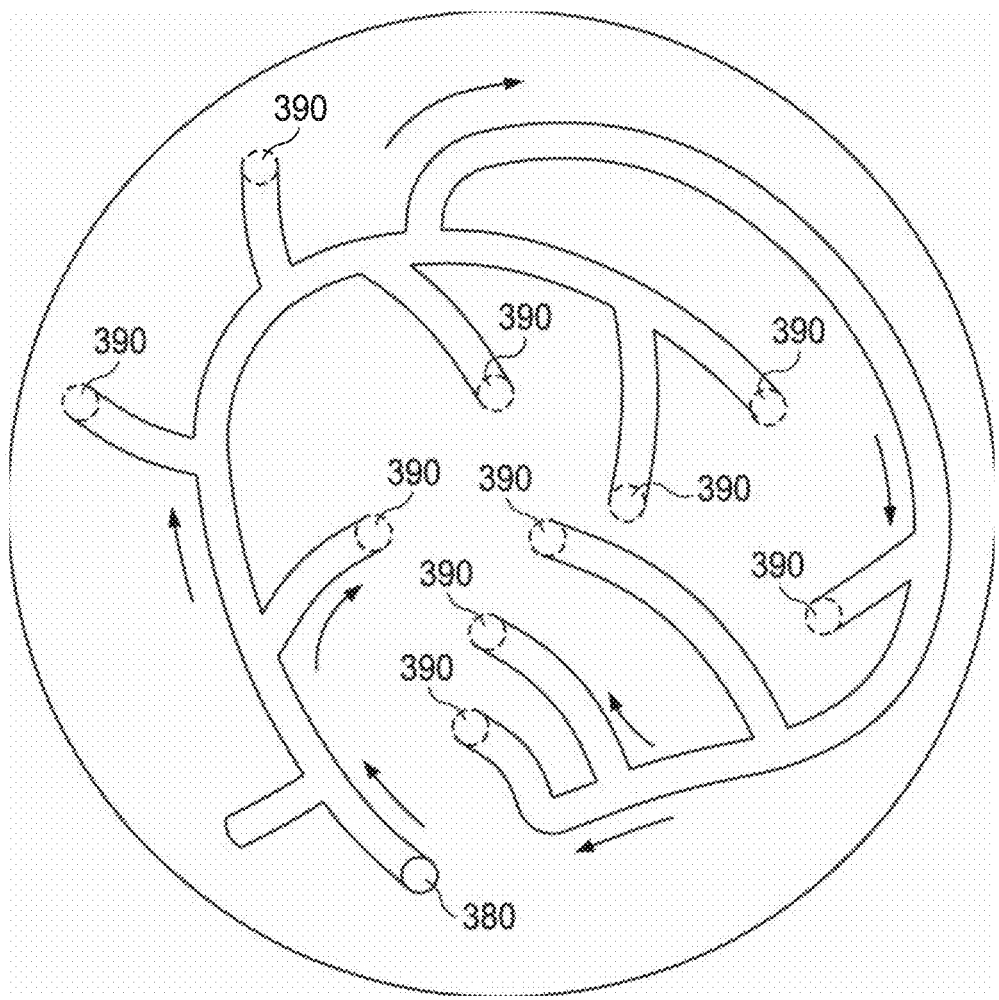

A path for the cells and cargo to flow through the electroporation chamber is defined in the electroporation chamber, for example, in a fluid channel region as described above between the first electrode (e.g., a solid electrode or an upper micromesh electrode) and the second electrode (e.g., a solid electrode or a lower micromesh electrode). It is understood that any suitable path, provided that the path includes at least one horizontal flow segment that is parallel to at least one of the first electrode (e.g., a solid electrode or an upper micromesh electrode) and the second electrode (e.g., a solid electrode or a lower micromesh electrode), are contemplated by the embodiments provided herein. The horizontal flow segment may form greater than or less than any of 1/10, 1/4, 1/2, 3/4, 7/8, or 9/10 of the length of the path extending between the upper and lower micromesh electrode. In some cases, the path may be linear, curved, branching, circuitous, tortuous, or any combination thereof. Examples of a curved path include, but are not limited to a circular path, a spiral path, a conical path, or any combinations thereof. For example, as illustrated in the FIG. 3B, a path is linear where arrows illustrate flow of cells. As illustrated in FIGS. 2A, 2B, 3D and 3E, a path is curved where arrows illustrate flow of cells. As illustrated in FIG. 3F, a path may be linear with one or more changes in direction or switch-backs with arrows illustrating flow of cells. As illustrated in FIG. 3G, a path may be circular and have one or more branches. As shown in FIGS. 3E-3G, the paths may include an inlet 380 (out of the plane), which may correspond to the first input or be substantially aligned with the first input, and one or more outlets 390 (into the plane), which may correspond to the first output or be substantially aligned with the first output. The length of the path may be adjusted, e.g., shortened or lengthen, depending upon the particular characteristics of the electroporation process.

Figure 3H:
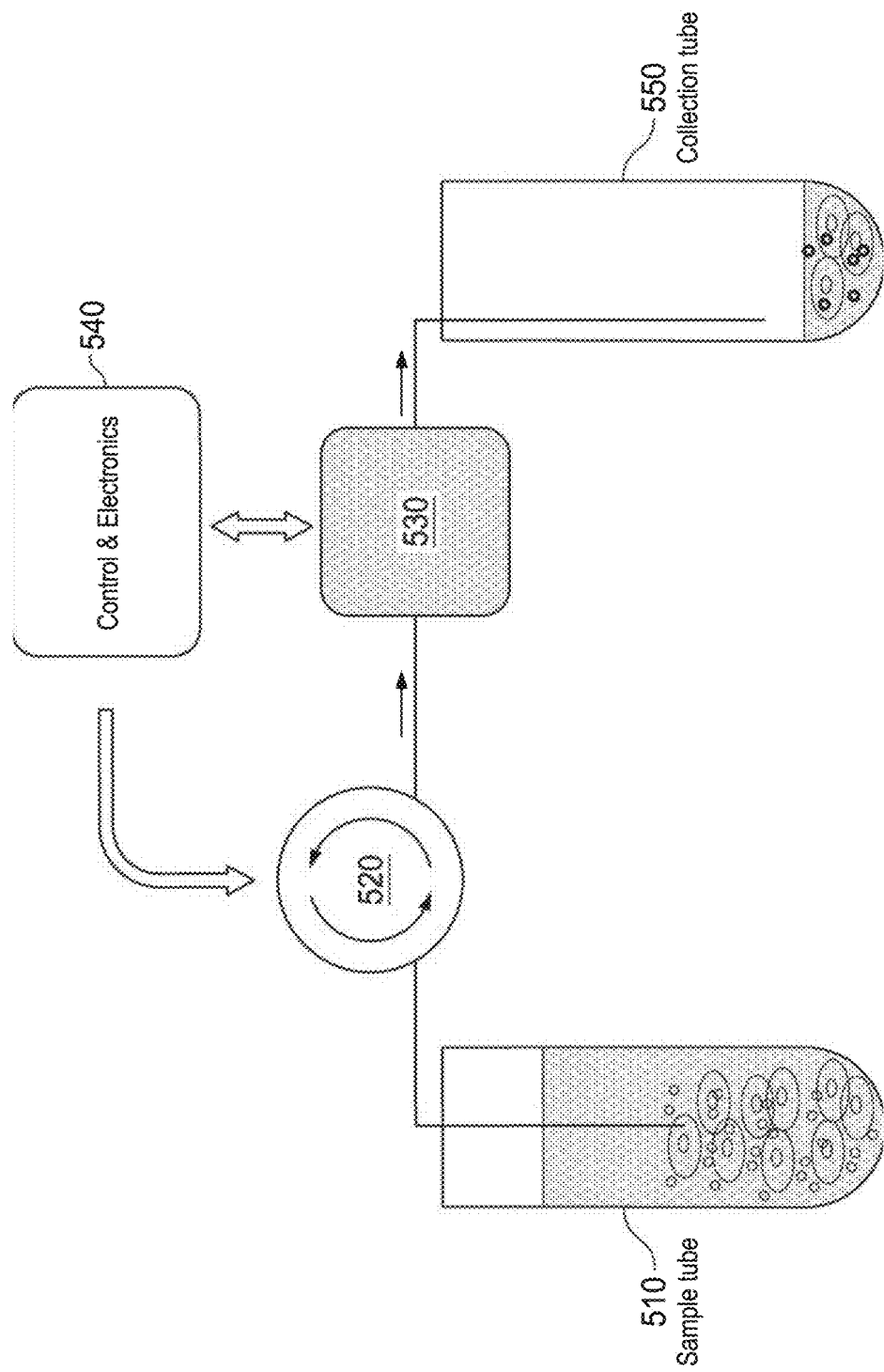
FIGS. 3H-3J show alternative configurations of an electroporation apparatus according to some embodiments provided herein.

In any embodiment, the electroporation apparatuses described herein may include a means for generating flow of cells from a sample tube into an electroporation chamber of an electroporation device and flow through the device into a collection tube. For example, as illustrated in FIG. 3H, a flow generating means 520 is in fluid communication, for example, via tubing, with a sample tube 510 containing cells and/or cargo for transfection and an electroporation device 530. The flow generating means 520 can generate flow of the cells and/or cargo through tubing from the sample tube 510, through the electroporation device 530 and into collection tube 550. Although not shown, an air filter device may be in fluid communication with the contents of the sample tube 510, the collection tube 550, or both. The flow generating means may be any suitable pump, for example, a peristaltic pump or a syringe pump. It is contemplated herein that more than one flow generating means 520 may be present in an electroporation apparatus. For example, one or more flow generating means 520 may present between and in fluid communication with the sample tube 510 and the electroporation device 530 and one or more flow generating means 520 may present between and in fluid communication with the collection tube 550 and the electroporation device 530. Additionally or alternatively, the electroporation device 530 and/or the flow generating means 520 may also interface with a controller 540, for example, including an electroporator pulser.

Figure 3I:
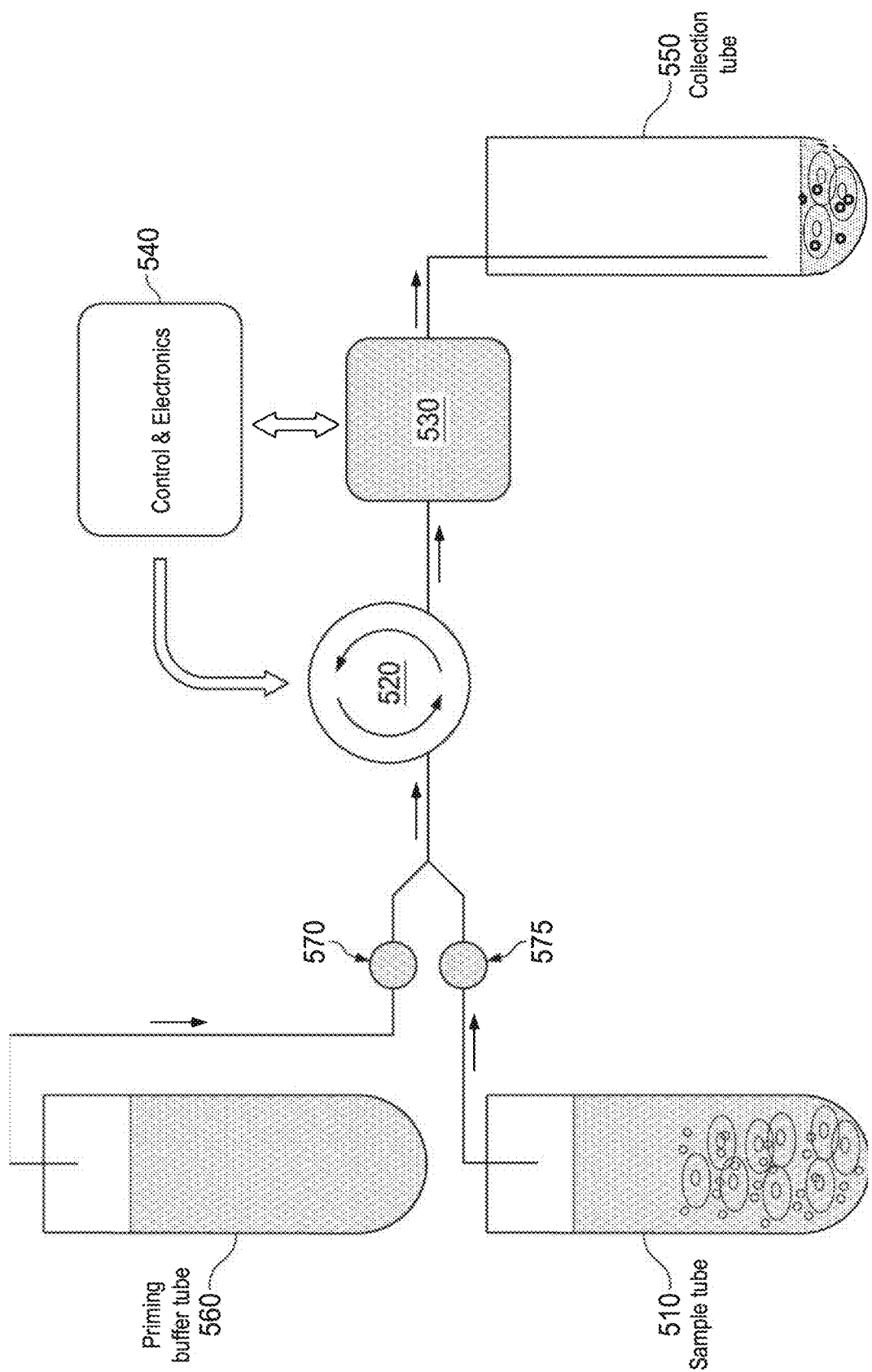

In any embodiment, the electroporation apparatuses described herein may also include a priming buffer tube in fluid communication with the electroporation device to deliver priming buffer as needed. Examples of a suitable priming buffer include, but are not limited to distilled water, deionized water, isotonic buffer, and combinations thereof. For example, as illustrated in FIG. 3I, a priming buffer tube 560 is in fluid communication with electroporation device 530. A valve 570 may be opened to deliver priming buffer to the electroporation device 530 via flow generating means 520 or the valve 570 may be closed to stop delivery. A valve 575 may be opened to deliver cells and/or cargo to the electroporation device 530 via flow generating means 520 or the valve 575 may be closed to stop delivery. In some embodiments, valves 570 and 757 both may be opened to deliver cells and priming buffer. In some embodiments, priming buffer may be delivered first followed by delivery of cells and/or cargo.

Figure 3J:
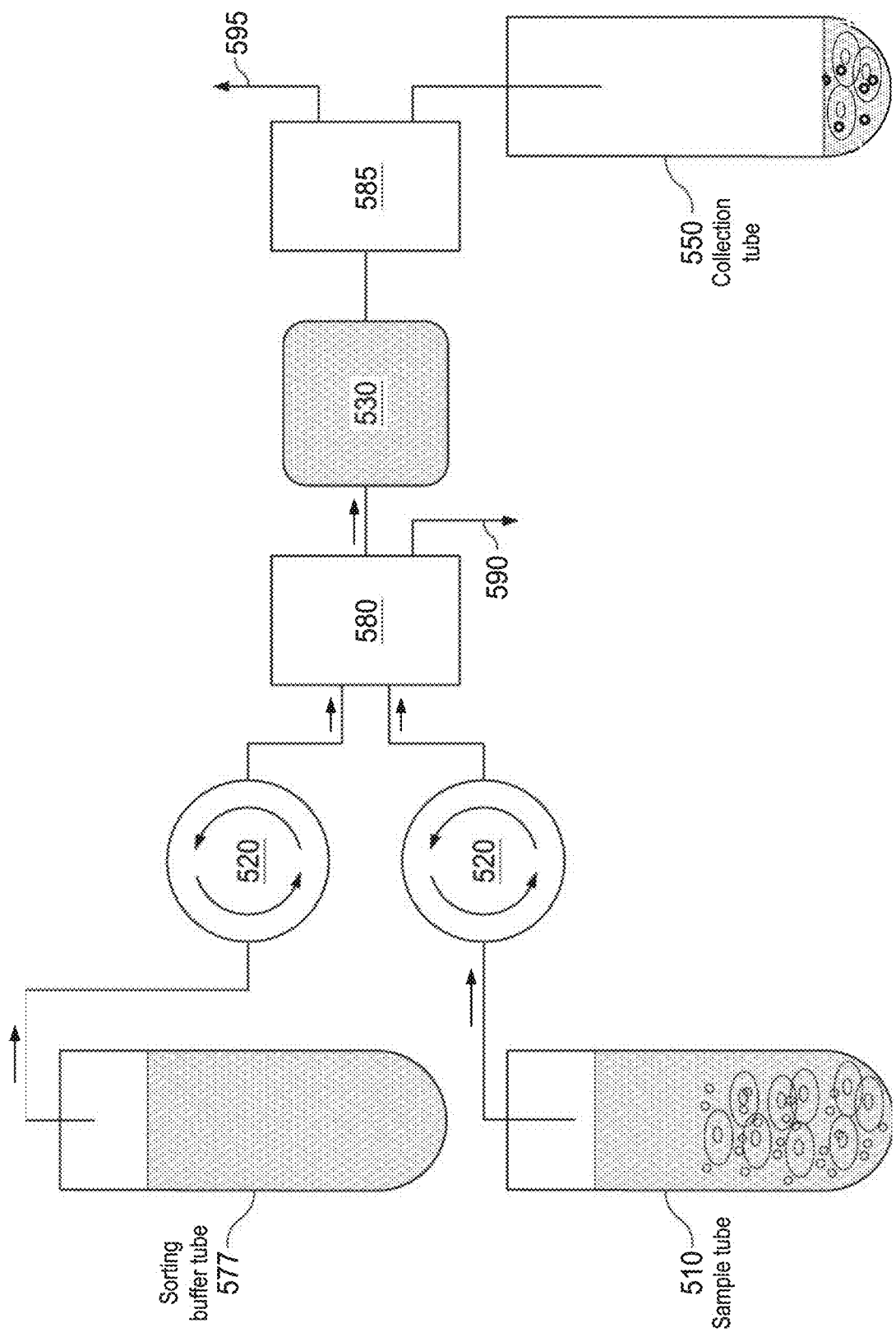

In any embodiment, the electroporation apparatuses described herein may also include a first microfluidics device for sorting the cells prior to entering an electroporation chamber of an electroporation device. For example, as illustrated in FIG. 3J, a first microfluidics device 580 can be in fluid communication with an electroporation device 530, a sample tube 510 containing cells for transfection, and optionally a buffer sorting tube 577. Flow generating means 520 can generate flow of the cells from the sample tube 510 and/or buffer from sorting tube 577 through the electroporation device 530 and into a collection tube 550. The first microfluidics device 580 is capable of pre-sorting cells, for example based on size of cells, from the sample tube 510 to the electroporation device 530. Additionally or alternatively, the first microfluidics device 580 is capable of accomplishing a buffer change of the cells from the sample tube 510. Stream 590 contains cells sorted out and not delivered to the electroporation device 530 can either be a waste stream or sent to another electroporation device with different parameters. Additionally or alternatively, a second microfluidics device 585 can be in fluid communication with the electroporation device 530 and collection tube 550. The second microfluidics device 585 is capable of sorting electroporated cells, for example based on size of the electroporated cells, prior to collection in the collection tube 550. Stream 595 contains the electroporated cells sorted out and not delivered to the collection tube 550.

Although, two microfluidics devices are shown in FIG. 3J, it is contemplated herein that only one microfluidics device may be present in an electroporation apparatus, for example, to sort cells prior to entering an electroporation chamber or to sort electroporated cells exiting an electroporation chamber.

FIG. 3K is an illustration of an example microfluidics device (e.g., microfluidics device 580, microfluidics device 585). In this example, a solution comprising cells 100 (e.g., cells for transfection, electroporated cells, transfected cells) enters a chamber 105 at input mechanism 110. Cells are illustrated as circles. The cells pass through chamber 105, which comprises a matrix of posts 115, shown here as rectangular structures distributed along a plurality of lines having a slope. As the cells pass in between the diagonally oriented rows of posts in the chamber, the cells are deflected laterally, towards a second output mechanism 122. A side view of a portion of the chamber is shown in FIG. 3L, wherein the chamber has a floor 160 and optionally has a ceiling 150, which may be of the same material as the posts 115 or a different material. Cells (black circles) are shown flowing through the matrix of posts. It is understood that the rows of posts may also be arranged in a curvilinear manner, which would also result in the cells being directed towards a side of the chamber.

In this example, two output mechanisms are shown for the chamber. The solution that exits the chamber via first output mechanism 120 (also can be referred to as a third output mechanism, when more than one microfluidics device is present) is depleted of cells, while the solution that exits the chamber via second output mechanism 122 (also can be referred to as a fourth output mechanism when more than one microfluidics device is present) is enriched in cells. In any embodiment, the second output mechanism can be in fluid communication with an electroporation chamber, for example, with a first input. Depletion refers to a state in which the concentration of cells in the solution exiting the chamber via output mechanism 120 has been reduced by 50%, 60%, 70%, 80%, 90%, 95%, 96%, 97%, 98%, or 99% as compared to the concentration of cells in the solution entering the chamber at input mechanism 110. Enrichment or concentration refers to a state in which the concentration of cells in the solution exiting the chamber via output mechanism 122 has been increased by 50%, 100%, 200%, 300%, 400%, 500%, 600%, 700%, 800%, 900%, 1000% or more as compared to the concentration of cells in the solution entering the chamber at input mechanism 110. For the cells to be directed to output mechanism 122, the deflection point 130 of the chamber should be situated such that exiting cells are routed to output mechanism 122 (and not output mechanism 120). In general, output mechanism 122 is configured to have a larger cross sectional area than output mechanism 120. In general, the output mechanisms will have a cross sectional area large enough for fluid flow at the flow rates described herein, without producing high pressures which would damage the cells or the device.

In some embodiments, the width of output mechanism 120 is greater than the width of output mechanism 122. For example, the width of output mechanism 120 is 1.5×, 2×, 2.5×, 3×, 3.5×, 4×, 4.5×, 5×, 5.5×, 6×, 6.5×, 7×, 7.5×, 8×, 8.5×, 9×, 9.5× the width of output mechanism 122. In other embodiments, the sum of the cross-sectional areas of the output mechanisms may be equal to or greater than the sum of the cross-sectional areas of the input mechanisms.

In some embodiments, the microfluidics device is configured to allow a standard pump or a syringe or the like to be connected to the microfluidics device to flow a solution comprising cells through the device. Parameters that can influence the flow of a solution though a device include the dimensions of the chamber 105, the in plane and out of plane dimensions of the posts 115, the spacing of the posts within a row (dx), the rotation of the posts (θ, the distance between rows of posts (dy), the diameter of the input mechanism, and the diameters of the output mechanisms (see, FIGS. 3M-3Q below). In some embodiments, dimensions of these parameters are selected to be compatible with applied pressure from manual operation of syringes or standard pumps (e.g., peristaltic pumps, diaphragm pumps, syringe pumps, lobe pumps, etc.) that drive flow of the solution through the device. A range of pressures are permitted, provided that the pressure does not damage the microfluidics device or the cells.

In general, cells may flow into the microfluidic device in a series (one at a time and into a particular path) or in multiples (multiple cells that flow into multiple paths).

Figure 3M:
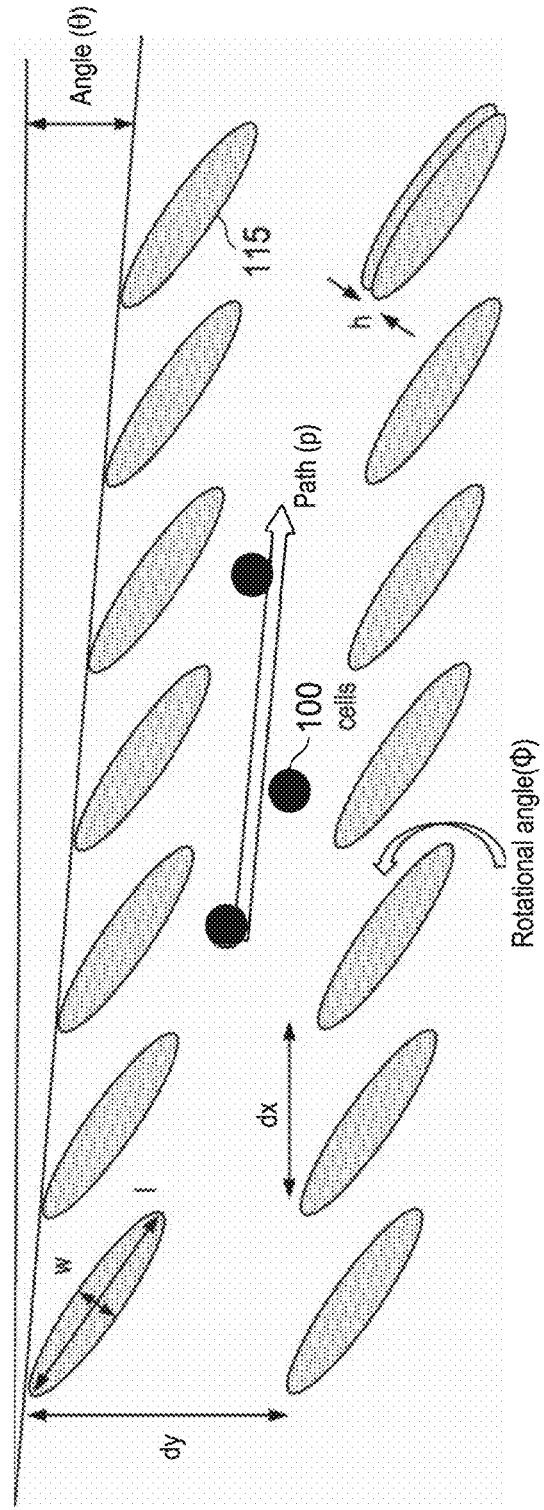
FIGS. 3M-3S are illustrations showing various aspects of the geometry and positioning of posts within the microfluidics chamber according to some embodiments provided herein.

FIG. 3M is an illustration of a top-down view of a section of chamber 105, wherein the section includes two rows of seven posts each. Cellular flow is shown along path (p). This illustration shows the positioning of posts 115 in a section of the chamber of the microfluidics device. In general, the posts are aligned along lines having a slope as defined by angle (θ) at a spacing interval (dx), which may be fixed or variable, provided that the variation does not lead to cells escaping from the path (p) between the posts.

In some embodiments, the width of the chamber is 1 mm, 2.5 mm, 5 mm, 7.5 mm, 10 mm, 12.5 mm, 15 mm, 17.5 mm, 20 mm, 30 mm, 40 mm, 50 mm, or more, or any size in between. The width of the individual paths (p) controls the characteristics of the streamlines. Any number of paths, e.g., 1, 2, 4, 8, 12, 16, 32, etc., or any range in between, may be employed depending on the width of the chamber. In other embodiments, the flow rate of fluid through the chamber may be 1 mL/hr, 2 mL/hr, 3 mL/hr, 4 mL/hr, 5 mL/hr, 6 mL/hr, 7 mL/hr, 8 mL/hr, 9 mL/hr, 10 mL/hr, 15 mL/hr, 20 mL/hr, 25 mL/hr, 30 mL/hr, 40 mL/hr, 50 mL/hr, and so forth. The chamber is desirably rectangular but may also be circular, semi-circular, V-shaped, or any other appropriate shape.

Angle (θ) is the angle between the horizontal axis with zero slope and a line having a slope along which the posts are distributed. (In this example, the angle provides a measure of the negative slope (tan (θ)=Δy/Δx) of a row of posts.) In this example, it is understood that the posts may have a positive or negative slope, as each row of posts is arranged diagonally. Here, it is understood that diagonal may encompass any orientation that is not parallel or perpendicular to the chamber, e.g., an angle between 1 and 89 degrees, between 91 and 179 degrees, between 181 and 269 degrees, or between 271 and 359 degrees, clockwise or counter clockwise. Other exemplary angle ranges may be 1 to 10 degrees, 11 to 20 degrees, 21 to 30 degrees, 31 to 40 degrees, 41 to 50 degrees, 51 to 60 degrees, 61 to 70 degrees, 71 to 80 degrees, 81 to 90 degrees, 91 to 100 degrees, 101 to 110 degrees, 111 to 120 degrees, 121 to 130 degrees, 131 to 140 degrees, 141 to 150 degrees, 151 to 160 degrees, 161 to 170 degrees, or 171 to 180 degrees.

In general, multiple rows of posts are present in a chamber, and each row has the same slope or substantially the same slope as defined by angle (θ). When cells 100 enter the chamber 105 of the microfluidics device, the cells flow through a plurality of paths (p) between the posts 115 in a lateral manner, towards a side of the chamber 105, until reaching a side of the chamber. For concentrating cells, the cells generally do not cross rows of posts, but rather, the cells typically travel along a particular path (p). The cells then exit the microfluidics chamber via output mechanism 122. In other embodiments, the posts may have a curvilinear component along the length of the chamber 105.

As used herein, the term "post" refers to a structure within the chamber having an associated in-plane dimension, an out-of-plane dimension, rotational angle, and shape. An in-plane dimension may refer to the length (l) and width (w) of the post, while the out-of-plane dimension may refer to the height (h) of the post. A tilting angle or a rotational angle (φ) refers to the rotation of the post with respect to the chamber.

Figure 3O:
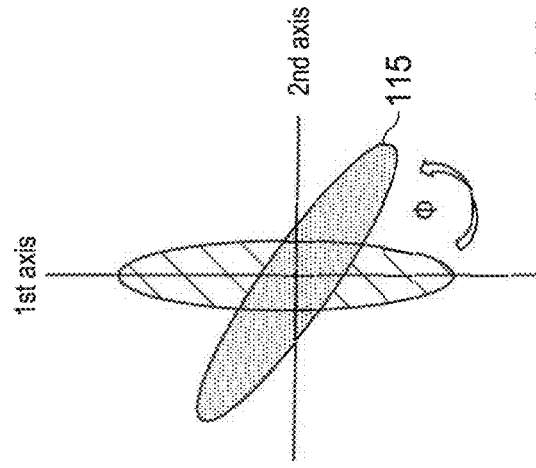

Shape refers to the 3-D characterization of the post, e.g., cylindrical, conical, pyramidal, cubic or cuboid, etc. In general, a post will be positioned such that its axis (out-of-plane dimension) is perpendicular to the surface to which it is affixed. In some embodiments, all posts within the chamber are of the same dimensions. In other embodiments, the dimensions of the posts vary as a function of space, such as depending on the position measured along the height (h) of the post. In general, the post may be of any shape, and is not limited to a particular geometric shape presented herein. The post shape may be arbitrary, as shown in FIG. 3R, represented by an axial length (l) and width (w), and a plurality of radii (r4-r12) associated with a curvature, positioned along the axial length, e.g., at a repeating constant interval or a repeating variable interval. Any number of different geometries may be described by the plurality of radii. Additionally, with reference to FIGS. 3R and 3S, one or more sides of the post may be in the shape of a straight line. Accordingly, the posts may have any suitable shape comprised of curves and/or straight lines.

In some embodiments, the posts are arranged at an interval (dx) along a line having a slope, wherein the interval is regularly spaced or fixed. For example, a post may be placed every 5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 85 μm, 90 μm, 95 μm, 100 μm, and so forth, including any value in between these ranges depending upon the size of the cell to be concentrated.

In other embodiments, the posts are distributed along a line having a slope, such that the interval is not fixed but instead varies between any two successive posts. Any interval (dx) is permitted, provided that the interval is small enough to keep the cell from escaping path (p). For example, for a variable interval, a first post may be placed at a particular location, the second post may be placed 5 μm from the first post, a third post may be placed 4 um from the second post, and so forth. The interval can be selected based on the size of the cell.

In some embodiments, the interval can be selected to be sufficiently large to allow concentration of a particular type of cell, while allowing smaller cells to exit via output mechanism 120. For example, a blood sample may comprise a plurality of different cell types of relatively small size, including red blood cells, neutrophils (e.g., 12-14 μm in diameter), eosinophils (e.g., 12-17 μm in diameter), basophils (e.g., 14-16 μm in diameter), lymphocytes (e.g., 10-14 μm in diameter), and monocytes (e.g., 20 μm in diameter). Other types of cells in the human body are much larger, e.g., ranging from 40 to 100 μm in diameter or more. In such cases, the posts may be spaced to allow red and white blood cells to pass through, while concentrating larger cells (e.g., normal cells, tumor cells, etc.). The configuration of the posts (spacing) is determined based upon the type of cell being isolated. Different sheath-to-sample flow ratios can affect size-based sorting performance.

Figure 3N:
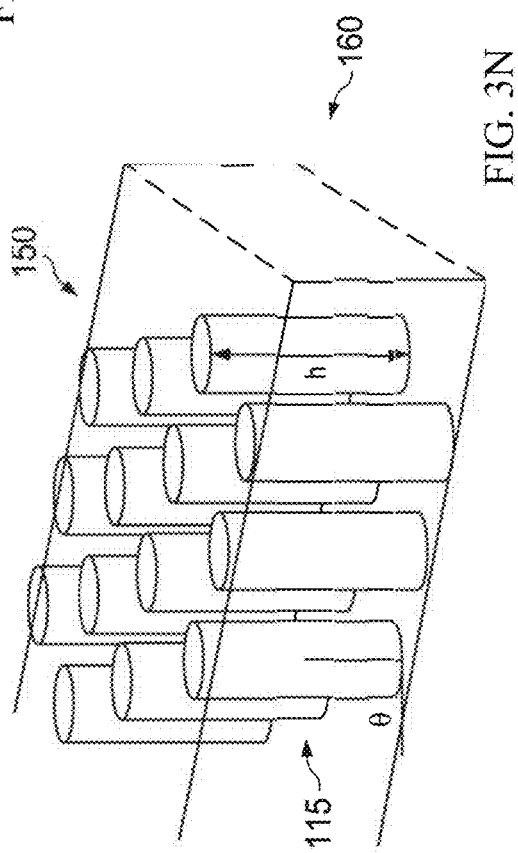

Each post has an associated length (l), width (w), also referred to as in-plane dimensions and a height (h), also referred to as an out of plane dimension (see also FIG. 3N). In some embodiments, the width of the post may be 5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 85 μm, 90 μm, 95 μm, 100 μm, and so forth or any value in between. The length of the post may be 5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 85 μm, 90 μm, 95 μm, 100 μm, and so forth or any value in between. In general, the posts may be of any shape (as viewed from the top-down orientation, and with respect to dimensions w and l), including but not limited to, circular, oval, square, rectangular, etc.

In the examples presented herein, the posts have an oval or rectangular shape. In some embodiments, the length of the post is 1.1 to 10 times greater than the width of the post; 1.1 to 5 times greater than the width of the post; 2 to 4 times greater than the width of the post; 3 to 4 times greater than the width of the post; or 2-3 times greater than the width of the post. In some embodiments, the length and width may have a ratio greater than or less than any of 20 to 1, 18 to 1, 16 to 1, 14 to 1, 12 to 1, 10 to 1, 9 to 1, 8 to 1, 7 to 1, 6 to 1, 5 to 1, 4 to 1, 3 to 1, 2 to 1, 1.1 to 1, or smaller or greater ratios.

In some embodiments, the cross section of the post may be defined by the intersection of the post with a plane that is parallel to a wall from which the post extends with height (h). The cross section may be symmetric along one or both of the length (l) and width (w) directions.

In still other embodiments, the length and the width of each post in the matrix are the same. In yet other embodiments, if the posts are circular, the radius of each post in the matrix is the same.

Additional features include the rotation angle (φ) of the post, the height or the out of plane dimension of the post, spacing between the rows (dy), and offset of the rows (xo), which are described in additional detail in FIGS. 3N-3Q and throughout the application. As used herein, the term "rotational angle" refers to the degree of rotation of a post with regard to its position in the chamber. In some embodiments, the post has a length that is greater than its width. In this embodiment, a rotational angle of zero means that the length of the post is aligned with an axis perpendicular to a side of the chamber. To describe different rotational angles, the post may be rotated in a clockwise or counter clockwise direction. As an example, the posts in FIGS. 3M-Q are rotated about 35 degrees in a counter clockwise motion to arrive at the geometry of the posts shown in these figures.

Referring to FIG. 3N, each post has an associated height (h) or out of plane dimension, such that the posts are sufficiently tall to prevent the cells from escaping from path (p) by flowing in an upward path (e.g., over the top of the posts into a different path). For example, in some embodiments, the posts will span the height of the microfluidics chamber, such the posts are in contact with the floor of the chamber 160 and the ceiling of the chamber 150. In other embodiments, the height or out of plane dimension of the post may span a fraction of the total height of the microfluidics device. For example, the posts may have a height of 1 μm, 3 μm, 5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 85 μm, 90 μm, 95 μm, 100 μm, and so forth, or any value in between.

Referring to FIG. 3O, each post has an associated rotation angle (φ) or tilt, as shown from a top down view. In the present example, the rotation of the post is determined, starting with an orientation in which the length of the post is aligned with a first axis perpendicular to the side of the chamber and the width of the post is aligned with a second axis in line with the side of the chamber, by rotating the post in a counterclockwise direction, e.g., in this example, about 35 degrees counterclockwise, until reaching the desired rotation. Any rotation angle that facilitates flow of the cells through path (p) may be utilized, and all such rotation angles are contemplated herein. In some embodiments, the rotation angle is between 1 degree and 179 degrees, between 1 degree and 89 degrees, between 5 degrees and 85 degrees, between 10 degrees and 80 degrees, between 15 degrees and 75 degrees, between 20 degrees and 70 degrees, between 25 degrees and 65 degrees, between 30 degrees and 60 degrees, between 35 degrees and 55 degrees, between 40 degrees and 50 degrees, between 30 degrees and 40 degrees, between 32 degrees and 38 degrees, between 34 degrees and 36 degrees, or 35 degrees. In other embodiments, the rotation angle may be between 91 degrees and 179 degrees, between 95 degrees and 175 degrees, between 100 degrees and 170 degrees, between 105 degrees and 165 degrees, between 110 degrees and 160 degrees, between 115 degrees and 155 degrees, between 120 degrees and 150 degrees, between 125 degrees and 145 degrees, between 130 degrees and 140 degrees, or 135 degrees.

As indicated previously, the posts are distributed along a line having a negative slope. By orienting the cells along this line, the cells flowing through path (p) are directed laterally, towards a side of the chamber, while the solution that the cells are originally suspended in is able to flow in a manner (e.g., near horizontally or horizontally) to exit the microfluidics chamber via output mechanism 120.

Figure 3P:
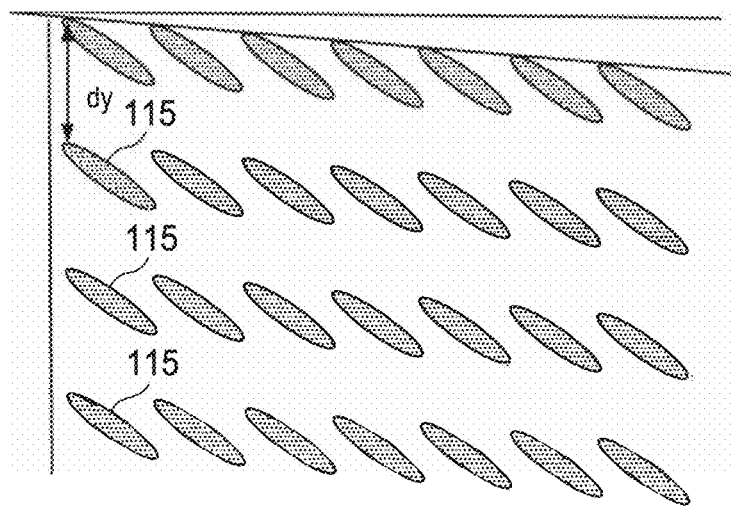

Referring to FIG. 3P, in still other embodiments, the rows of posts are spaced at an interval (dy). In some embodiments, the posts are arranged at an interval (dy) along a vertical line, wherein the interval is regularly spaced or fixed. For example, a post may be placed every 5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 85 μm, 90 μm, 95 μm, 100 μm, and so forth, including any value in between, depending upon the size of the cell to be concentrated.

In other embodiments, the posts are distributed along a vertical line, such that the interval (dy) is not fixed but instead varies between any two successive rows of posts. For example, a first row of posts may be placed at a particular location, the second row of posts may be placed 5 μm from the first row of posts, a third row of posts may be placed 4 um from the second row of posts, and so forth, aligned with respect to a vertical line. The interval (dy) can be selected based on the size of the cell to be concentrated. Any interval (dy) is permitted, provided that the interval is sufficiently wide to allow flow of the solution through the chamber without requiring high pressures, which could damage the microfluidics device. In some embodiments, successive rows of posts may have a zero offset (xo).

Figure 3Q:
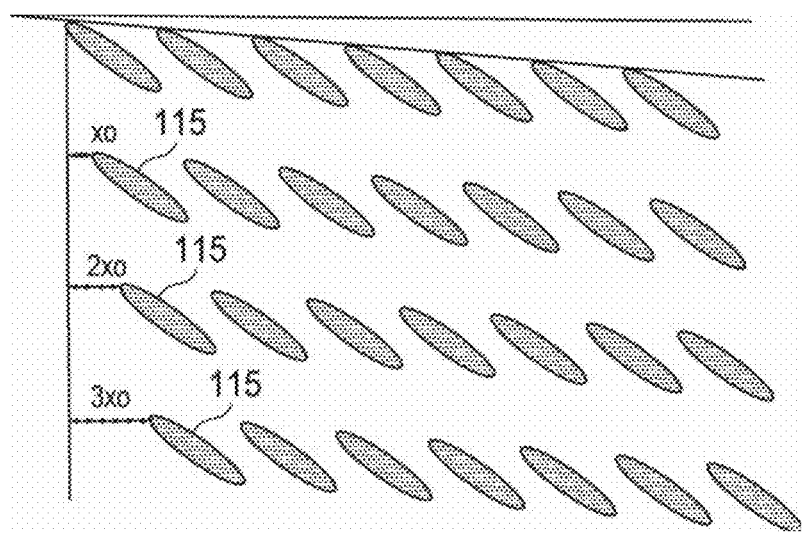
Figure 3R:
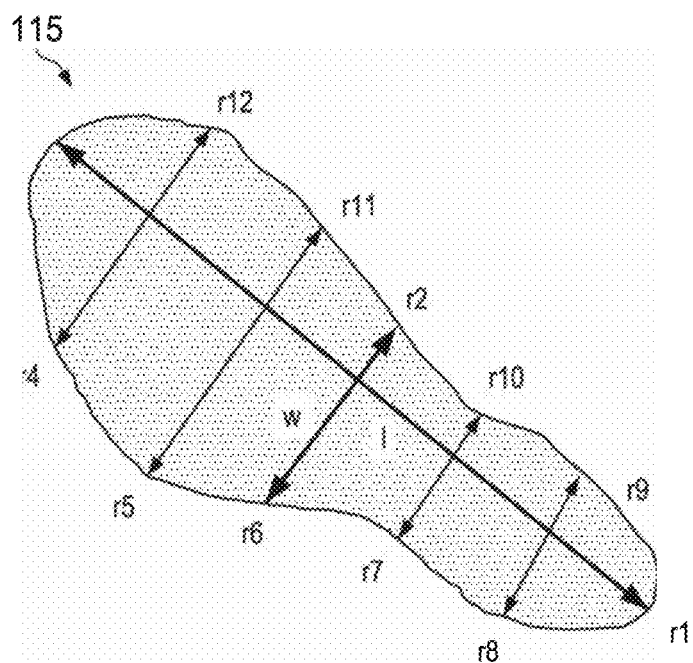
Figure 3S:
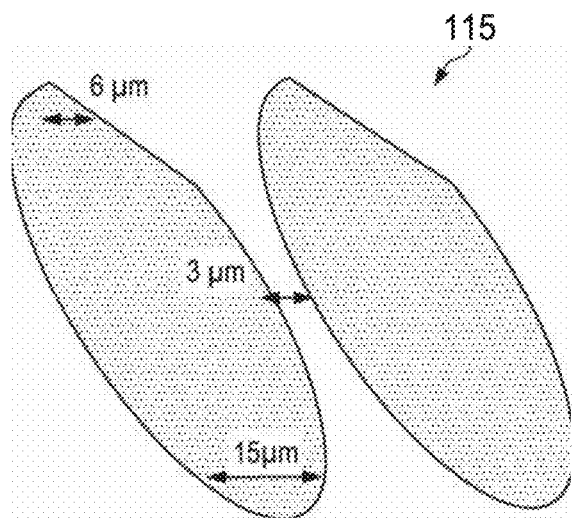

Referring to FIG. 3Q, successive rows of posts may have an offset (xo), relative to interval (dx). For example, a row (r) may be established at a particular location (e.g., using the Cartesian coordinate system x, y). The $(r+1)^{th}$ row may be displaced to the right by an amount (xo). The $(r+2)^{th}$ row may be displaced to the right by an amount (2xo). The $(r+3)^{th}$ row may be displaced to the right by an amount (3xo), and so forth up to the interval (dx). Offsets may occur in a fixed manner, such that each successive row is displaced in the same direction by a fixed amount. Alternatively, offsets may occur in a variable manner, such that each successive row is displaced in the same direction by a variable amount (up to the amount of (dx)). In other embodiments, offsets may be applied in an alternating direction, such that with regard to a row (r), the $(r+1)^{th}$ row has a fixed or variable offset in one direction, and the $(r+2)^{th}$ row has a fixed or variable offset in the opposite direction (e.g., one offset is to the right and the next offset is to the left).

The posts may be made out of any suitable material, including poly(dimethylsiloxane) (PDMS), glass, plastic, elastomers, silicon, etc. PDMS in general can be fabricated to have sub-micron resolution (e.g., below 0.1 µm features). In some embodiments, the chamber 105 and/or posts 115 may be made of PDMS. In other embodiments, the chamber may be fabricated of glass and/or silicon and/or plastic, and the posts may be fabricated using PDMS (e.g., the bottom of the chamber may be glass or silicon and the top of the chamber may be glass or plastic). Lithography, which is well known in the art, may be utilized to fabricate the chambers and posts as described herein. Materials having similar properties to PDMS may also be used to construct the microfluidic devices set forth herein.

Additionally, specific embodiments may comprise a number of additional features, including valves (e.g., between an input mechanism and the chamber, between the chamber and an output mechanism, between an output mechanism and another input mechanism or another chamber, etc.), pumps and mixers. In some embodiments, valves can be placed into PDMS during curation.

A variety of techniques can be employed to fabricate a microfluidics device. The microfluidics device may be formed from one or more of the following materials: poly(methylmethacrylate) (PMMA), polycarbonate, polystyrene, polyethylene, polyolefins, silicones (e.g., poly(dimethylsiloxane) (PDMS)), silicon, and combinations thereof. Other materials are well known in the art.

Methods for fabricating a chamber with posts and a microfluidics device using the materials referenced herein are also known in the art and include but are not limited to embossing, laser micromachining, milling, molding (e.g., thermoplastic injection molding, or compression molding), photolithography (e.g., stereolithography or x-ray photolithography), silicon micromachining, wet or dry chemical etching, etc.

Silicon fabrication techniques using photolithography followed by wet (KOH) or dry etching (reactive ion etching with fluorine or other reactive gas) can be employed for glass materials. For example, a glass master can be formed by conventional photolithography, which serves as a master template for molding techniques to generate a plastic or PDMS-based device.

A microfluidics device may be fabricated in one or more layers that are joined together, e.g., by adhesives, clamps, heat, solvents, etc. Alternatively, the microfluidics device may be fabricated as a single piece, e.g., using stereolithography or other three-dimensional fabrication techniques.

In some embodiments, due to the deformability of cells, a gap distance may be selected that is about 5 µm or less as compared to the size (e.g., a diameter) of the cell being concentrated. In other embodiments, the gap distance may be selected that is about 5 µm or greater as compared to the size (e.g., a diameter) of the cell being sorted. For rigid cells or microspheres having the same or similar diameter as a deformable cell, the gap distance may be different (e.g., larger for rigid cells) as compared to the gap distance for deformable cells of the same diameter.

Figure 3T:
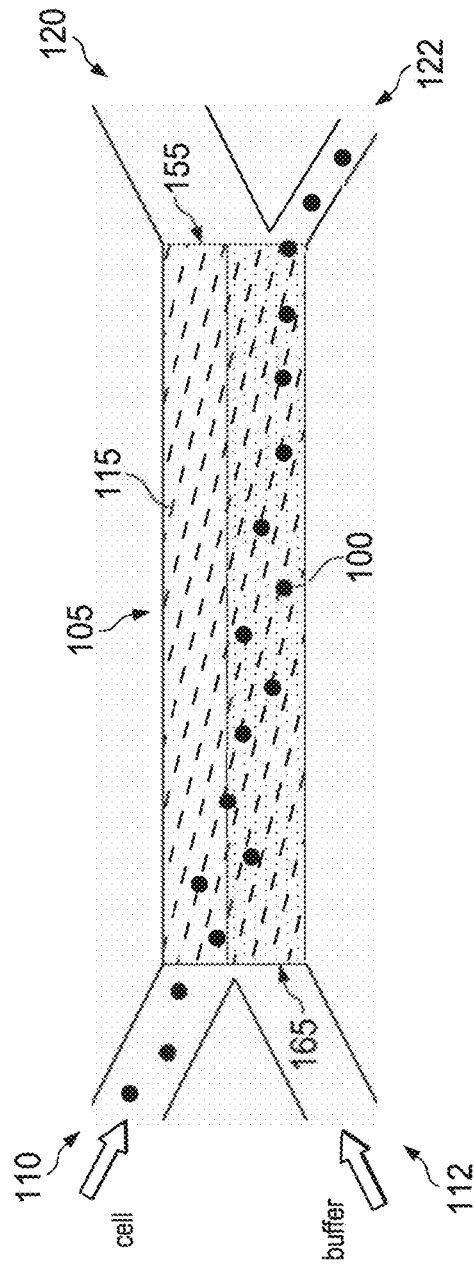
FIG. 3T illustrates an example microfluidics chamber for changing buffers according to some embodiments provided herein

FIG. 3T is an illustration of another example microfluidics cell concentrator. In this example, a first solution comprising cells 100 enters a chamber 105 at a first input mechanism 110. Cells are illustrated as circles. The cells pass through chamber 105, which comprises a matrix of posts 115, shown here as rectangular structures distributed along lines having a slope. As the cells pass in between the diagonally oriented rows of posts in the chamber, the cells are deflected laterally towards a side of the chamber. Similar to FIG. 3L, the chamber has a floor 160 (not shown) and an optional ceiling 150, which may be of the same material as the posts 115 or a different material.

In this example, a second input mechanism 112 is present in this system. A second solution (e.g., a buffer, which is different from the first solution entering the chamber through the first input mechanism 110) enters the chamber through the second input mechanism 112, for example buffer from buffer tube 577. In some embodiments, the first solution and the second solution do not substantially mix, and thus, the upper region of the chamber 155 comprises the first solution and has little if any of the second solution, while the lower region of the chamber 165 comprises the second solution and has little if any of the first solution. Thus, as the cells are deflected laterally and exit the chamber through output mechanism 122, the solution that exits the chamber via output mechanism 122 is in the second solution buffer.

Figure 3U:
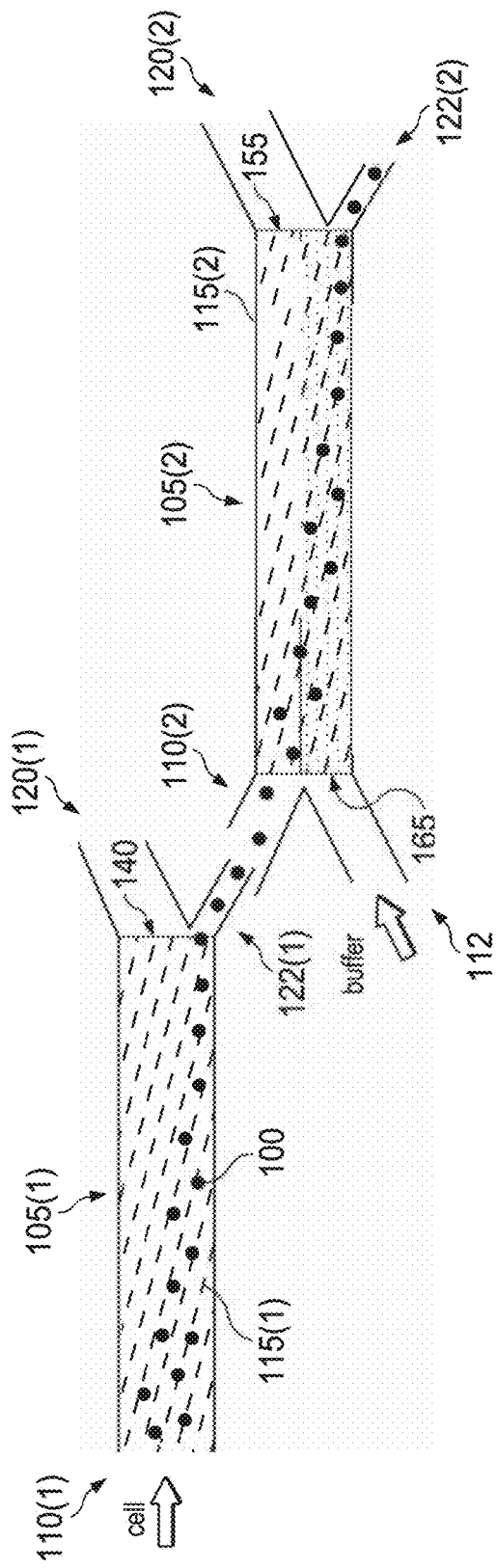
FIG. 3U illustrates an example microfluidics device having two separate chambers, one chamber for cell sorting and another chamber for buffer change according to some embodiments provided herein.

In some aspects, buffer changes may occur sequentially, in a cascade design, as shown in FIG. 3U. In this example, a first solution comprising cells 100 enters a first chamber 105(1) at a first input mechanism 110(1). Cells are illustrated as circles. The cells pass through chamber 105(1), which comprises a matrix of posts 115(1), shown here as rectangular structures distributed along lines having a slope. As the cells pass in between the diagonally oriented rows of posts in the chamber, the cells are deflected laterally. Similar to FIG. 3L, the chamber has a floor (160) (not shown) and an optional ceiling (150), which may be of the same material as the posts 115 or a different material. The cells (enriched) exit the chamber through output 122(1), which flows into input mechanism 110(2), where a second input mechanism 112 enters the system.

A second solution (e.g., a buffer), which is different from the first solution entering the chamber through the first input mechanism 110(1), enters the chamber through the second input mechanism (112). In some embodiments, the first solution and the second solution do not substantially mix, and thus, the upper region of the chamber (155) comprises the first solution and has little if any of the second solution, while the lower region of the chamber (165) comprises the second solution and has little if any of the first solution. The cells (enriched and in the buffer from input mechanism 112) exit chamber 105(2) through output mechanism 122(2).

In other aspects, buffer changes may occur in parallel. For example, the flow path may be divided so that the sample flows into multiple chambers, wherein each chamber includes an input mechanism for a buffer. With this configuration, the same buffer may be supplied to each of the parallel chambers, such that the cells are concentrated into the same buffer. Alternatively, each of the parallel chambers may be supplied with a different buffer, such that the cells are concentrated into different buffers, e.g., for different downstream assays.

In general, the input mechanism can be driven by a syringe pump or by manual depression of a syringe. In some aspects, for multiple inputs, one or more syringe pumps can be used to drive each input in an automated manner. In other aspects, for multiple inputs, manual depression of one or more syringes can be used to drive each input manually.

Figure 3V:
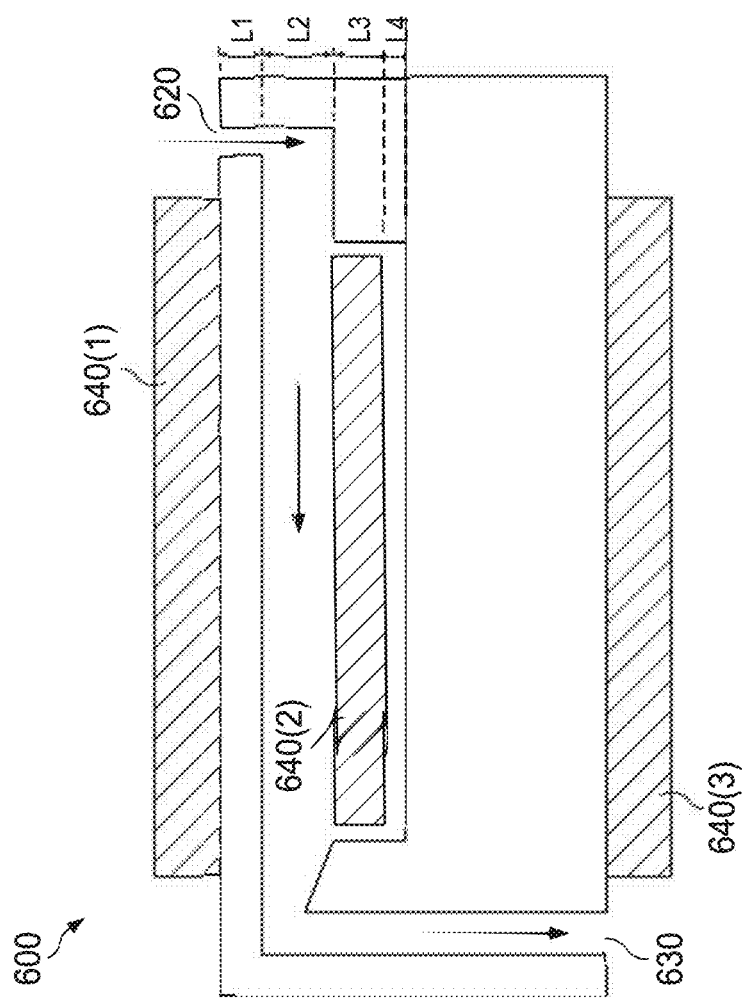
FIGS. 3V and 3W show alternative configurations of an electroporation apparatus according to some embodiments provided herein.

In any embodiment, an electroporation apparatus capable of providing different electroporation effects is described herein. For example, as illustrated in FIG. 3V, an electroporation device 600 having three electrodes 640(1), 640(2), 640(3) is provided. The electroporation device 600 includes two paths for cells and cargo to travel, a first path between electrode 640(1) and electrode 640(2) and a second path between electrode 640(2) and electrode 640(3) where the arrows indicate flow of cells. The cells can enter an electroporation chamber at inlet 620 and exit via outlet 630. Although not shown, it is contemplated herein that more than one outlet may be present, for example, each outlet can collect different types of cells.

Different electrode gap lengths (L1, L2, L3, L4) are present in the electroporation device 600. The different electrode gap lengths and different paths result in a different capacitance; therefore, different electric field strength and electroporation effect can be achieved for the cells traveling in each path. For example, L2 can be greater than L4, and in such instance, a capacitance (C1) in the first path can be greater than a capacitance (C2) in the second path (C1>C2). In any embodiment, cells (the same or different types) may be pre-sorted and/or selected, for example, using the microfluidics devices described above, to enter the first path or the second path.

Figure 3W:
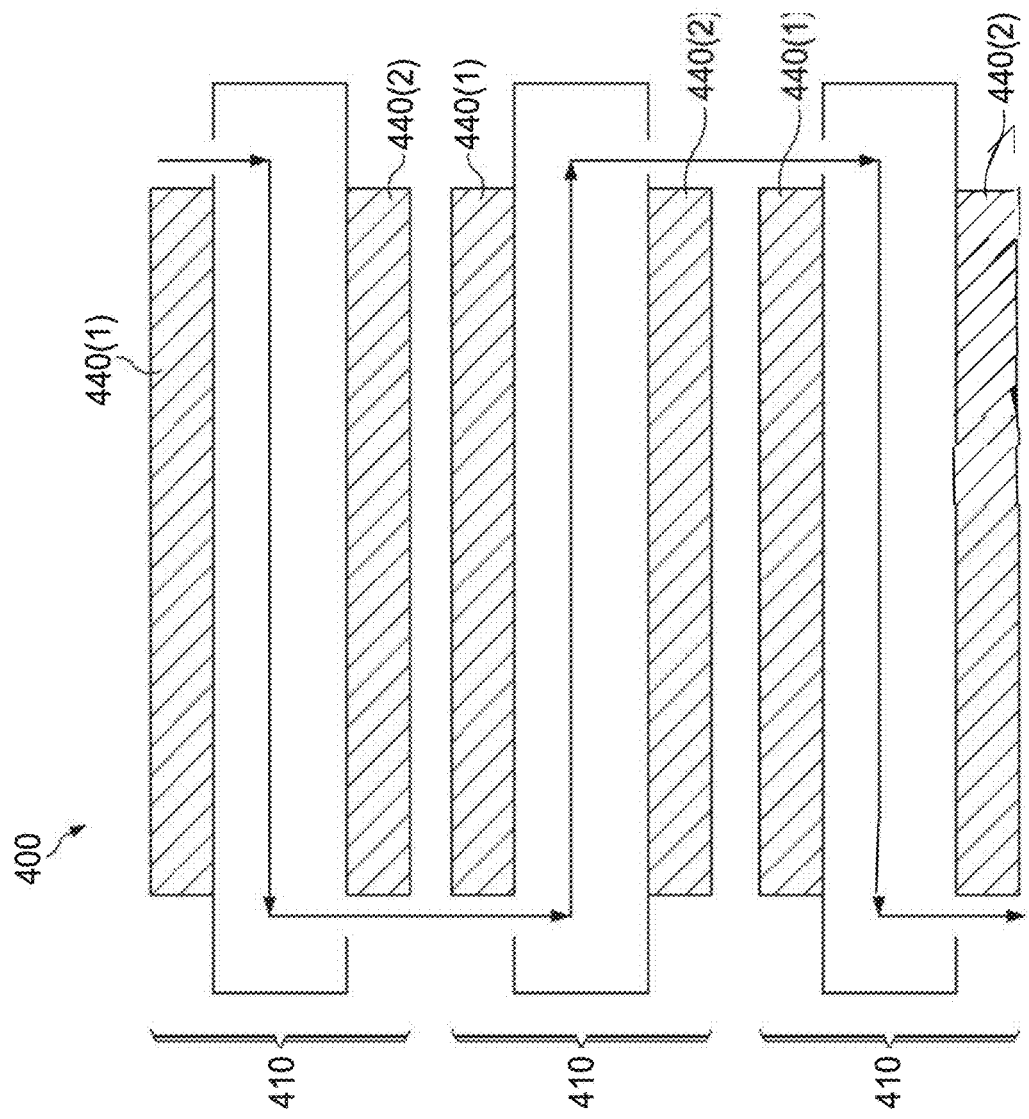

It is also contemplated herein that the electroporation devices described herein can be present as cartridges, which may be in fluid communication with one another (e.g., connected, stacked), to provide a path of desired length and geometry. For example, as illustrated in FIG. 3W, cartridges 410 each include an electroporation chamber including a first electrode 440(1) and a second electrode 440(2), wherein the cartridges may be stacked in series with the arrows showing flow of cells through the cartridges. For example, an outlet of topmost cartridge 410 is in fluid communication with an inlet of middle cartridge 410 and an outlet of middle cartridge 410 is in fluid communication with an inlet of lowermost cartridge 410.

Figure 3X:
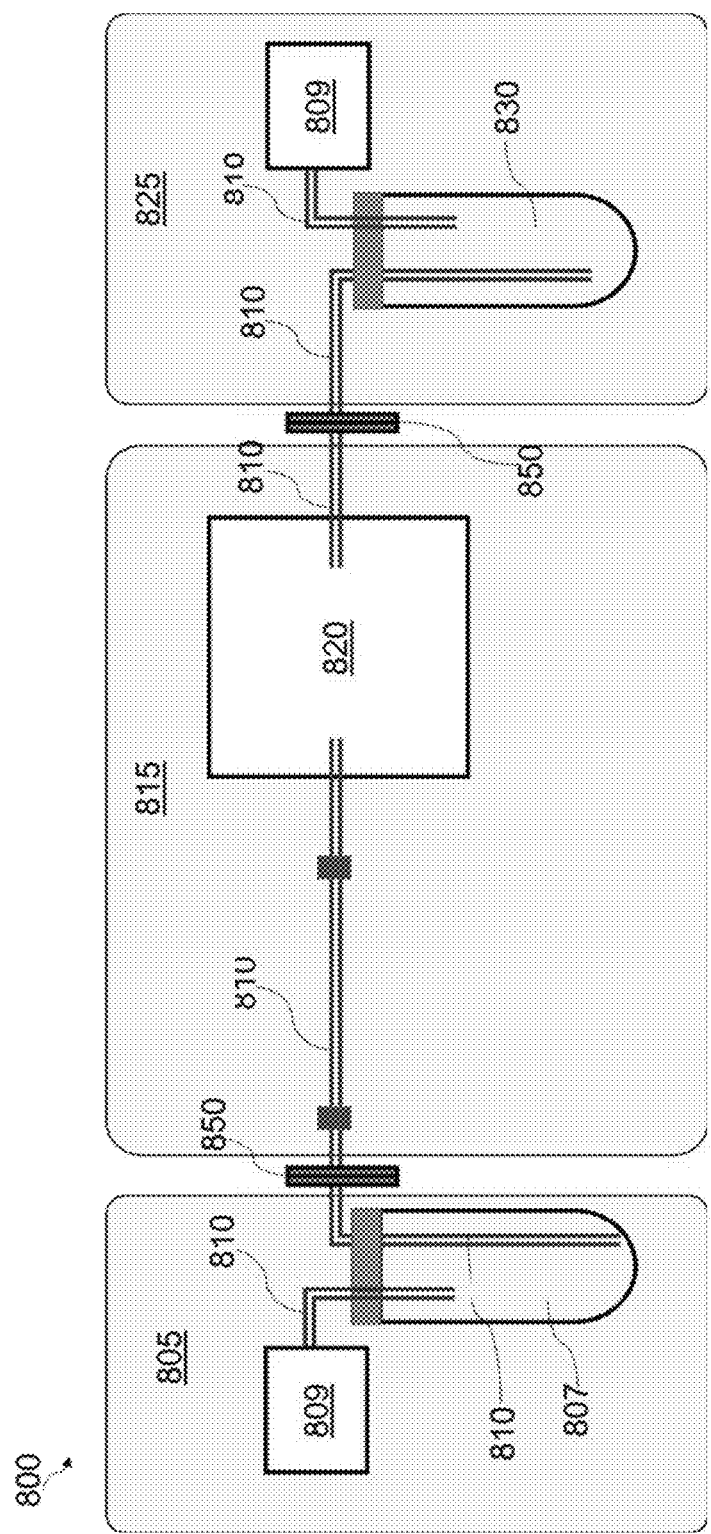
FIG. 3X shows a modular configuration of an electroporation system including an electroporation apparatus according to some embodiments provided herein.

In further embodiments, a modular system is provided including the electroporation devices described herein. For example, as illustrated in FIG. 3X, a modular system 800 includes three modules, first module 805, second module 815, and third module 825, which are configured to fluidly communicate or connect with one another. First module 805 includes a first container 807 (e.g., sample tube) for containing cells and/or cargo for transfection as well as tubing 810 for fluidly connecting the first container 807 with the second module 815. First module 805 may also optionally include an air filter device 809 and tubing 810 for fluidly connecting the air filter device 809 to the first container 807. Second module 815 includes electroporation device 820 and tubing 810 for fluidly connecting the electroporation device with the first module 805, e.g., the first container 807, and the second module 825 as well as tubing 810 for fluidly connecting a flow generating means as described herein (e.g., a peristaltic pump) with the electroporation device 820 and first module 805, e.g., the first container 807. Third module 825 includes a second container 830 (e.g. collection tube) for collecting the electroporated cells as well as tubing 810 for fluidly connecting the second container 830 with the second module 815, e.g., the electroporation device 820. Third module 825 may also optionally include an air filter device 809 and tubing 810 for fluidly connecting the air filter device 809 to the second container 830. Optionally, a connector 850, such as a luer lock, may connect the modules together, for example, the first module 805 with the second module 815 and the second module 815 with the third module 825. It is contemplated herein that the first module 805, the second module 815, and the third module 825 may each be packaged and sterilized separately.

Figure 1A:
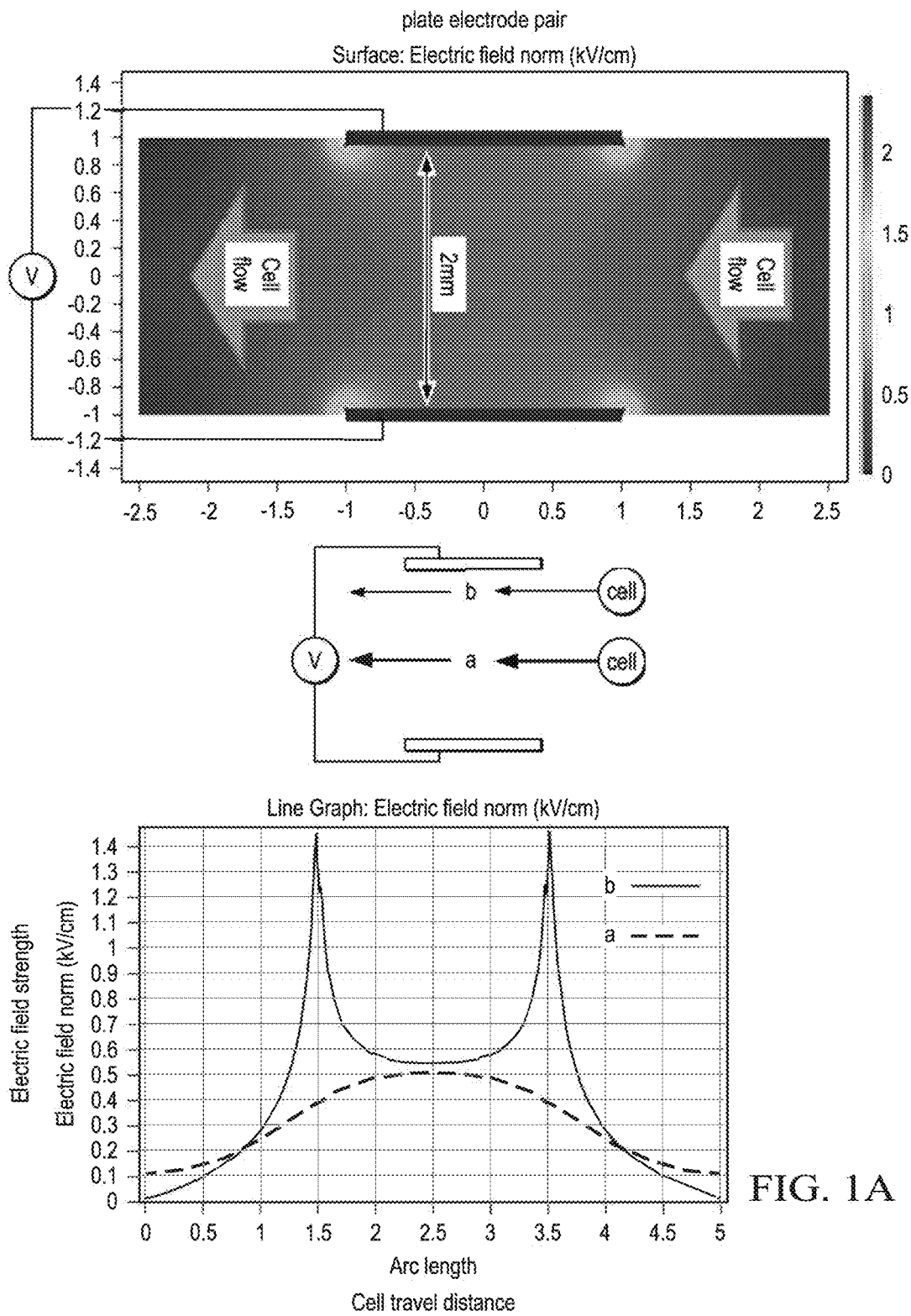
FIGS. 1A and 1B show conventional electroporation devices including parallel plate electrodes (as shown in FIG. 1A) and micromesh electrodes with no offset between the input and the output (as shown in FIG. 1B).
Figure 1B:
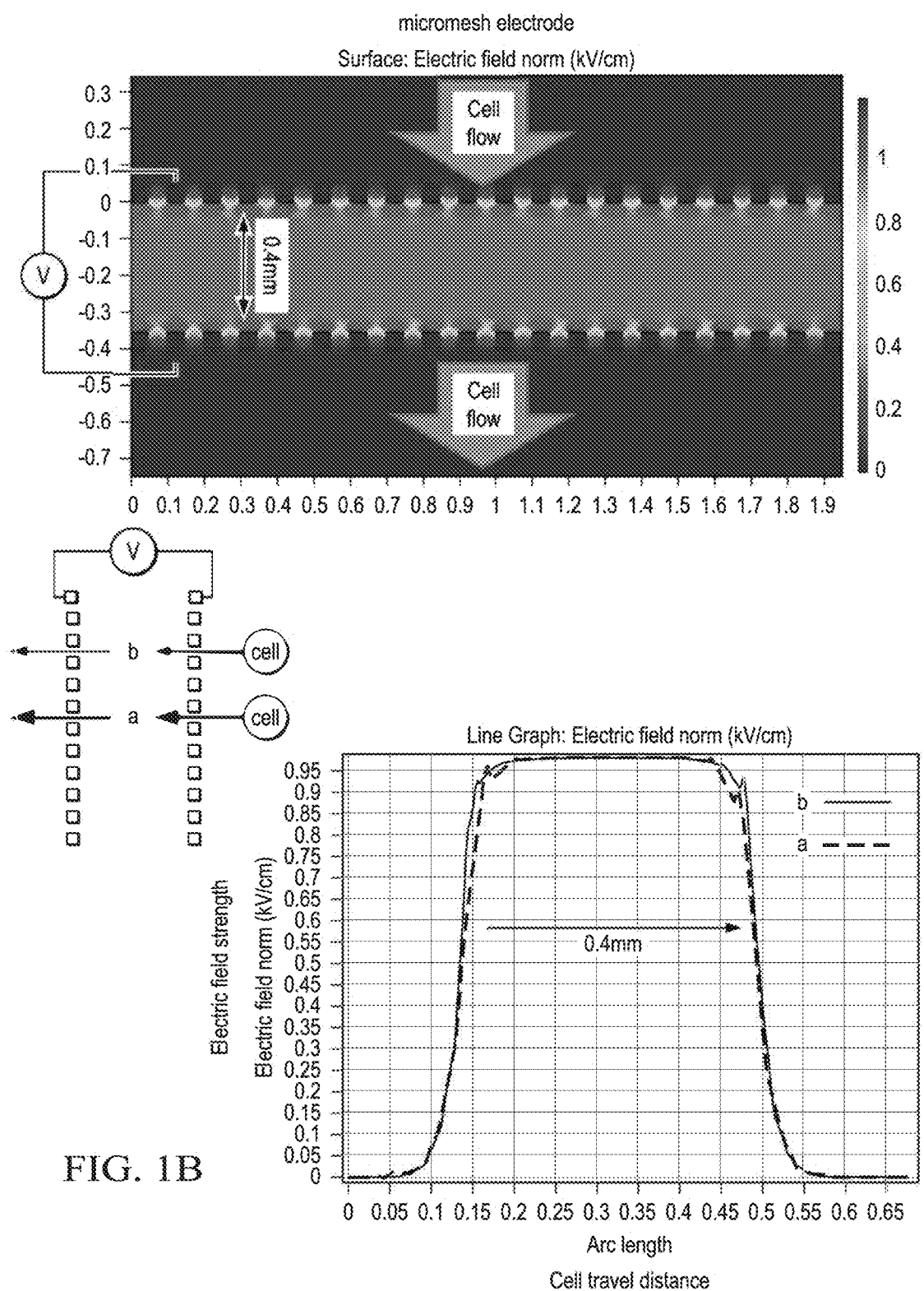

The electroporation apparatuses described herein have a number of advantages over mesh-based electroporation devices, such as the configuration shown in FIG. 1B. First, the traveling distance through the electroporation chamber, as measured from first input to the first output of the electroporation chamber, may be increased without leading to a corresponding increase in the electric field. Thus, cells are exposed to a uniform electric field for a greater length of time than in a strictly linear flow path, which leads to improved electroporation efficiency, without a corresponding decrease in viability.

Although the electroporation chamber width (w) between the upper mesh electrode and the lower mesh electrode could be increased in FIG. 1B to provide a longer traveling distance, a larger electroporation chamber width would have a larger impedance, and a higher voltage would need to be applied to generate a suitable electric field. Additionally, the larger voltage would likely have an adverse impact on cellular viability. Further, for parallel plate electrode configurations, as in FIG. 1A, the electric field distribution would not be uniform.

Thus, according to embodiments, the electroporation apparatuses described herein can have a shorter electrode pair due to the offset input output design, which extends the electroporation chamber length without increasing the electrode pair distance.

FIG. 4 provides a table illustrating differences between an electroporation device as described herein and electroporation devices in the prior art. Such differences include, but are not limited to: (1) presence of the input output offset distance, (2) use of a low conductance low osmolarity electroporation media, instead of commercially available electroporation media such as BTX and RPMI, (3) exponentially discharging waveforms, applied in a series of electrical pulses, and (4) a stepping fluid flow scheme.

Figure 6:
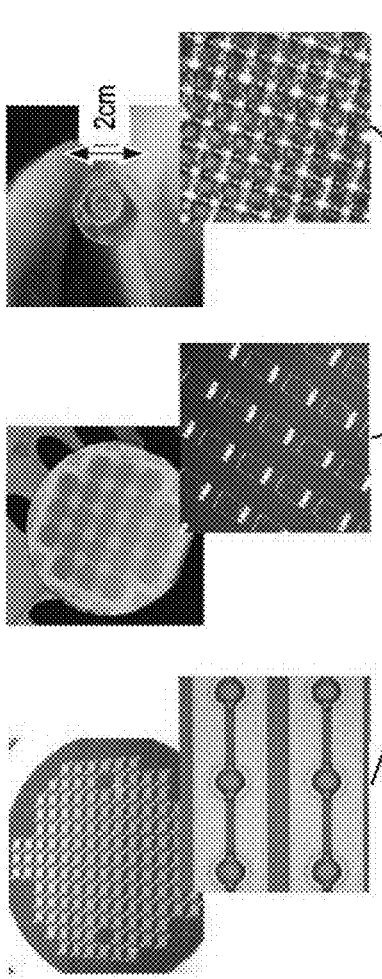
FIG. 6 shows various examples of micromeshes formed of different materials suitable for use with a chamber offset electroporation device, according to some embodiments provided herein.

While the example in FIGS. 3A-3C utilizes stainless steel micromesh electrodes, the electrodes are not limited to any particular material and may be formed of any suitable material. For example and as shown in FIG. 6, suitable material include silicon and polyimide. Silicon and polyimide may be used to form suitable micromesh electrodes, however, such materials are typically processed in clean room facilities using microfabrication protocols known in the art. In contrast, stainless steel micromesh electrodes are easy to set up and do not require specialized facilities, such as clean rooms.

It is understood that any suitable material may be used provided that the micromesh has pores allowing passage of cells (e.g., the micromesh pores are larger than the cells), and that the micromesh pores are compatible with electrode patterning around the pore opening.

Electroporation Methods and Parameters

Methods of electroporating cells with a cargo are provided herein, for example, with the electroporation apparatuses as described above. The methods can include flowing the cells with the cargo into an electroporation chamber. The electroporation chamber includes a first electrode (e.g., a solid electrode), a second electrode (e.g., a solid electrode), and a fluid channel region having a path defined therein between a first electrode and a second electrode, all as described herein. The apparatus also includes a first input allowing passage of the cells and cargo into the electroporation chamber as described herein, and a first output allowing passage of electroporated cells from the electroporation chamber as described herein. In some embodiments, the first input and the first output can be separated by an offset distance. The cells can be suspended in an electroporation medium. The first electrode can be bounded by a first material as described herein and the second electrode can be bounded by a second material as described herein, and may be the same or different. The first material and the second material may also include a first outer input as described herein and first outer output as described herein.

In some embodiments, the electroporation chamber includes an upper micromesh electrode as described herein, a lower micromesh electrode as described herein, and a path defined between the upper micromesh electrode and the lower micromesh electrode for the cells and the cargo to flow as described herein. The upper micromesh electrode and the lower micromesh electrode each have a porosity as described herein. Additionally, the upper micromesh electrode can be bounded by a first material as described herein. The first material can include a first input as described herein allowing passage of cells into the electroporation chamber. The lower micromesh electrode can be bounded by a second material. The second material can include a first output as described herein allowing passage of electroporated cells from the electroporation chamber. The first input and the first output are separated by an offset distance as described herein. The cells can be suspended in an electroporation medium. Optionally, the upper micromesh electrode may further include a second input as described herein and/or the lower micromesh electrode may further include a second output as described herein.

Figure 5:
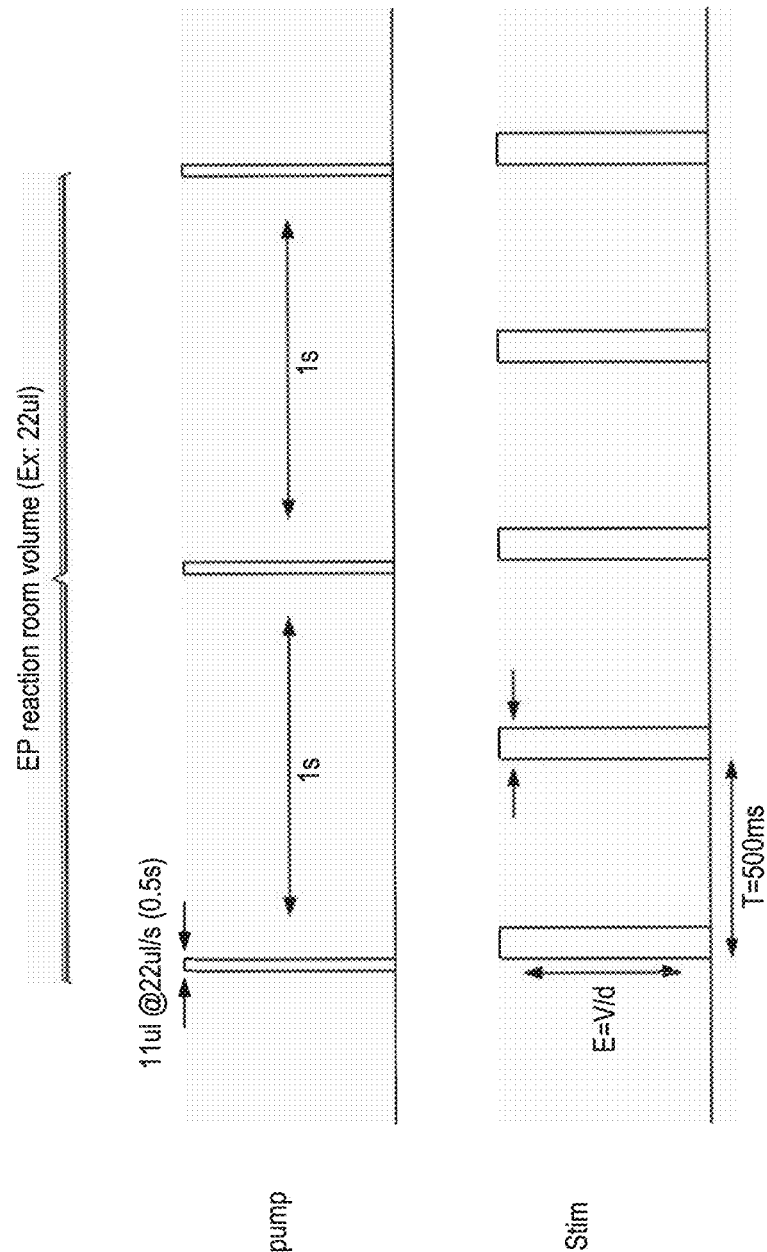
FIG. 5 shows examples of fluid flow waveforms (pump) and electric waveforms (stim) that may be applied to cells flowing through the chamber offset electroporation device, according to some embodiments provided herein.

In any embodiment, flowing of the cells and cargo may be performed in a stepwise manner. For example, a fluid volume of greater than or equal to about half a total volume of the electroporation chamber can be pumped into the electroporation chamber at a designated interval of time. In some embodiments, a fluid volume about equal to the total volume of the electroporation chamber can be pumped into the electroporation chamber. FIG. 5 shows an example series of electrical pulses (stim) and an example stepping fluid flow scheme (pump). For the stepping fluid flow scheme, the chamber volume is approximately 22 µL. Every second, 11 µL is pumped into the electroporation chamber, displacing half the volume. This may be repeated as long as needed to process a desired amount of cells.

Additionally or alternatively, any suitable interval of time may be used along with any suitable volume for the stepping fluid flow scheme. For example, the interval of time may range from about 0.1 seconds to about 10 seconds, from about 0.5 seconds to about 5 seconds, from about 1 second to about 2 seconds, or any period of time in between, or may include longer intervals. In some aspects, the amount of fluid pumped into the electroporation chamber as a function of time may be three-fourths the volume of the input chamber, one-half the volume of the electroporation chamber, one-fourth the volume of the electroporation chamber, one-eighth the volume of the electroporation chamber, or smaller. Any suitable flow rate of the cells and the cargo can be used along with the parameters described herein. For example, a flow rate of cells and cargo in an electroporation medium may be greater than or equal to about 0.1 ml/min, greater than or equal to about 0.5 ml/min, greater than or equal to about 1 ml/min, greater than or equal to about 2.5 ml/min, greater than or equal to about 5 ml/min, greater than or equal to about 7.5 ml/min, greater than or equal to about 10 ml/min, greater than or equal to about 12.5 ml/min, or about 15 ml/min, or from about 0.1 ml/min to about 15 ml/min, about 0.5 ml/min to about 15 ml/min, about 1 ml/min to about 15 ml/min, about 1 ml/min to about 12.5 ml/min, about 1 ml/min to about 10 ml/min, about 1 ml/min to about 7.5 ml/min, about 1 ml/min to about 5 ml/min, or about 1 ml/min to about 2.5 ml/min.

In any embodiment, the cells are exposed to a uniform or a substantially uniform electrical field within the electroporation chamber. Multiple electrical pulses can be applied to the cells within the electroporation chamber, wherein each electrical pulse is the same or different. In some embodiments, a direct current (DC) electrical pulse is applied. Additionally or alternatively, an alternating current (AC) electrical pulse is applied. In any embodiment, each pulse can have a form of an exponentially discharging waveform or a square waveform. In any embodiments, the multiple electrical pulses can include both an exponentially discharging waveform or a square waveform.

For the series of electrical pulses, every 100 ms to 5000 ms (e.g., every 100 ms, every 250 ms, every 500 ms, every 1000 ms, every 2000 ms, every 3000 ms, etc), a voltage can be applied to the electrodes to generate an electric field of a given strength. This may be repeated as long as needed to process a desired amount of cells. Accordingly, while aspects may be referred to as continuous flow, it is understood that continuous flow includes a stepping fluid flow scheme, in which fluid is continually pumped into the electroporation chamber according to a defined time interval.

Additionally or alternatively, any suitable time duration between electrical pulses may be used along with any suitable duration of electrical pulse for cells in the electroporation chamber. For example, the a time duration between each pulse may range from about 0.1 seconds to about 15 seconds, from about 0.1 seconds to about 10 seconds, from about 0.1 seconds to about 5 seconds, from about 0.2 seconds to about 1 second, from about 0.4 seconds to about 0.6 seconds, or any period of time in between, and may include longer intervals. In some aspects, the duration of the electrical pulse may range from about 10 ms to about 10 s, from about 10 ms to about 5 s, from about 10 ms to about 1 s, from about 10 ms to about 500 ms, from about 10 ms to about 250 ms, from about 50 ms to about 150 ms, from about 75 ms to about 125 ms, from about 100 ms to about 10 s, from about 100 ms to about 5, from about 100 ms to about 1 s, from about 100 ms to about 500 ms, from about 100 ms to about 250 ms, or any range in between.

With respect to suitable pulse numbers and pulse-to-pulse intervals, at least two, three, four, five, six, seven, eight, nine or ten pulses may provide more desirable results than a single pulse. Therefore, it is contemplated that pulses may range from 2-10 pulses, 2-6 pulses, 6-8 pulses, or 2-3 pulses. Most typically, the pulses are separated from subsequent pulses by a relatively short interval, typically between 0.5 second and 15 seconds, though in some cases even longer intervals may be used.

In any embodiment, multiple electrical pulses may be applied at a suitable voltage to produce a field strength of about 0.1 kV/cm to about 5 kV/cm, about 0.1 kV/cm to about 3 kV/cm, about 0.1 kV/cm to about 2 kV/cm, about 0.1 kV/cm to about 1 kV/cm, about 0.1 kV/cm to about 0.5 kV/cm, about 0.3 kV/cm to about 5 kV/cm, about 0.3 kV/cm to about 3 kV/cm, about 0.3 kV/cm to about 2 kV/cm, about 0.3 kV/cm to about 1 kV/cm, about 0.3 kV/cm to about 0.5 kV/cm, about 0.5 kV/cm to about 3 kV/cm, about 0.5 kV/cm to about 2 kV/cm, about 0.5 kV/cm to about 1 kV/cm, about 0.8 kV/cm to about 3 kV/cm, about 0.8 kV/cm to about 2 kV/cm, about 0.8 kV/cm to about 1 kV/cm, about 1 kV/cm to about 3 kV/cm, or about 1 kV/cm to about 2 kV/cm. Suitable voltages may be about 10 V, about 15 V, about 20

V, about 30 V, about 40 V, about 50 V, about 75 V, about 100 V, or about 200 V, or from about 10 V to about 200 V, about 10 V to about 100 V, about 10 V to about 75 V, about 10 V to about 50, about 10 V to about 40 V, about 10 V to about 30 V, about 15 V to about 200 V, about 15 V to about 100 V, about 15 V to about 75 V, about 15 V to about 50, about 15 V to about 40 V, about 15 V to about 30 V, about 20 V to about 50, about 20 V to about 40 V, about 20 V to about 30 V, about 30 V to about 50 V, about 30 V to about 40 V, or any suitable range therein.

Additionally or alternatively, each electrical pulse can have a pulse width of greater than or equal to about 10 µs, greater than or equal to about 50 µs, greater than or equal to about 75 µs, greater than or equal to about 100 µs, greater than or equal to about 250 µs, greater than or equal to about 500 µs, greater than or equal to about 750 µs, greater than or equal to about 1,000 µs, greater than or equal to about 5,000 µs, or about 10,000 µs; or from about 10 µs to about 10,000 µs, about 10 µs to about 5,000 µs, about 10 µs to about 1,000 µs, about 10 µs to about 750 µs, about 10 µs to about 500 µs, about 10 µs to about 250 µs, about 10 µs to about 100 µs, about 10 µs to about 50 µs, about 100 µs to about 1000 µs, about 100 µs to about 750 µs, about 100 µs to about 500 µs, about 100 µs to about 250 µs, about 250 µs to about 1000 µs, about 250 µs to about 750 µs, about 250 µs to about 500 µs, about 500 µs to about 1000 µs, or about 500 µs to about 750 µs.

Any suitable cell may be transfected, for example, mammalian cells, nonmammalian cells or both, with a cargo. Examples of suitable mammalian cells include, but are not limited to NK cells (e.g., haNK cells, primary NK cells, activated (aNK) cells), EC-7 cells (a derivative of HEK 293 cells, modified to produce adenovirus), T cells (e.g., primary CD4/CD8 T cells), CHO-S cells, dendritic cells, embryonic cells, stem cells (e.g., adipose-derived mesenchymal stem cells (AD-MSCs)), epithelial cells, lymphocytes, macrophages, gamete cells, and fibroblasts. Examples of suitable nonmammalian cells include, but are not limited to bacteria cells, and yeast cells. Any suitable cargo may be used, for example, a nucleic acid. The nucleic acid may be an RNA e.g., synthetic RNA, mRNA, in vitro transcribed RNA, GFP-mRNA, etc.) and/or a DNA (e.g., synthetic DNA, GFP-DNA, plasmid DNA, etc.) In particular, NK cells, EC-7 cells (a derivative of HEK 293 cells, modified to produce adenovirus) and T cells can be transfected with RNA (e.g., synthetic RNA, mRNA, in vitro transcribed RNA, GFP-mRNA, etc.) and/or DNA (e.g., synthetic DNA, GFP-DNA, plasmid DNA, etc.) using the electroporation apparatuses described herein. It is also contemplated herein that the electroporation apparatuses described herein could be used to perform in vitro fertilization. For example, an egg and sperm can flow through an electroporation device as described herein to achieve fertilization of the egg.

In further contemplated aspects, the medium or electroporation buffer in which the cells are transfected is a low conductivity and low osmolarity medium, optionally containing one or more nutrients. In any embodiment, the electroporation medium can have a conductance of greater than or equal to about 0.05 mS/m, greater than or equal to about 1 mS/m, greater than or equal to about 5 mS/m, greater than or equal to about 10 mS/m, greater than or equal to about 15 mS/m, greater than or equal to about mS/m, greater than or equal to about 25 mS/m, greater than or equal to about 30 mS/m, greater than or equal to about 50 mS/m, greater than or equal to about 100 mS/m, greater than or equal to about 150 mS/m, or 200 mS/m; or from about 0.05 mS/m to about 200 mS/m; about 1 mS/m to about 30 mS/m, about 1 mS/m to about 20 mS/m, about 1 mS/m to about 10 mS/m, about 1 mS/m to about 5 mS/m, about 3 mS/m to about 30 mS/m, about 5 mS/m to about 20 mS/m, or about 5 mS/m to about 15 mS/m. Additionally or alternatively, the electroporation medium may have an osmolarity of greater than or equal to about 50 mOsm/l, greater than or equal to about 100 mOsm/l, greater than or equal to about 150 mOsm/l, greater than or equal to about 200 mOsm/l, greater than or equal to about 250 mOsm/l, greater than or equal to about 300 mOsm/l, greater than or equal to about 350 mOsm/l, or about 400 mOsm/l; or from about 50 mOsm/l to about 400 mOsm/l, about 50 mOsm/l to about 300 mOsm/l, about 50 mOsm/l to about 200 mOsm/l, about 100 mOsm/l to about 400 mOsm/l, about 100 mOsm/l to about 300 mOsm/l, about 200 mOsm/l to about 400 mOsm/l, about 200 mOsm/l to about 300 mOsm/l, about 250 mOsm/l to about 400 mOsm/l, or about 250 mOsm/l to about 300 mOsm/l.

In any embodiment, the electroporation medium may include one or more salts, a sugar, and a buffering agent. Suitable salts include, but are not limited to a metal halide salt, a phosphate salt, a metal sulfate salt, and combinations thereof. Examples of suitable metal halide salts include, but are not limited to potassium chloride (KCl), sodium chloride (NaCl), lithium chloride (LiCl), calcium chloride ($CaCl_2$), chromium chloride ($CrCl_3$), potassium bromide (KBr), sodium bromide (NaBr), magnesium chloride ($MgCl_2$), magnesium bromide ($MgBr_2$), magnesium fluoride ($MgF_2$), magnesium iodide ($MgI_2$) lithium bromide (LiBr), potassium iodide (KI), sodium iodide (NaI), and lithium iodide (LiI). Examples of suitable phosphate salts include, but are not limited to monosodium phosphate ($NaH_2PO_4$), disodium phosphate ($Na_{-2}HPO_4$), trisodium phosphate ($Na_3PO_4$), monomagnesium phosphate ($Mg(H_2PO_4)_2$), dimagnesium phosphate ($MgHPO_4$), trimagnesium phosphate ($Mg_3(PO_4)_2$), monopotassium phosphate ($KH_2PO_4$), dipotassium phosphate ($K_2HPO_4$), tripotassium phosphate ($K_3PO_4$), monocalcium phosphate ($Ca(H_2PO_4)_2$), dicalcium phosphate ($CaHPO_4$), tricalcium phosphate ($Ca_3(PO_4)_2$), and chromium phosphate ($CrPO_4$). Examples of suitable metal sulfate salts include, but are not limited to sodium sulfate ($Na_2SO_4$), magnesium sulfate ($MgSO_4$), potassium sulfate ($K_2SO_4$), calcium sulfate ($CaSO_4$), and chromium sulfate ($Cr_2(SO_4)_3$). In some embodiments, the one or more salts may be potassium chloride, magnesium chloride, disodium phosphate, monopotassium phosphate, magnesium sulfate, and combinations thereof.

Examples of suitable sugars include a monosaccharide, a disaccharide, or a combination thereof. Suitable monosaccharides include, but are not limited to glucose, fructose, and galactose. Suitable disaccharides include, but are not limited to disaccharides formed from two of glucose, fructose, and galactose. For example, a suitable disaccharide can be sucrose, lactose, maltose, terhalose, or a combination thereof. Examples of suitable buffering agents include, but are not limited to HEPES, tris(hydroxymethyl), and PBS (phosphate buffered saline).

In any embodiment, each of the one or more salts may be present in the electroporation medium in a concentration of about 0.1 mM to about 200 mM, about 0.1 mM to about 150 mM, about 0.1 mM to about 100 mM, about 0.1 mM to about 80 mM, about 0.1 mM to about 60 mM, about 0.1 mM to about 40 mM, about 0.1 mM to about 20 mM about 0.1 mM to about 10 mM, about 1 mM to about 20 mM, or about 1 mM to about 10 mM. For example, salts such as $KH_2PO_4$, $Na_2HPO_4$, and $MgSO_4$, can each be present in the electroporation medium in a concentration of about 0.1 mM to about 20 mM. A sugar may be present in the electroporation medium in a concentration of about 20 mM to about 300 mM, about 20 mM to about 200 mM, or about 40 mM to about 200 mM. The buffering agent may be present in the electroporation medium in a concentration of about 1 mM to about 100 mM, about 10 mM to about 50 mM, or about 15 mM to about 30 mM.

Other suitable media include but are not limited to: Cw100 (0.11 S/m, 0.12 osm/l) or Cw240, as shown in Table 1. Commercially available electroporation media may be utilized, but was shown to be suboptimal. Such commercially available media include: RPMI (1.375/m, 0.28 osm/l), BTX (8 mS/m, 0.27 osm/l), DMEM(Dulbecco's Modified Eagle Medium), diluted PBS, or PBS with or without HEPES. The media are generally electrically conductive media and may also be sterile.

TABLE 1

Composition of electroporation media

| | $KH_2PO_4$ | $Na_2HPO_4$ | $MgSO_4$—$7H_2O$ | Sucrose | HEPES |
|---|---|---|---|---|---|
| Cw240 | 2 mM | 5 mM | 1 mM | 200 mM | 15 mM |
| Cw100 | 2 mM | 0 mM | 1 mM | 99 mM | 20 mM |

In any embodiment, the cells for electroporation may be present in the electroporation medium in a cell density of greater than or equal to about $1 \times 10^6$ cells/ml, greater than or equal to about $10 \times 10^6$ cells/ml, greater than or equal to about $50 \times 10^6$ cells/ml, greater than or equal to about $100 \times 10^6$ cells/ml, greater than or equal to about $150 \times 10^6$ cells/ml, greater than or equal to about $200 \times 10^6$ cells/ml, greater than or equal to about $250 \times 10^6$ cells/ml, greater than or equal to about $300 \times 10^6$ cells/ml, greater than or equal to about $400 \times 10^6$ cells/ml or about $500 \times 10^6$ cells/ml; or from about $1 \times 10^6$ cells/ml to about $300 \times 10^6$ cells/ml, about $1 \times 10^6$ cells/ml to about $250 \times 10^6$ cells/ml, about $1 \times 10^6$ cells/ml to about $200 \times 10^6$ cells/ml, about $1 \times 10^6$ cells/ml to about $150 \times 10^6$ cells/ml, about $1 \times 10^6$ cells/ml to about $100 \times 10^6$ cells/ml, about $1 \times 10^6$ cells/ml to about $50 \times 10^6$ cells/ml, about $1 \times 10^6$ cells/ml to about $300 \times 10^6$ cells/ml, about $1 \times 10^6$ cells/ml to about $250 \times 10^6$ cells/ml, about $10 \times 10^6$ cells/ml to about $200 \times 10^6$ cells/ml, about $10 \times 10^6$ cells/ml to about $150 \times 10^6$ cells/ml, about $10 \times 10^6$ cells/ml to about $100 \times 10^6$ cells/ml, about $10 \times 10^6$ cells/ml to about $50 \times 10^6$ cells/ml, about $100 \times 10^6$ cells/ml to about $300 \times 10^6$ cells/ml, about $100 \times 10^6$ cells/ml to about $250 \times 10^6$ cells/ml, about $100 \times 10^6$ cells/ml to about $200 \times 10^6$ cells/ml, or about $100 \times 10^6$ cells/ml to about $150 \times 10^6$ cells/ml.

With respect to suitable capacitances, it is contemplated that the capacitance may range from about 1 µF to about 150 µF. In some embodiments, the capacitance may range from about 1-100 µF, from about 5 to about 75 µF, from about 5 to about 50 µF, from about 10 to about 40 µF, or from about 10 to about 30 µF, or from about 10 to about 25 µF. In other embodiments, the capacitance is about 10 µF.

In some embodiments, multiple electrical pulses, along with a corresponding short time constant may be utilized. In some aspects, a time constant of less than 30 msec, less than 20 msec, less than 10 msec, or less than 5 msec may be used. In other aspects, a time constant may range from about 0.5 to 30 msec, from about 1 to 20 msec, and from about 5 to 15 msec; or about 10 msec.

In some aspects, the electrical field strength for electroporation is between about 0.3-3 kV/cm. Lower electrical field strengths (e.g., about 0.5-1 kV/cm) were found to be suitable for EC-7 cells, while higher electrical field strengths (e.g., about 1-3 kV/cm) were found to be suitable for hank cells. In general, electrical field strengths for electroporation ranging from about 0.1 to about 5 kV/cm are contemplated herein. The voltage may be selected to generate suitable electrical field strengths.

In general, the impedance (Rp) may range from about 200Ω up to infinity, or in other cases, from about 200Ω up to about 1 k.

The concentration of cargo added to the electroporation reaction, e.g., the material to be transported into the cell, has a concentration of greater than or equal to about 50 µg/ml, greater than or equal to about 100 µg/ml, greater than or equal to about 200 µg/ml, greater than or equal to about 300 µg/ml greater than or equal to about 400 µg/ml, or about 500 µg/ml; from about 50 µg/ml to about 500 µg/ml, about 50 µg/ml to about 400 µg/ml, about 50 µg/ml to about 300 µg/ml, about 50 µg/ml to about 200 µg/ml, about 50 µg/ml to about 100 µg/ml, about 100 µg/ml to about 500 µg/ml, about 100 µg/ml to about 400 µg/ml, about 100 µg/ml to about 300 µg/ml, or about 100 µg/ml to about 200 µg/ml. In some aspects, GFP-mRNA or GFP-DNA at a concentration of about 50 µg/ml, 60 µg/ml, 100 µg/ml, 200 µg/ml, 100-300 µg/ml, 50-100 µg/ml was added to the electroporation medium, while in other embodiments, dextran 500$k$ at a concentration of about 50 µg/ml was added to the electroporation reaction.

In some aspects, up to 7.33 uL/s at $4 \times 10^7$ cells/ml (13.2 mL ($5.28 \times 10^8$ cells) in 30 mins can be achieved in a single chamber device. To reach $20 \times 10^9$ cells in 30 mins, the cell density may be increased four-fold and/or parallel processing may be performed using multiple electroporation chambers.

In some aspects, and further to the examples provided below, electroporation electronics and parameters can be specifically designed for electroporation of NK cells (e.g., haNK cells, primary NK cells, activated (aNK) cells), EC7 cells, dendritic cells, CHO-S cells, T cells (e.g., primary CD4/CD8 T cells), and stem cells (e.g., AD-MSC cells).

In some embodiments, the cells are one or more of NK cells (e.g., haNK cells, primary NK cells, activated (aNK) cells), EC7 cells, dendritic cells, CHO-S cells, T cells (e.g., primary CD4/CD8 T cells), and stem cells (AD-MSC cells), and one or more of the electroporation parameters are as follows: (i) the field strength is applied at the voltage of about 20 V to about 50 V; (ii) the pulse width is about 10 µs to about 750 µs; and (iii) the cell density of the cells in the electroporation medium is about $5 \times 10^6$ cells/ml to about $300 \times 10^6$ cells/ml.

In some embodiments, the cells are EC-7 cells, the cargo is DNA, and one or more of the electroporation parameters are as follows: (i) the field strength is applied at the voltage of about 20 V to about 50 V, about 20 V to 40 V, or about 20 V to about 30 V; (ii) the pulse width is about 10 µs to about 100 µs, 10 µs to about 75 µs, or 10 µs to about 50 µs; (iii) number of pulses is 2-6 or 2-3 and (iv) the cell density of the cells in the electroporation medium is about $10 \times 10^6$ cells/ml to about $250 \times 10^6$ cells/ml, about $10 \times 10^6$ cells/ml to about $100 \times 10^6$ cells/ml, or about $50 \times 10^6$ cells/ml to about $100 \times 10^6$ cells/ml. Additionally or alternatively, the electroporated EC-7 cells with DNA cargo can have a viability of at least about 60%, at least about 70%, or at least about 80% with a transfection efficiency of at least about 70%, at least about 80%, or at least about 95%.

In some embodiments, the cells are CHO-S cells, cargo is DNA, and one or more of the electroporation parameters are as follows: (i) the field strength is applied at the voltage of about 20 V to about 50 V, or about 30 V to 50

V, about 40 V to about 50 V; (ii) the pulse width is about 100 µs to about 750 µs, about 250 µs to about 750 µs, or about 500 µs to about 750 µs; (iii) number of pulses is 2-6 or 2-3 and (iv) the cell density of the cells in the electroporation medium is about $50\times10^6$ cells/ml to about $250\times10^6$ cells/ml, about $50\times10^6$ cells/ml to about $125\times10^6$ cells/ml, or about $50\times10^6$ cells/ml to about $100\times10^6$ cells/ml. Additionally or alternatively, the electroporated CHO-S cells with DNA cargo can have a viability of at least about 60%, at least about 70%, at least about 80%, or at least about 90% with a transfection efficiency of at least about 70%, at least about 80%, or at least about 85%.

In some embodiments, the cells are T cells (e.g., primary CD4/CD8 T cells), the cargo is DNA or RNA, and one or more of the electroporation parameters are as follows: (i) the field strength is applied at the voltage of about 20 V to about 50 V, or about 30 V to 50 V, about 40 V to about 50 V; (ii) the pulse width is about 100 µs to about 750 µs, about 100 µs to about 500 µs, or about 200 µs to about 400 µs; (iii) number of pulses is 2-10 or 2-6 and (iv) the cell density of the cells in the electroporation medium is about $10\times10^6$ cells/ml to about $300\times10^6$ cells/ml, about $20\times10^6$ cells/ml to about $250\times10^6$ cells/ml, or about $10\times10^6$ cells/ml to about $200\times10^6$ cells/ml. Additionally or alternatively, the electroporated T cells (e.g., primary CD4/CD8 T cells) with DNA or RNA cargo can have a viability of at least about 60%, at least about 70%, at least about 80%, or at least about 90% with a transfection efficiency of at least about 20%, at least about 80%, at least about 90%, or at least about 99%.

In some embodiments, the cells are NK cells (e.g., haNK cells, primary NK cells, activated (aNK) cells), the cargo is DNA or RNA, and one or more of the electroporation parameters are as follows: (i) the field strength is applied at the voltage of about 20 V to about 50 V, or about 30 V to 50 V, about 40 V to about 50 V; (ii) the pulse width is about 100 µs to about 750 µs, about 200 µs to about 750 µs, or about 200 µs to about 600 µs; (iii) number of pulses is 2-6 or 2-3; and (iv) the cell density of the cells in the electroporation medium is about $10\times10^6$ cells/ml to about $300\times10^6$ cells/ml, about $10\times10^6$ cells/ml to about $250\times10^6$ cells/ml, or about $10\times10^6$ cells/ml to about $100\times10^6$ cells/ml. Additionally or alternatively, the electroporated NK cells (e.g., haNK cells, primary NK cells, activated (aNK) cells) with DNA or RNA cargo can have a viability of at least about 60%, at least about 70%, at least about 80%, or at least about 90% with a transfection efficiency of at least about 10%, at least about 50%, at least about 80%, at least about 90%, or at least about 95%.

In some embodiments, the cells are dendritic cells, the cargo is DNA or RNA, and one or more of the electroporation parameters are as follows: (i) the field strength is applied at the voltage of about 20 V to about 50 V, or about 30 V to 50 V, about 30 V to about 40 V; (ii) the pulse width is about 100 µs to about 750 µs, about 100 µs to about 500 µs, or about 200 µs to about 400 µs; (iii) number of pulses is 2-10 or 6-8; and (iv) the cell density of the cells in the electroporation medium is about $10\times10^6$ cells/ml to about $100\times10^6$ cells/ml, about $10\times10^6$ cells/ml to about $50\times10^6$ cells/ml, or about $10\times10^6$ cells/ml to about $25\times10^6$ cells/ml. Additionally or alternatively, the electroporated dendritic cells with DNA or RNA cargo can have a viability of at least about 70%, at least about 80%, or at least about 90% with a transfection efficiency of at least about 70%, at least about 80%, or at least about 90%.

In some embodiments, the cells are stem cells (e.g., AD-MSC cells), the cargo is DNA, and one or more of the electroporation parameters are as follows: (i) the field strength is applied at the voltage of about 20 V to about 50 V, or about 30 V to 50 V, about 30 V to about 40 V; (ii) the pulse width is about 50 µs to about 250 µs, about 50 µs to about 100 µs, or about 100 µs to about 200 µs; (iii) number of pulses is 2-10 or 6-8; and (iv) the cell density of the cells in the electroporation medium is about $10\times10^6$ cells/ml to about $100\times10^6$ cells/ml, about $10\times10^6$ cells/ml to about $50\times10^6$ cells/ml, or about $10\times10^6$ cells/ml to about $25\times10^6$ cells/ml. Additionally or alternatively, the electroporated stem cells (e.g., AD-MSC cells) with DNA cargo can have a viability of at least about 70%, at least about 80%, or at least about 90% with a transfection efficiency of at least about 70%, at least about 80%, or at least about 90%.

The methods described herein can apply to transient transfection or stable transfection. The term "transient transfection" refers to the introduction or transfection of nucleic acid that exists in the cell only for a limited period of time and is not integrated into the genome. The term "stable transfection" refers to transfection resulting in permanent expression of the gene of interest through the integration of the transfected nucleic acid into the nuclear genome, or the maintenance of a transfected plasmid as an extra chromosomal replicating episome within the cell.

In any embodiment, the methods described herein may further include a first cell sorting step and/or a second cell sorting step, for example, using the microfluidics devices as described herein. The first cell sorting step can sort the cells prior to introduction into the electroporation chamber by applying pressure to cause a first solution comprising the cells to flow through a microfluidics chamber as described herein comprising a plurality of rows of posts as described herein and deflecting the cells to a side of the chamber by the rows of posts to deplete cells from the solution exiting a first output mechanism as described herein and enrich cells in the solution exiting a second output mechanism as described herein. The cells exiting the second output mechanism can be introduced into the electroporation chamber with the cargo. The second cell sorting step can sort the electroporated cells after exiting the electroporation chamber by applying pressure to cause a fourth solution comprising the electroporated cells to flow through a microfluidics chamber as described herein comprising a plurality of rows of posts as described herein and deflecting the electroporated cells to a side of the chamber by the rows of posts to deplete electroporated cells from the solution exiting a third output mechanism as described herein and enrich electroporated cells in the solution exiting a fourth output mechanism as described herein.

The techniques and methods provided herein may be integrated into a variety of devices or platforms as part of a workflow. For example, an electroporation apparatus as described herein can be incorporated into an automated device, for example, in cartridge form, wherein electroporation can be performed along with one or more other automated processes on cells. For example, automated electroporation can be performed along with automated cell culturing and harvesting as described in U.S. Patent Publication No. 2017/0037357, which is incorporated by reference in its entirety.

In other aspects, a methods of in vivo transfection are provided wherein the methods described above are performed and the transfected cells, for example, mixed with an isotonic buffer, may be administered to a patient to treat a disease or disorder. Examples of diseases include, but are not limited to a mitochondrial disorder, cardiac dysfunction, heart failure, autism, diabetes mellitus, and deafness. It is also contemplated herein that the electroporation apparatuses described herein may be adapted for application to target tissue of a subject to aid in delivery of a drug or formulation, for example to aid in delivery of insulin or a drug for treatment of diabetes. For example, electrodes for electroporation may be applied onto the skin or a needle-like electrode pair may be subcutaneously administered. It is also contemplated herein that the electroporation apparatuses and methods may be used for adenovirus production, protein production, cellular immunotherapy, or regenerative medicine.

Kits are also provide herein. For example, the kits may include an electroporation apparatus as described herein, a first container for containing cells for transfection and cargo, a second container for containing electroporated cells, tubing for fluidly connecting the first container and the second container to the electroporation apparatus, and optionally, suitable reagents. In some embodiments, a kit may include a first package including a first module (e.g., first module 805), for example, containing the first container and a first portion of the tubing. The kit may further include a separate second package including a second module (e.g., second module 815), for example, containing the electroporation apparatus and a second portion of the tubing. The kit may also include a separate third package including a third module (e.g., third module 825), for example, containing the second container and a third portion of the tubing. Optionally, the reagents may be present in a separate fourth package. The first, second, third, and fourth packages may be sterile. Suitable reagents include, but are not limited to cells for transfection as described herein, an electroporation medium as described herein, and a combination thereof. Additionally or alternatively, a kit may further include electroporation chips, connection tubing, apparatus, tools for electroporation, electroporation buffers, supplements, reagents, and combinations thereof.

EXAMPLES

Example 1. Transfection of haNK Cells

In some aspects, conditions for the electroporation of haNK cells are shown in Table 2 below

TABLE 2

| \multicolumn{2}{c}{Conditions for Electroporation of haNK Cells} | |
|---|---|
| EP Parameter | Value |
| Cargo | Dextran 500 k (d × 500 k) at 50 ug/ml; GFP-mRNA (mRNA) at 50 ug/mL |
| Cell density | $5 \times 10^6 \sim 1 \times 10^7$/mL |
| Media | BTX: 8 mS/m, 0.27 osm/l; Cw100: 0.11 S/m, 0.12 osm/l; RPMI: 1.37 S/m, 0.28 osm/l |

TABLE 2-continued

| \multicolumn{2}{c}{Conditions for Electroporation of haNK Cells} | |
|---|---|
| EP Parameter | Value |
| Resistance (Rp) | 200Ω-inf |
| Electric Field | 1-3 kV/cm |
| Capacitance | 10 uF-150 uF |
| Device Parameters | ⌀5 mm, d = 420 um, Reg; ⌀5 mm, d = 560 um, Reg; ⌀10 mm, d = 284 um, offset |
| Flow Rate | 4-6.8 million cells/min |
| Total Sample | 16 million cells |
| Frequency | 2 Hz |
| No. of Pulses | 3-4 pulses (discharging or monophasic pulse train) |
| $Q_{avg}$ | 0.11-0.44 mL/min |
| Sample Size (cuvette) | 0.45 mL |
| Time constant | 10-30 ms |

Figure 7A:
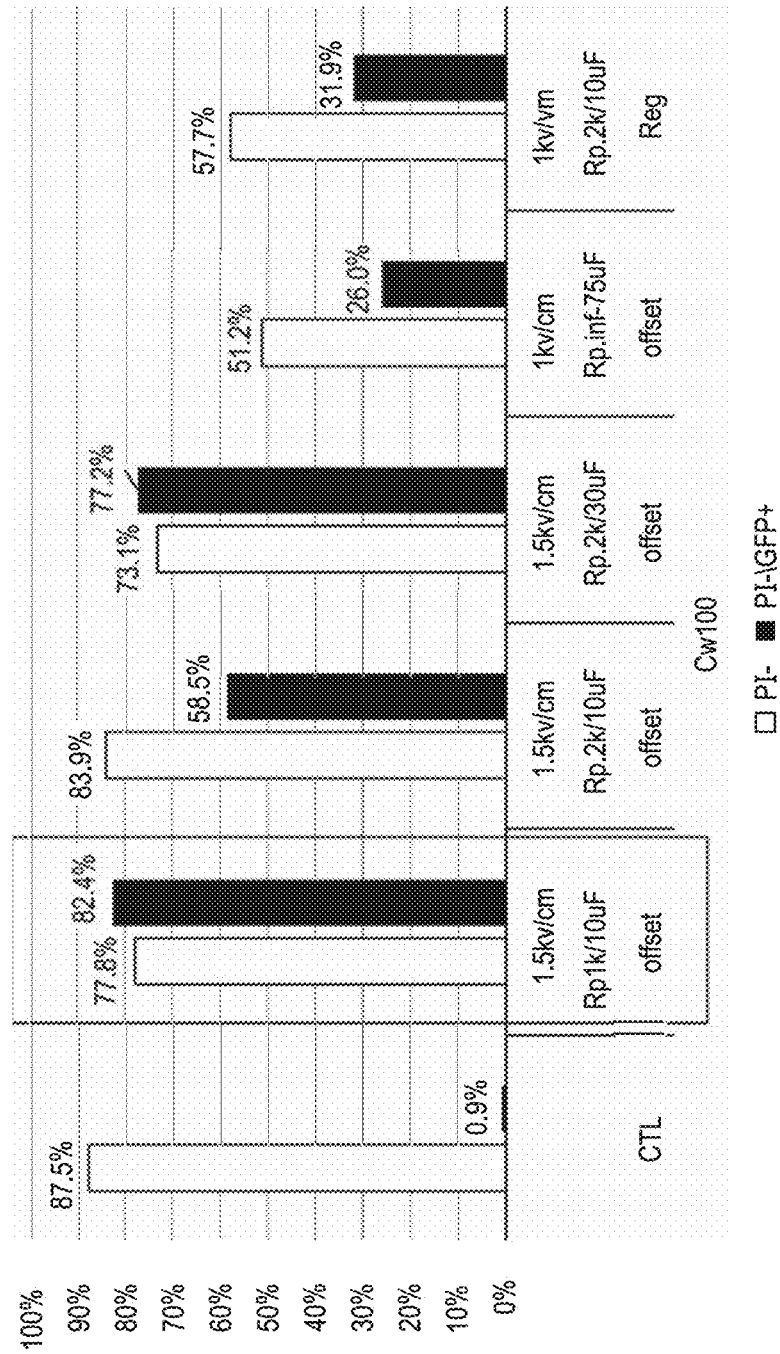
FIGS. 7A-7E show results of electroporation experiments for haNK cells and corresponding parameters, using the methods and devices described herein.
Figure 7B:
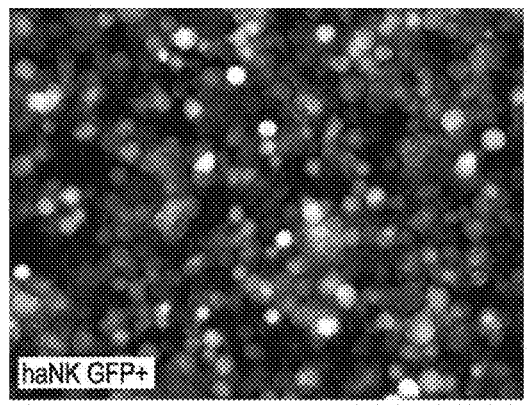
Figure 7C:
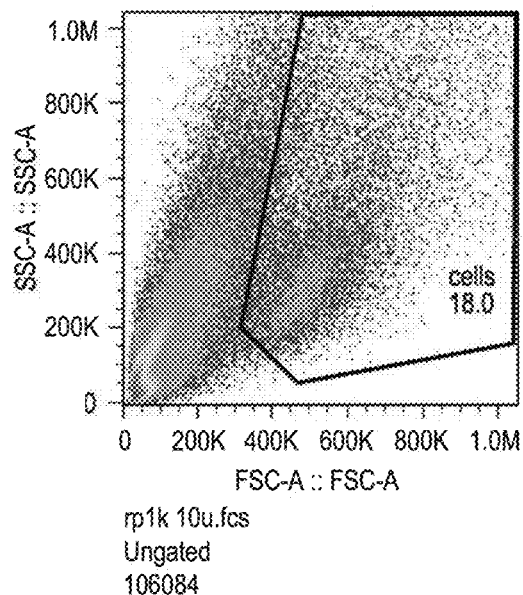
Figure 7D:
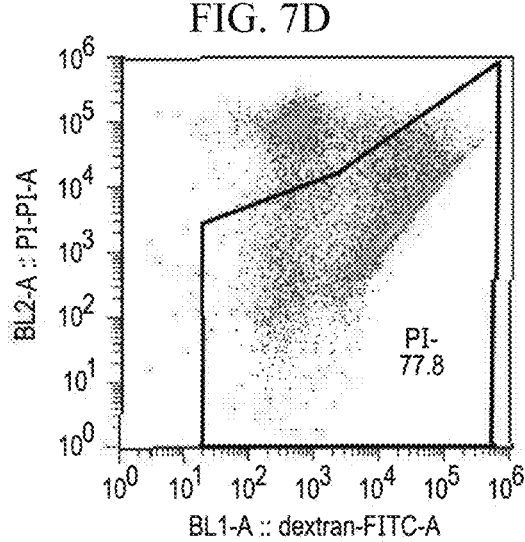
Figure 7E:
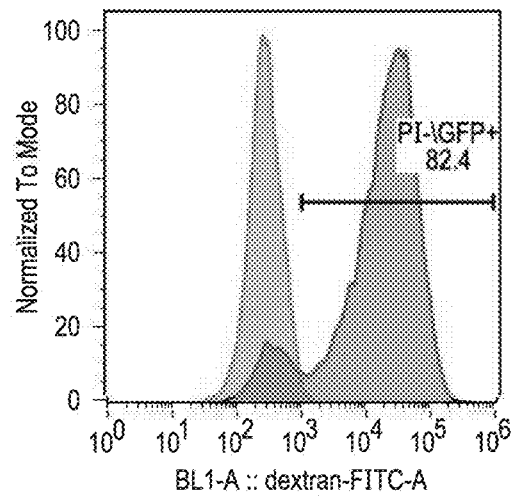

FIGS. 7A-E show experimental results of electroporation reactions. FIG. 7A shows a variety of experimental conditions with varying efficiencies and viabilities. Notably, the conditions of 1.5 kv/cm, Rp 1 k, 10 uF using the IOCO electroporation device resulted in greater than 80% efficiency with greater than 70% viability, with respect to GFP-mRNA electroporation into haNK cells. The designation "reg" refers to the original micromesh, while "offset" refers to the offset micromesh. FIG. 7B shows a microscopy image of GFP-mRNA that has been electroporated into hank cells. FIGS. 7C and 7D show results of cell sorting, with FIG. 7C showing live cells and FIG. 7D showing electroporated cells. FIG. 7E shows a histogram corresponding to the cell sorting results, showing control cells and cells electroporated with GFP.

Figure 8A:
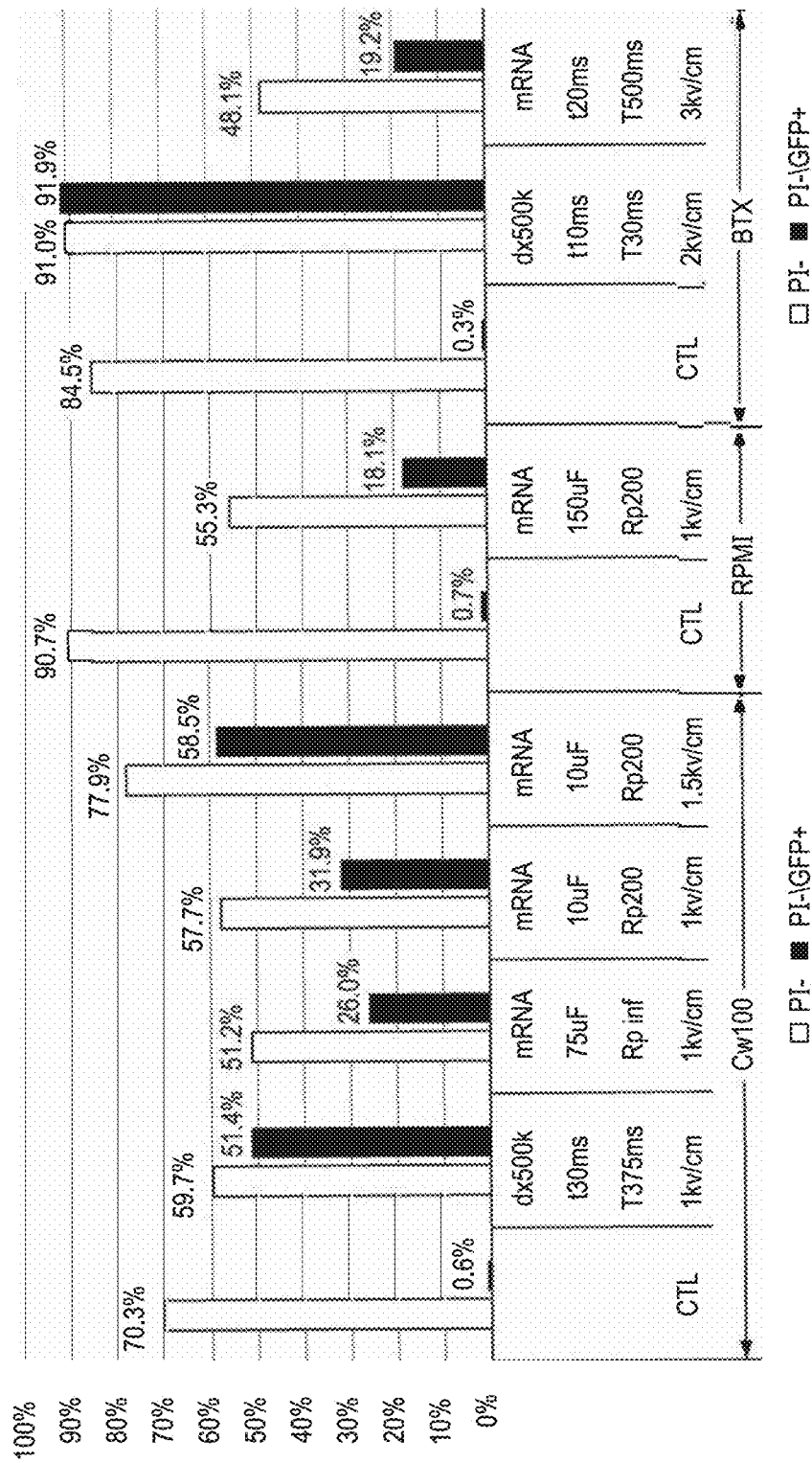
FIGS. 8A-8D show additional results of electroporation experiments for haNK cells and corresponding parameters, using the methods and devices described herein.
Figure 8B:
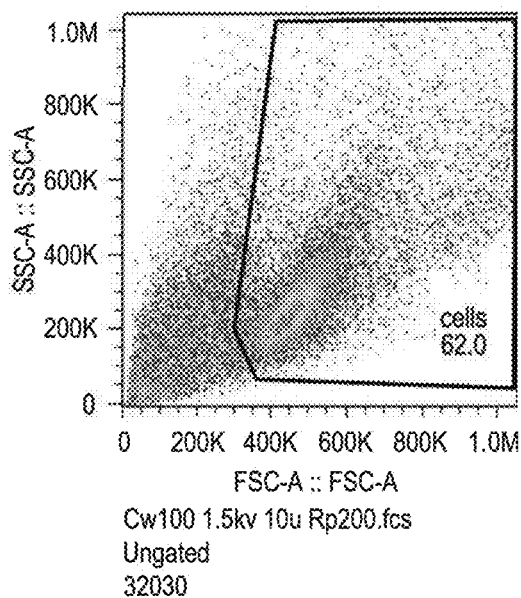
Figure 8C:
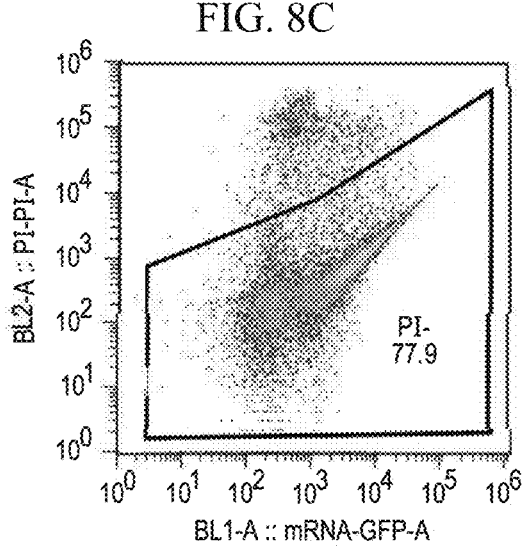
Figure 8D:
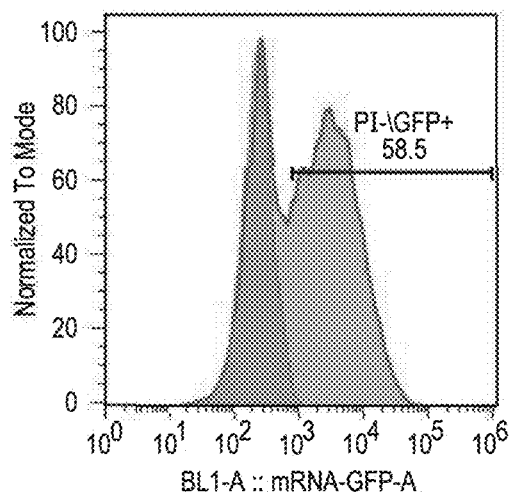

FIGS. 8A-8D shows another set of experimental results, under varying electroporation experimental conditions, with greater than 50% efficiency and greater than 70% viability of GFP-mRNA electroporation into haNKs. FIGS. 8B and 8C show results of cell sorting, with FIG. 8B showing live cells and FIG. 8C showing electroporated cells. FIG. 8D shows a histogram corresponding to the cell sorting results, showing control cells and cells electroporated with GFP. GFP expression was counted within the live cells (Propidium-Iodide negative, PI−). CTL represents control experiments.

Example 2. Transfection of EC7 Cells

Typical conditions for the electroporation of EC7 cells are shown in Table 3 below

TABLE 3

| \multicolumn{4}{c}{Conditions for Electroporation of EC7 Cells} | | | |
|---|---|---|---|
| EP Parameter | Value | EP Parameter | Value |
| Cargo | Dextran 500k (dx500k) at 50 ug/ml; GFP-mRNA (mRNA) at 50 ug/mL; GFP-DNA (DNA) at 50 ug/mL | Flow Rate | 4-17.6 million cells/min |
| Cell density | $5 \times 10^6 \sim 4 \times 10^7$/mL | Total Sample | 16 million cells |

TABLE 3-continued

Conditions for Electroporation of EC7 Cells

| EP Parameter | Value | EP Parameter | Value |
|---|---|---|---|
| Media | BTX: 8 mS/m, 0.27 osm/l; Cw100: 0.11 S/m, 0.12 osm/l; Cw240: 0.2 S/m, 0.24 osm/l; Eppendorf: 0.35 S/m, 0.09 osm/l; water | Frequency | 2 Hz |
| Resistance (Rp) | 200Ω to inf | No. of Pulses | 3-4 pulses (discharging or monophasic pulse train) |
| Electric Field | 0.3-3kV/cm | $Q_{avg}$ | 0.44 mL/min |
| Capacitance | 10-75 uF | Sample Size (cuvette) | 0.44-0.45 mL |
| Device Parameters | ⌀5mm, d = 420 um, Reg; ⌀5mm, d = 560 um, Reg; ⌀10mm, d = 284 um, offset | Time constant | 5-20 ms |

Figure 9A:
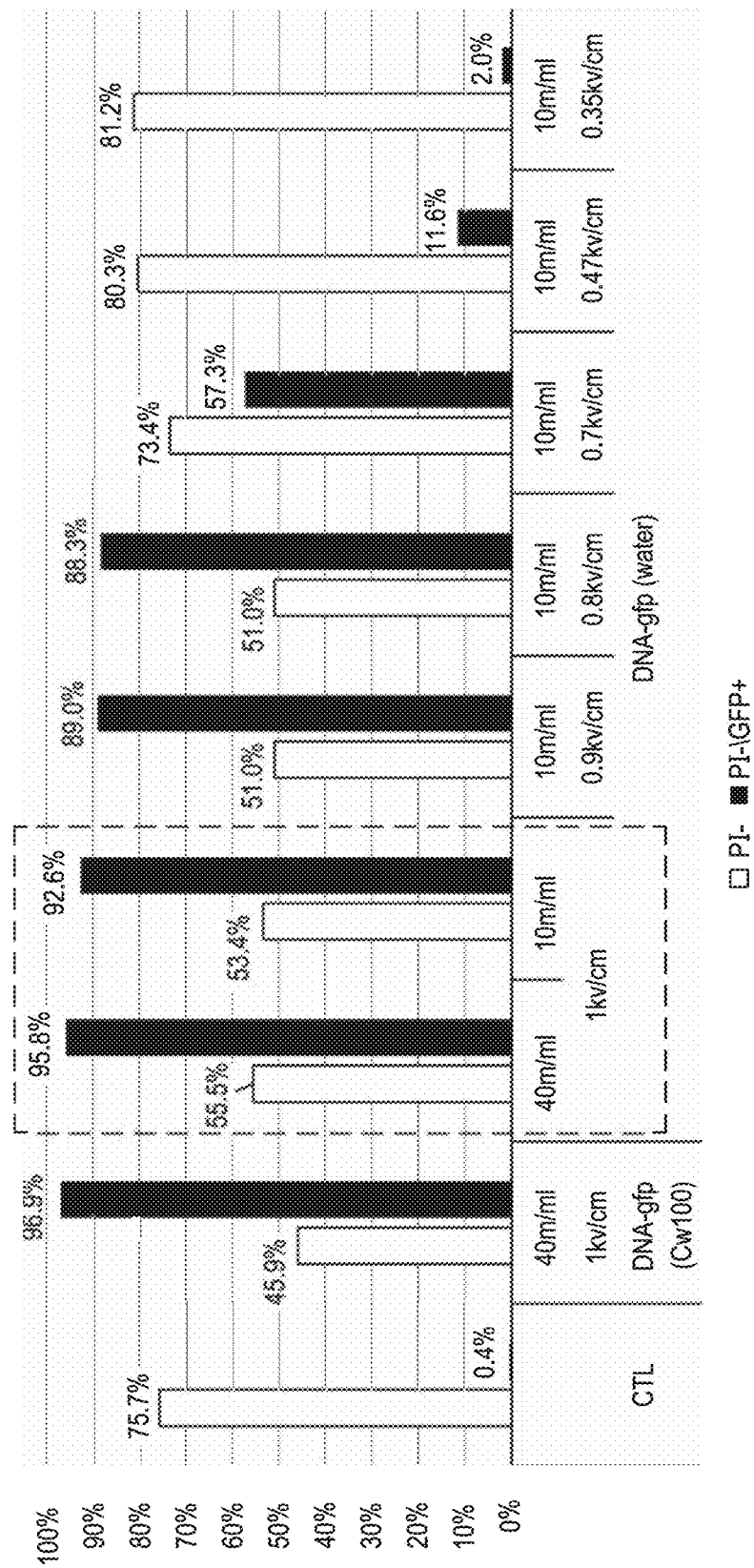
FIGS. 9A-9D show results of electroporation experiments for EC7 cells and corresponding parameters, using the methods and devices described herein.
Figure 9B:
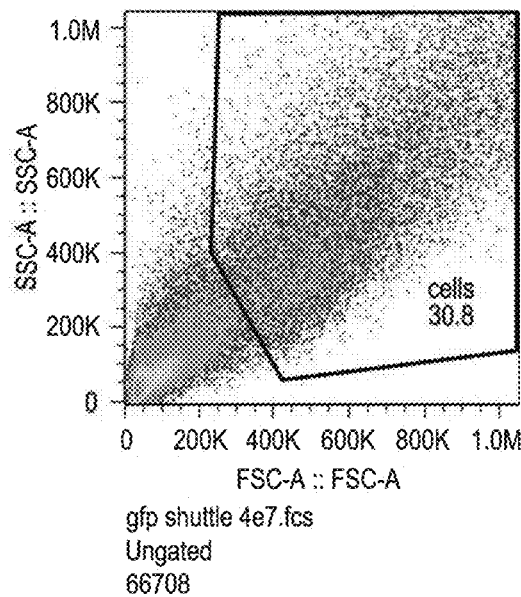
Figure 9C:
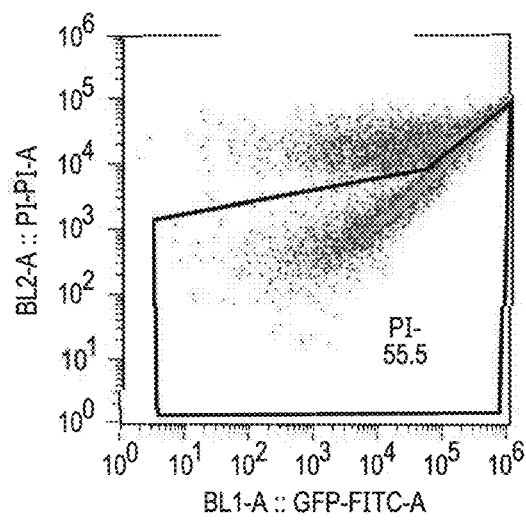
Figure 9D:
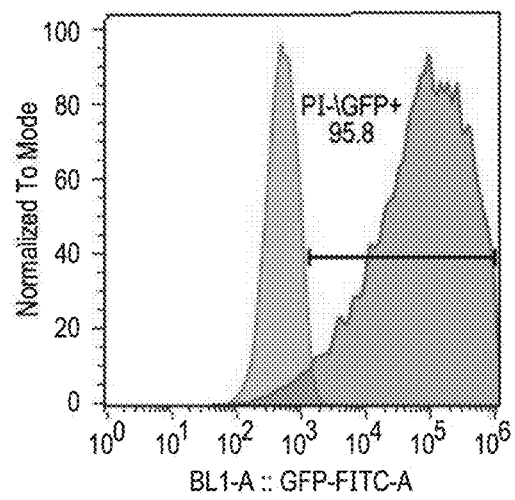

FIGS. 9A-9D show experimental results of electroporation reactions in EC-7 cells. FIG. 9A shows a variety of experimental conditions with varying efficiencies and viabilities. Notably, the conditions of 1 kv/cm, Rp 200, 10 uF using the IOCO electroporation device resulted in greater than about 90% efficiency and greater than about 50% viability of GFP-DNA electroporation into EC-7 cells. FIGS. 9B-9C show results of cell sorting, with FIG. 9B showing live cells, and FIG. 9C showing electroporated cells. FIG. 9D is a histogram corresponding to the cell sorting results, showing control cells and cells electroporated with GFP.

Figure 10A:
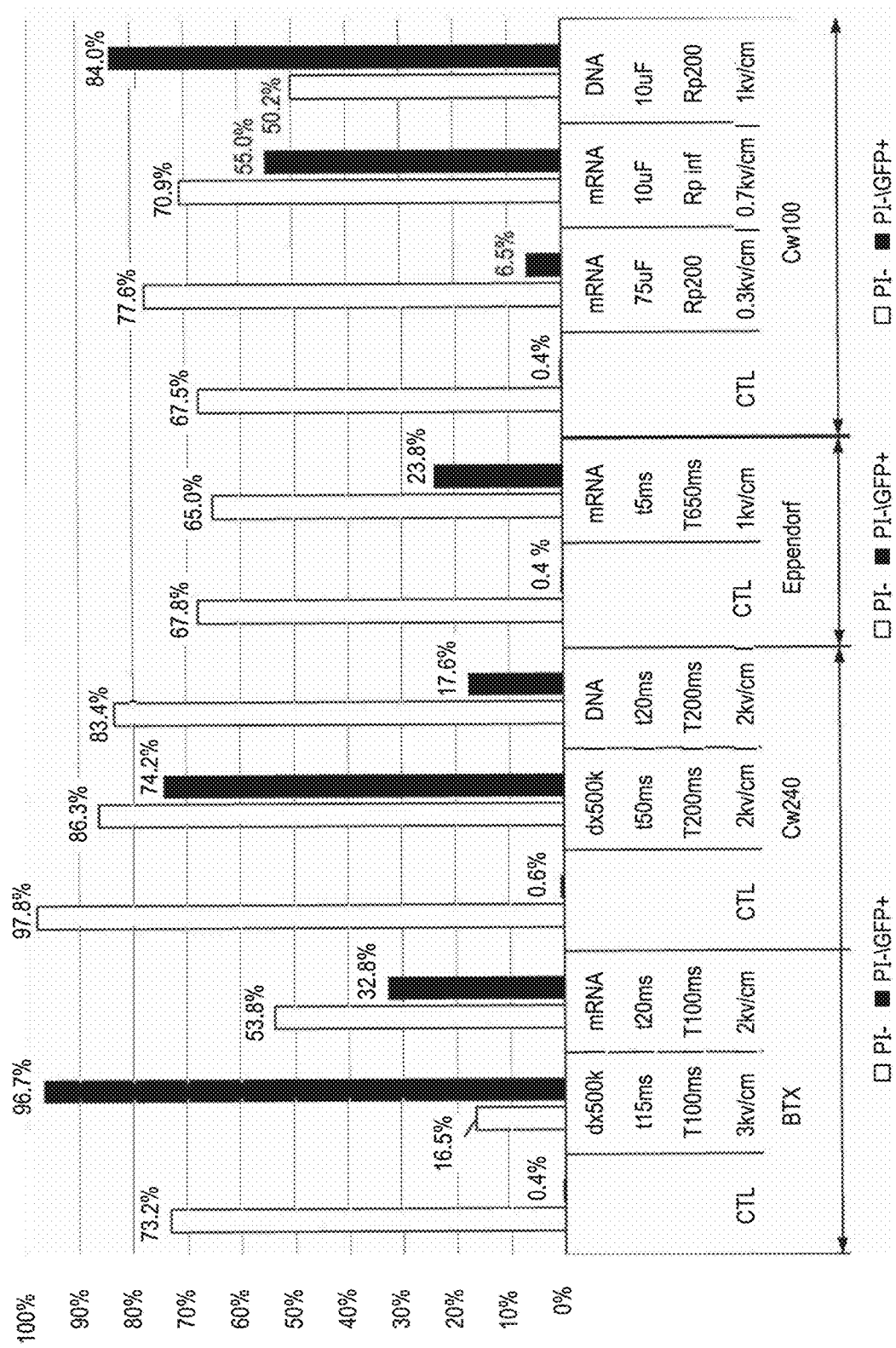
FIGS. 10A-10E show additional results of electroporation experiments for EC7 cells and corresponding parameters, using the methods and devices described herein.
Figure 10B:
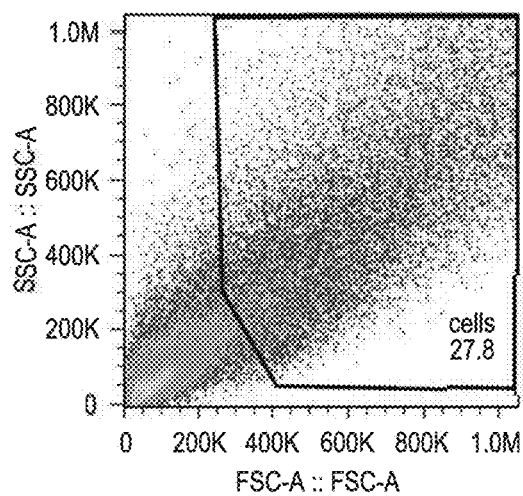
Figure 10C:
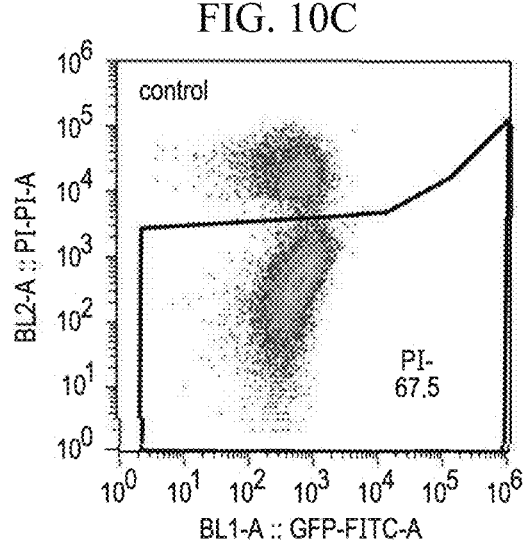
Figure 10D:
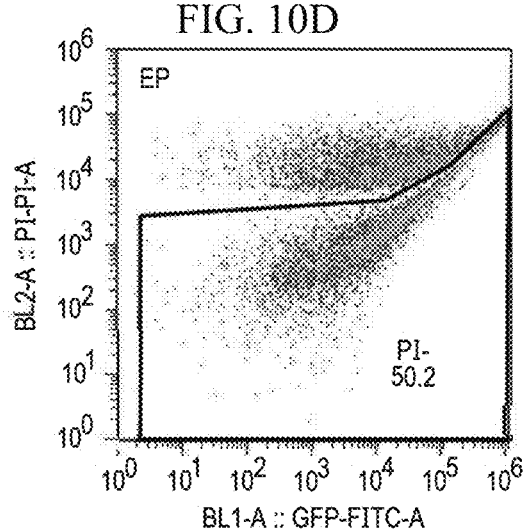
Figure 10E:
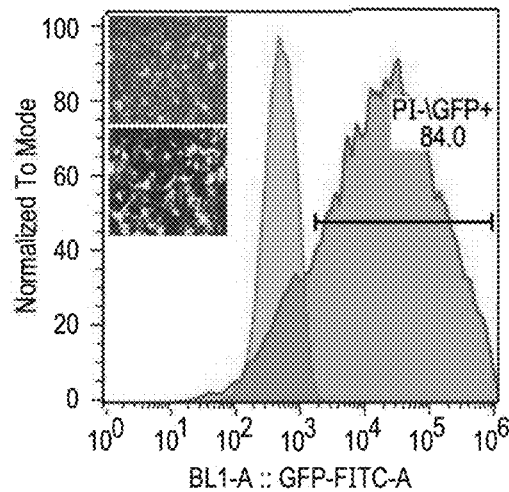

FIGS. 10A-10E show additional sets of experimental results in EC-7 cells, under varying electroporation experimental conditions. FIGS. 10B, 10C, and 10D show results of cell sorting, with FIG. 10B showing live cells and FIGS. 10C and 10D showing electroporated live cells. FIG. 10E shows a histogram corresponding to the cell sorting results, with control cells and cells electroporated with GFP. GFP expression was counted within the live cells (Propidium-Iodide negative, PI−). CTL represents control experiments.

Figure 11A:
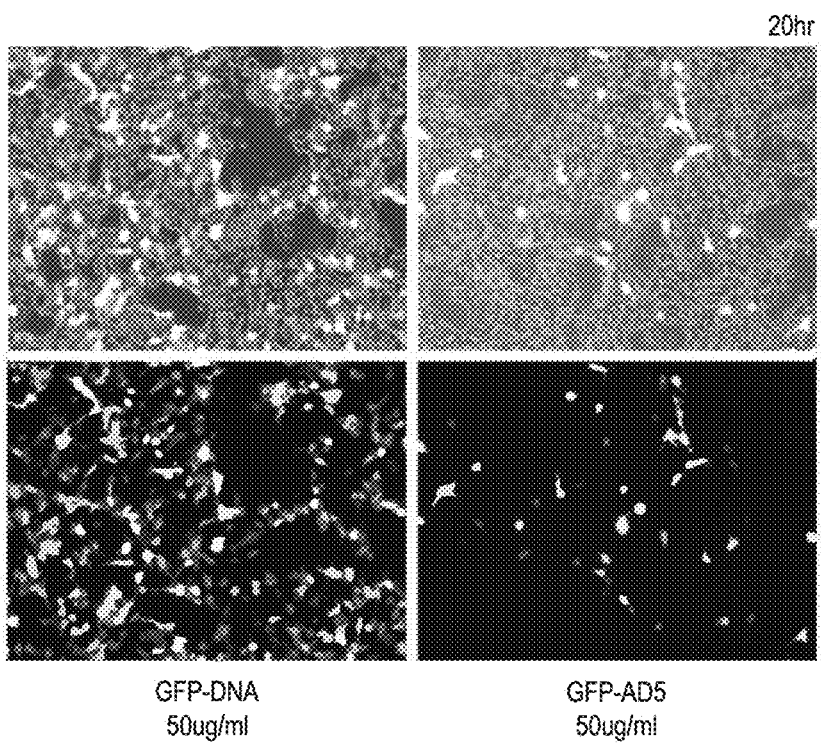
FIGS. 11A-11C show microscopic images of electroporated EC7 cells.
Figure 11B:
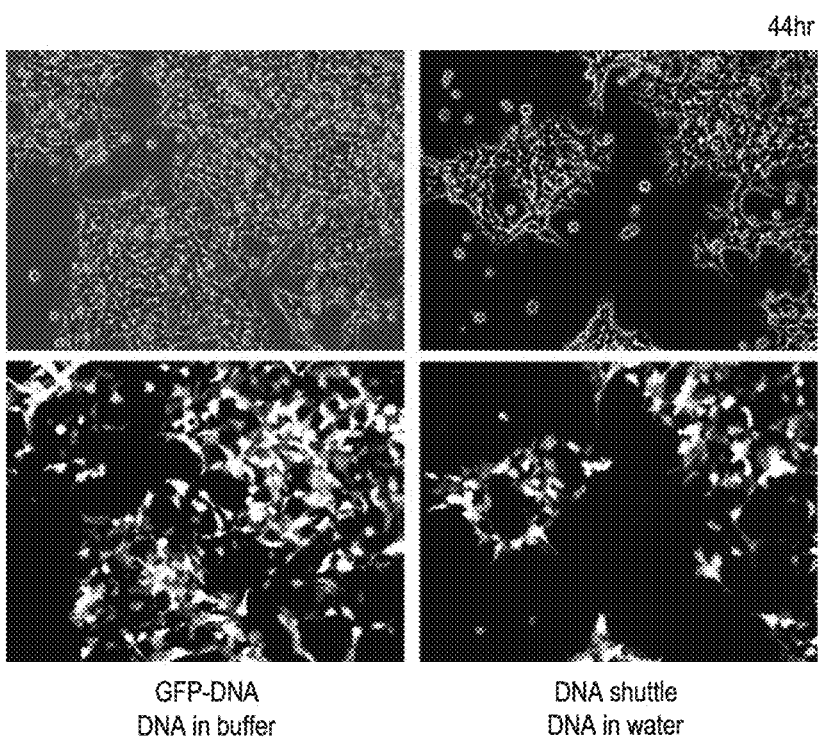
Figure 11C:
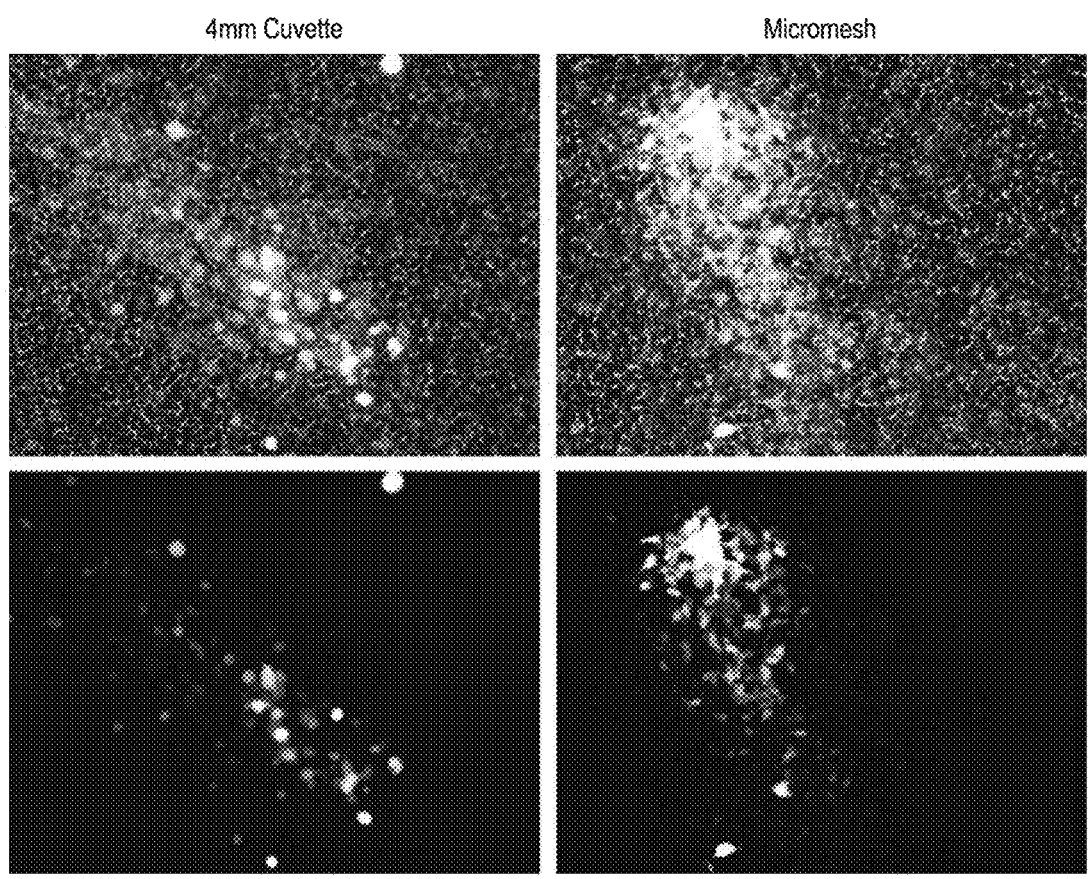

FIGS. 11A-11C show images of GFP-DNA that were successfully electroporated into EC-7 cells using the offset chamber electroporation device of FIG. 3A-C.

FIG. 11A was taken 20 hours after electroporation, and shows electroporation of GFP-DNA and GFP-AD5 (DNA encoding for AD5 virus production) into EC-7 cells. FIG. 11B was taken 44 hours after electroporation, and shows electroporation of GFP-DNA and a DNA shuttle vector into EC-7 cells. FIG. 11C was taken 6 days after electroporation and shows a comparison of electroporation results with a micromesh versus a cuvette.

FIG. 11C also shows comet formation during early stages of AD5 virus production in EC7 cells, according to the embodiments presented herein. In this series of images, cells form a cluster, or 'comet'-shaped plaque, with individual cells becoming more rounded in shape.

As shown by these series of images, the EC-7 cells were successfully electroporated with fluorescently tagged viral DNA (for AD5 virus production) and were able to initiate virus production, indicating that the techniques and systems provided herein are suitable for adenoviral production (e.g., for use in viral vaccines and the production of viral proteins).

Figures 12A, 12B:
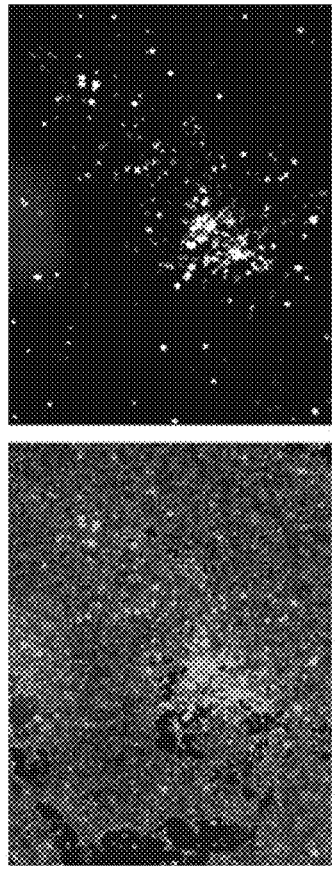
FIGS. 12A-12B show additional results of transfecting EC7 cells using the methods and devices described herein.

FIGS. 12A and 12B show additional results of transfecting EC7 cells using the methods and devices described herein. FIG. 12A shows a table of electroporation parameters, in which the amount of cargo was varied between electroporation runs. In FIG. 12B, images are shown six days after electroporation. By fourteen days post electroporation, about a 70-80% efficiency was observed. Multiple 'comet' shape clusters were observed post transfection. About 17-18 million cells/min may be transfected into EC7 cells at a cell concentration of about 40 m/ml in electroporation buffer cw100, which has a conductance of about 240 mS/m.

Example 3. Electroporation of Various Cell Types

In other aspects, the methods and systems provided herein may be used to transfect a variety of different cell types. For example, up to $10^8$ cells or more can be transfected by the methods and systems provided herein. The methods and systems provided herein may be used to transfect EC7 cells, haNK cells, CHO cells, and T cells. For example, the methods and techniques presented herein may be used to transfect EC7 cells using a flow rate of 0.6 ml/min with a cell concentration of $4\times10^7$ cells/ml. In another example, the methods and techniques presented herein may be used to transfect haNK cells using a flow rate of 0.36 ml/min with a cell concentration of $3\times10^7$ cells/ml. In yet another example, the methods and techniques provided herein may be used to transfect CHO cells using a flow rate of 0.45 ml/min with a cell concentration of $2.5\times10^7$ cells/ml. For T cells, the methods and techniques presented herein may be used to transfect T cells at a flow rate of 0.44 ml/min with a cell concentration of about $2\times10^7$ cells/ml. These conditions may be further varied in order to achieve optimal conditions.

Figure 13A:
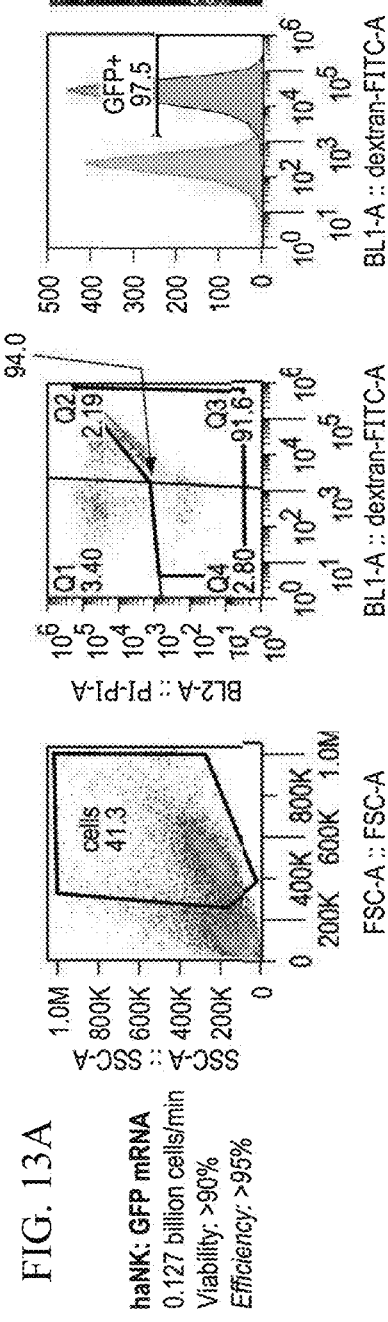
Figure 13B:
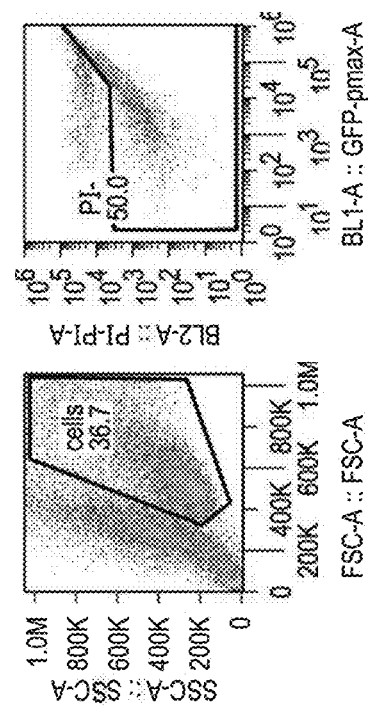

FIGS. 13A-13D show various transfection efficiencies for these different cell lines, using the methods and devices described herein. FIG. 13A shows a transfection efficiency of greater than 95% with a cell viability of greater than 90% for haNK cells (transfected with GFP mRNA). Up to 0.127 billion cells/min were transfected. FIG. 13B shows a transfection efficiency of greater than 90% with a cell viability of greater than 50% for CHO cells (transfected with GFP pmax DNA). Up to 15 million cells/min were transfected. FIG. 13C shows a transfection efficiency of greater than 95% with a cell viability of greater than 50% of EC7 cells (transfected with GFP adenovirus DNA). Up to 20 million cells/min or more were transfected. FIG. 13D shows a transfection efficiency of greater than 90% with a cell viability of greater than 80% of T cells (transfected with GFP mRNA). Up to 8.8 million cells/min were transfected.

Example 4. Transfection of Primary T Cells

In other aspects, the methods and systems presented herein have been used to electroporate primary T-cells with mRNA attached to poly(β-amino esters). Certain poly (β-amino ester) polymers have been shown to act as effective RNA transfection agents.

Nanoparticles comprising RNA and poly(β-amino ester) polymers have been used to deliver mRNA to T cells (see, e.g., Moffett, et al., Nature Communications (2017) 8:389). For example, in some embodiments, nanoparticles may be created with a polyglutamic acid (PGA)-based shell. A targeting molecule (e.g., a binding domain of an antibody) may be attached to the PGA molecule to target the nanoparticle to an appropriate target. For example, to target the nanoparticle to T cells, an anti-CD3/anti-CD28 binding domain may be attached to PGA molecules. PGA or any other suitable negatively charged molecule may be used for targeting. Uptake of the nanoparticle may occur by specific targeting or by cationic membrane association.

The interior of the nanoparticle may comprise mRNA and a carrier molecule such as poly(β-amino esters). Once the nanoparticle is taken up into the cell, the mRNA is released into the cell by degradation of the nanoparticle, by osmotic swelling, or some other suitable process and the mRNA is transcribed into its respective protein. In some cases, synthetic mRNA may be used to reduce mRNA degradation.

Figure 14D:
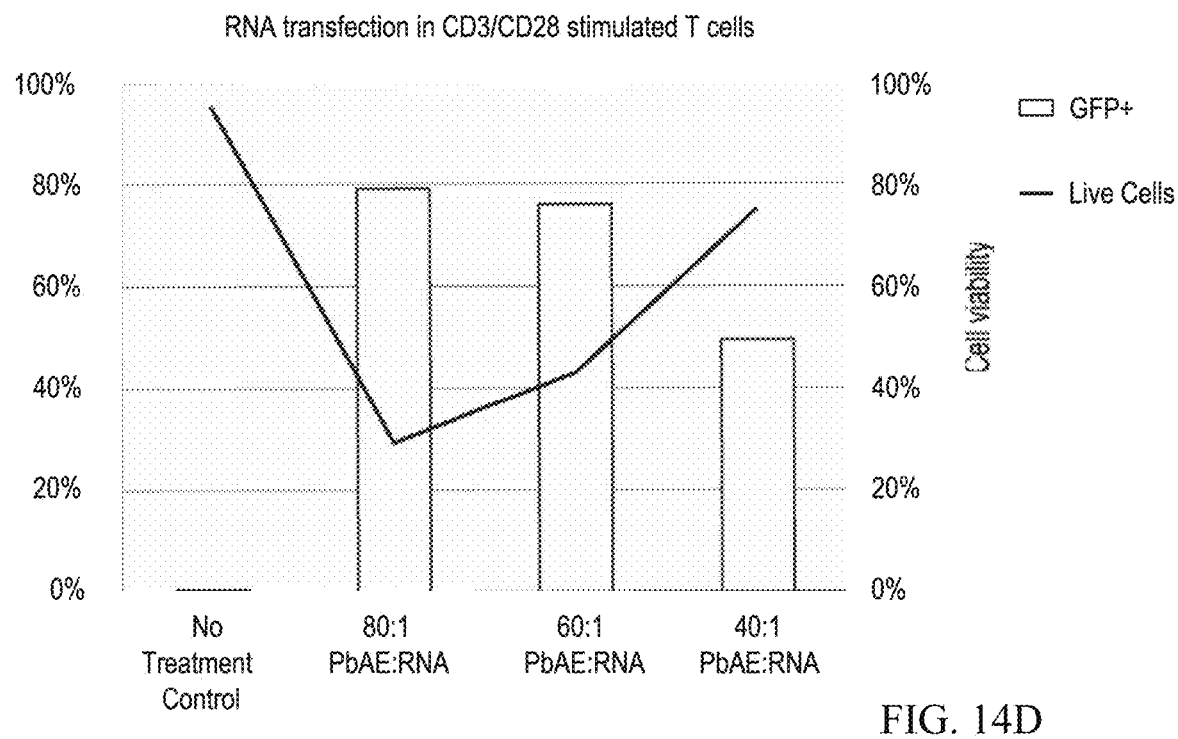
Figure 14E:
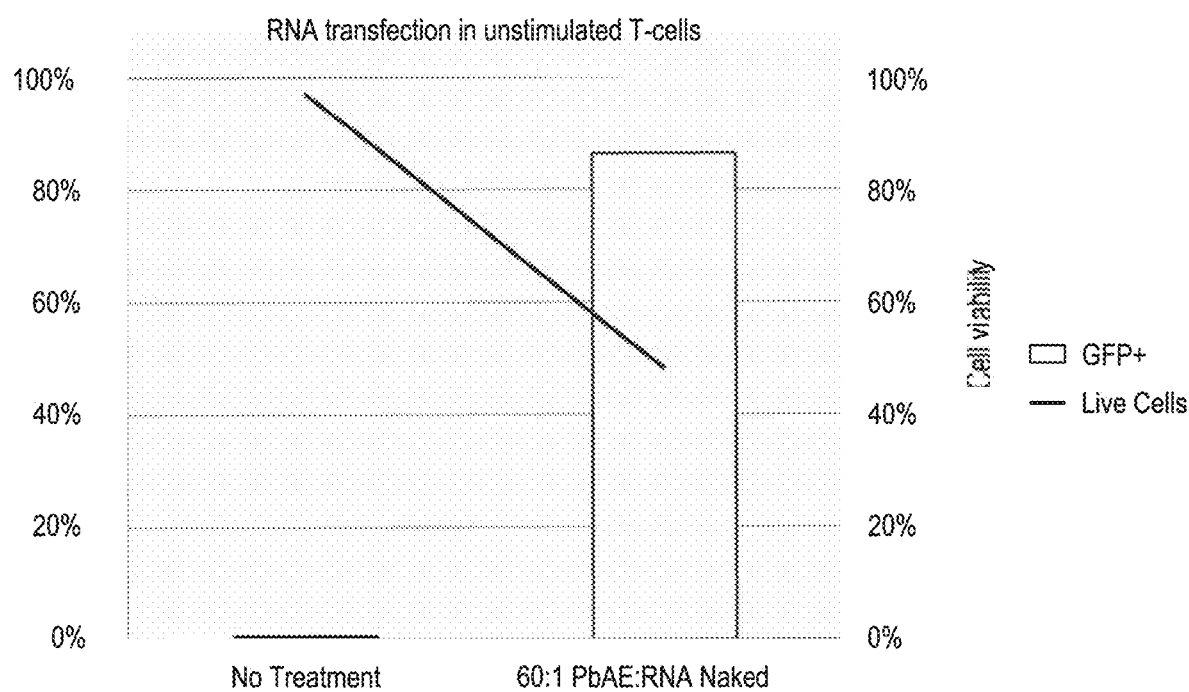

The methods provided herein may be used to transfect mRNA into cells, e.g., by using mRNA and a poly(β-amino ester) (PbAE) carrier or using a nanoparticle encapsulating mRNA and a poly(β-amino ester) carrier. FIGS. 14A-14E show T cell transfections with PbAE complexed with mRNA (not free mRNA, and without electroporation). FIG. 13A shows a structure of a poly(β-amino ester) suitable for use with the techniques provided herein. FIG. 14B shows cell sorting results using flow cytometry of T cells transfected with mRNA using PbAE. FIG. 14C is a graph showing normalized results for live cells based on varying ratios of mRNA to carrier molecule. FIGS. 14D and 14E show cell viability results under various conditions for GFP-mRNA transfection in stimulated T cells (FIG. 14D) and unstimulated T cells (FIG. 14E). In these experiments, a ratio of 60:1 PbAE:RNA led to a high level of viable cells while providing a high GFP delivery rate.

Figure 15A:
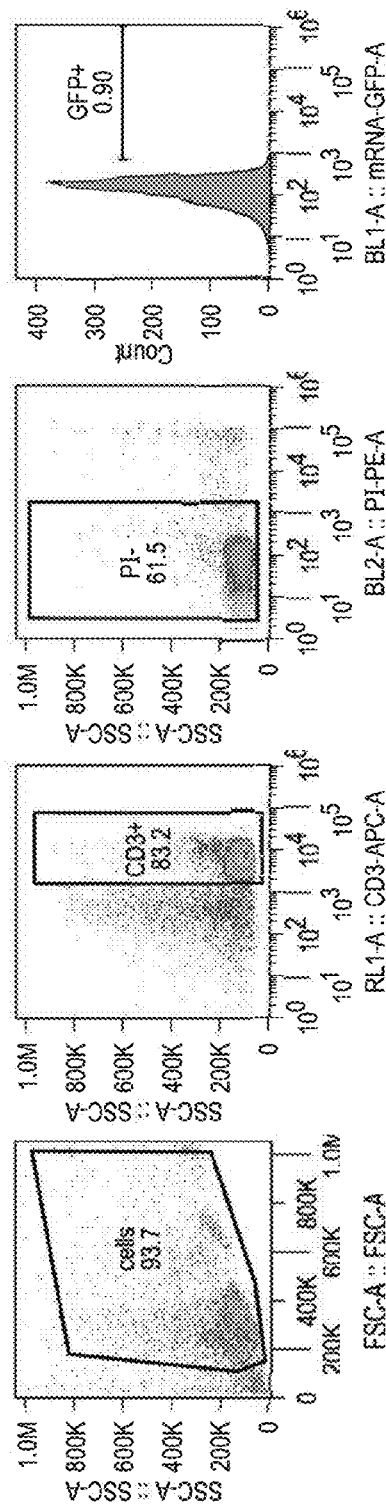
FIGS. 15A and 15B show results of transfection experiments for introducing mRNA into T-cells with and without electroporation, as described herein.
Figure 15B:
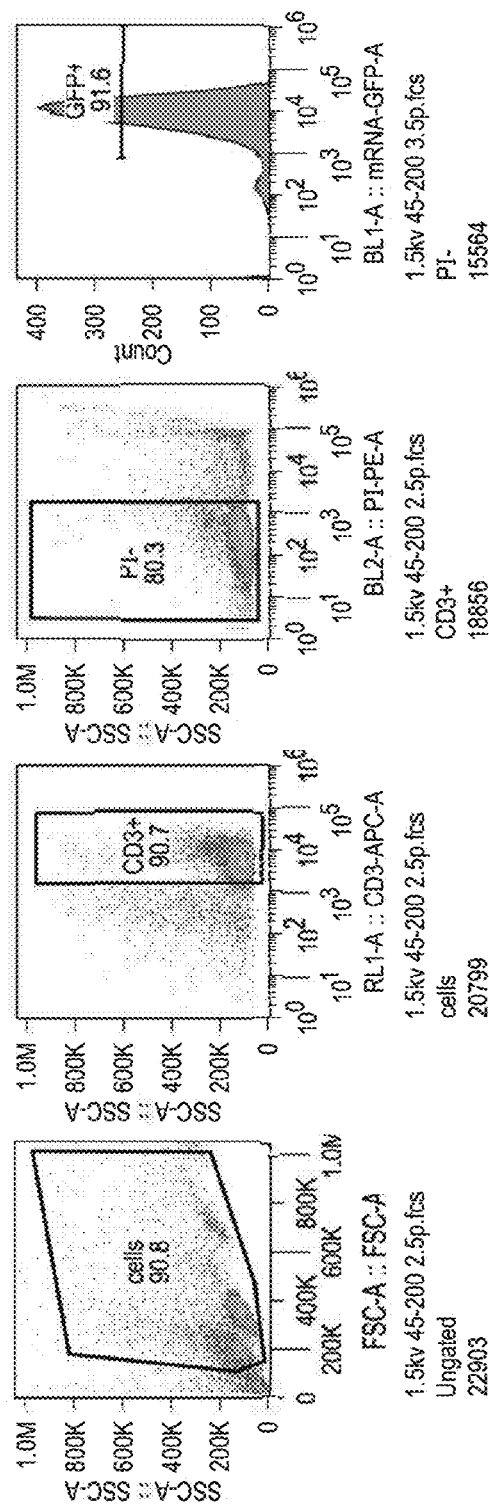

FIGS. 15A and 15B show T cell GFP mRNA transfection using control cells (no electroporation) and electroporated cells. In particular, FIG. 15A shows control cells (no electroporation), wherein background fluorescence is primarily observed. FIG. 15B shows electroporated cells, in which GFP-mRNA is detected in the majority of cells, as shown by the histogram.

Example 5. Transfection of Adipose-Derived Mesenchymal Stem Cells (AD-MSC)

Adipose-derived mesenchymal stem cells (AD-MSC) detached and harvested at density about $1\times10^5$ million per milliliter. Cells were washed with PBS and electroporation buffer, and suspend in electroporation buffer with density of 3.3 million cells per milliliter. Each condition were electroporated with 0.1 milliliter of final cell density with 30 μg of DNA. The electroporation conditions are: pulse width=100 us, pulse period=340 ms, electric field strength varies from 0.9 to 1.6 kV/cm as shown in Table 4 below

TABLE 4

| Electroporation Field Strength Conditions | |
|---|---|
| # | kv/cm |
| 1 | 1.6 |
| 2 | 1.5 |
| 3 | 1.4 |
| 4 | 1.3 |
| 5 | 1.2 |
| 6 | 1.1 |
| 7 | 1.0 |
| 8 | 0.9 |

Figures 16A, 16B:
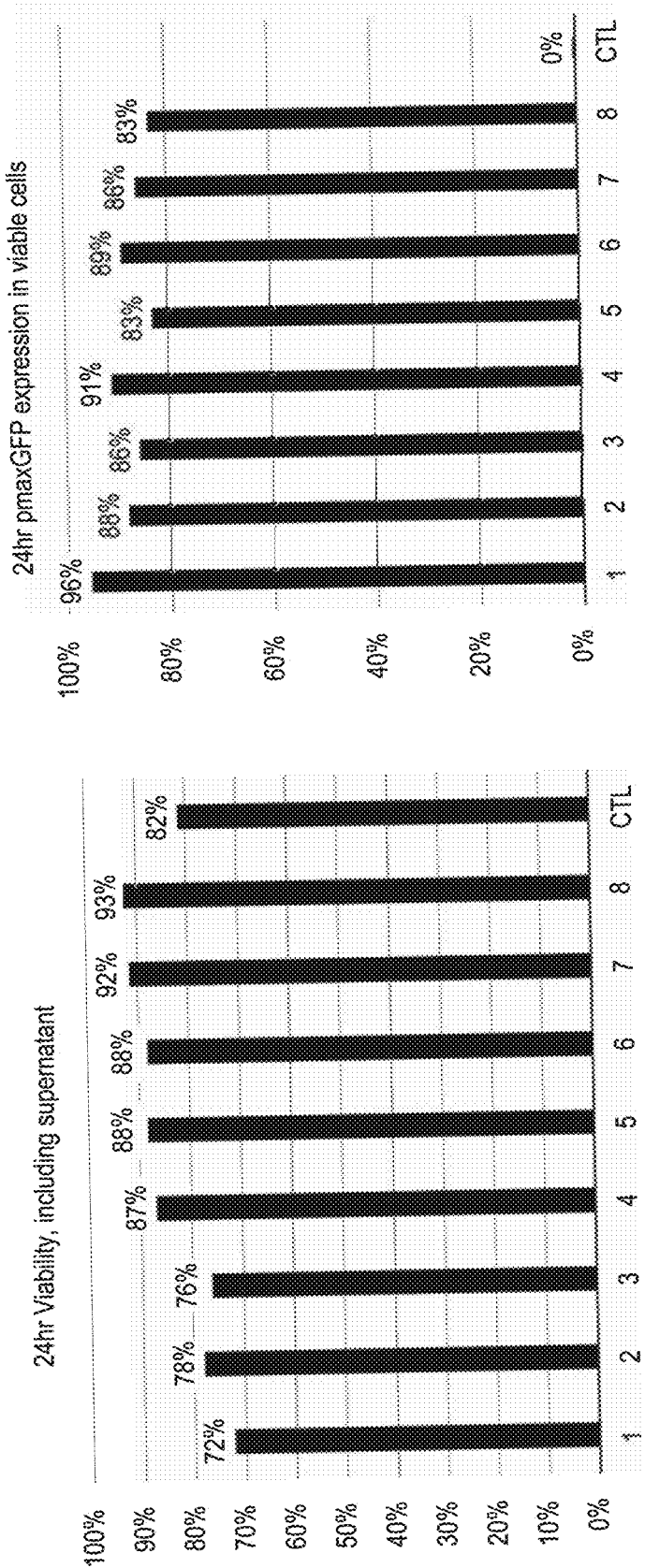
FIGS. 16A-16D show results of transfection experiments for Adipose-derived mesenchymal stem cells (AD-MSC) and corresponding parameters, using the methods and devices described herein.
Figure 16C:
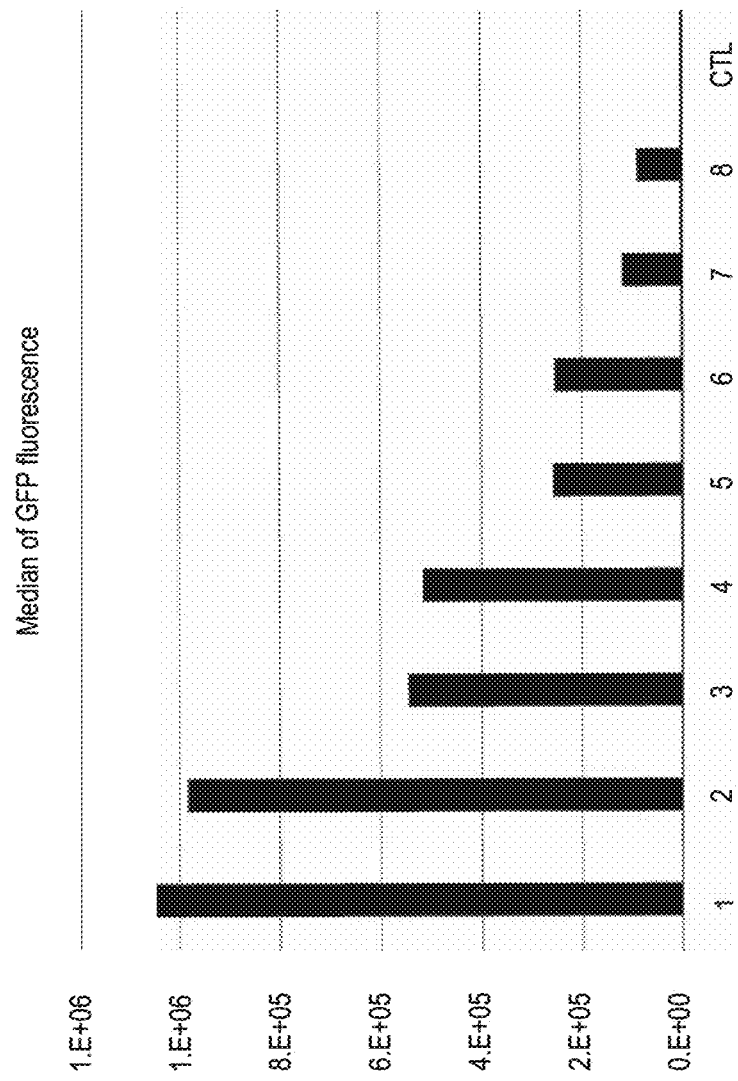
Figure 16D:
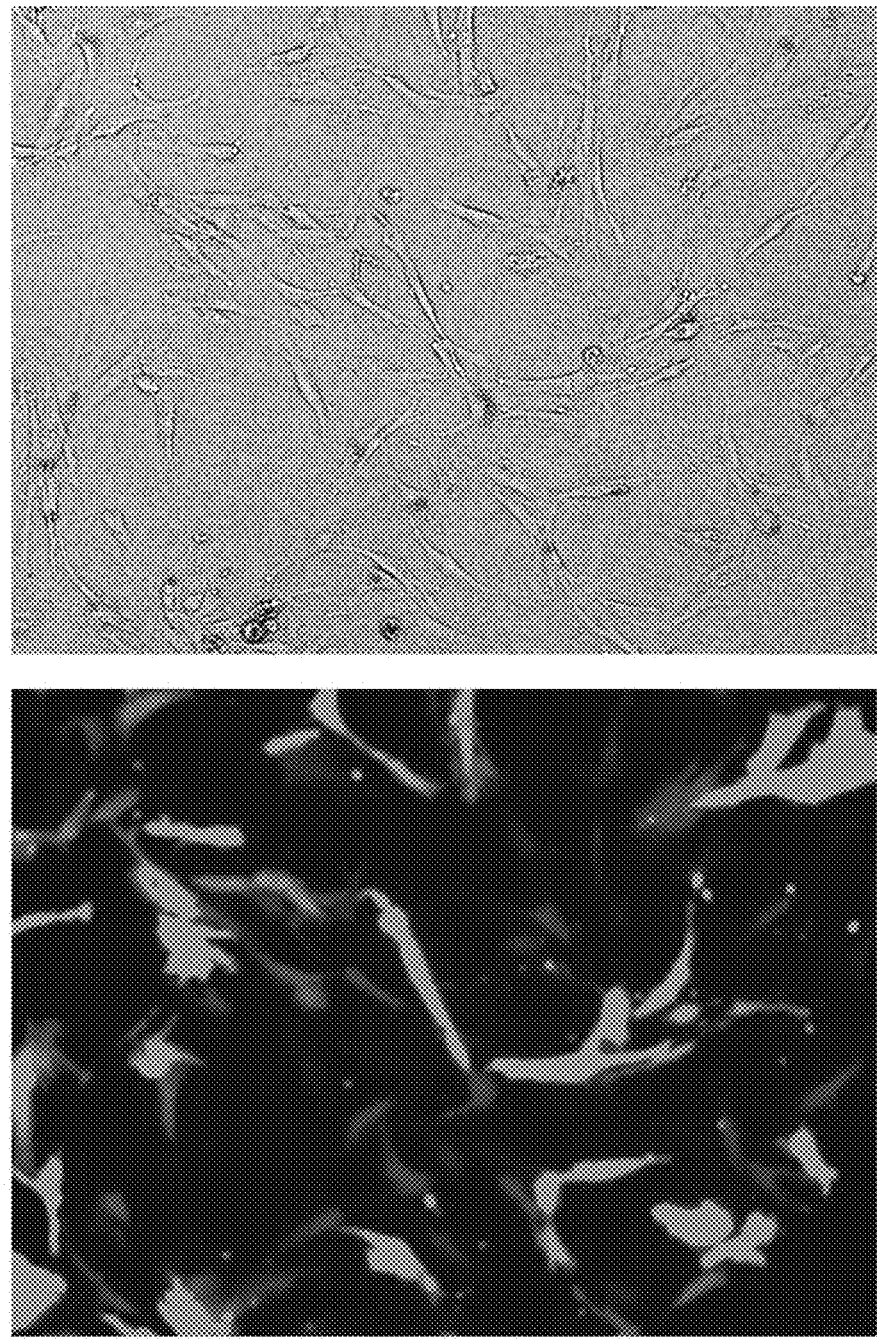

After electroporation, cells were seeded at density of $30\times10^3$ cells per centimeter square. GFP expression efficiency were verified with flow cytometry 24 hours post electroporation. The results are shown in FIGS. 16A-16D. The x-axis values of 1-8 in each of FIGS. 16A-15C correspond to the field strengths as shown in Table 4 and "CTL" corresponds to the control, without electroporation. FIG. 16A shows cell viability, 24 hr after electroporation. The lower electric field strength, the more viable cells are. FIG. 16B shows GFP (green fluorescent protein) expression read by flow cytometry for cell transfection efficiency measurement, 24 hours after electroporation. The stronger electric field, the higher percent of live cells expressed GFP. FIG. 16C shows median of the GFP fluorescence, which denotes how bright the GFP was in the flow cytometry measurement. The stronger electric field, the brighter GFP was measured. Results suggested that the electric field strength between 1.1 to 1.3 kv/cm may give the best performance among viability and efficiency. Note that the viability here includes both attached cells and supernatant to reflect the true overall viability. FIG. 16D is a photograph of the MSC transfection result. The left hand photograph shows the morphology of the MSCs and the right hand image is a fluorescent image for the same optical field showing that most of the cells express green fluorescent protein (green).

Example 6. Transfection of EC-7 Cells, CHO-S Cells, Primary CD4/CD8 T Cells, haNK Cells, Primary NK Cells, Activated NK Cells, Dendritic Cells, AD-MSC Cells EC-7 cells, CHO-S cells, primary CD4/CD8 T cells, haNK cells, primary NK cells, activated NK cells, dendritic cells, AD-MSC cells were electroporated in an apparatus similar to the apparatus depicted in FIG. 2A with the electroporation parameters shown below in Table 5.

TABLE 5

Electroporation Parameters

| Cell line | Target | Size (kbp) | Transfect Style | Electro Medium | Cell density (10^6/ml) | Voltage (V) | Pulse Width (μs) | No. of Pulses | Flow rate (mL/min) |
|---|---|---|---|---|---|---|---|---|---|
| EC.7 | linearized adenovirus DNA | 35 k-40 k | Transient | 2 | 40-100 | 31 | 30 | 2-3 | 1-1.5 |
| CHO-S | pMAX-GFP DNA | 3.5 k | Transient | 1 | 100 | 45 | 600 | 2 | 1-10 |
| CHO-S | Fusion protein DNA | <10 k | Transient | 1 | 100 | 45 | 600 | 2 | 1-2 |
| Primary CD4/CD8 T cell | mRNA | <1 k | Transient | 2 | 10-200 | 46 | 200 | 6 | 1-2 |
| Primary CD4/CD8 T cell | pMAX-GFP DNA | 3.5 k | Stable | 2 | 10-200 | 46 | 400 | 6 | 1-2 |
| haNK | mRNA | <1 k | Transient | 2 | 10-200 | 45 | 200 | 2-6 | 1-10 |
| Primary NK | mRNA | <1 k | Transient | 2 | 10-200 | 45 | 250 | 6 | 1-2 |
| Activated NK (aNK) | DNA | <10 k | | 2 | 60 | 45 | 600 | 2 | 1-2 |
| Dendritic Cell | mRNA | <1 k | Transient | 2 | 10-20 | 31 | 200 | 6-8 | 1-2 |
| Dendritic Cell | pMAX-GFP | 3.5 k | Stable | 2 | 10-20 | 31 | 400 | 6-8 | 1-2 |
| AD-MSCs | DNA | <10 k | Stable | 2 | 10 | 36 | 100 | 6 | 1-2 |

The compositions of Electroporation Medium ("Electro Medium") 1 and 2 used in Table 5 are shown below in Tables 6 and 7.

TABLE 6

Electroporation Medium 1 Composition

| Solute | brand/Cat# | MW | Molar concentration (mol/L) |
|---|---|---|---|
| KCl Potassium chloride | Fluka, 60129 | 74.55 | 0.1 |
| Na$_2$HPO$_4$ Sodium phosphate dibasic | Sigma, S3397 | 141.96 | 0.008 |
| MgCl$_2$ Magnesium chloride | Sigma, M8266 | 95.211 | 0.001 |
| D-(+)-Glucose glucose | Sigma, G7021 | 180.156 | 0.04 |
| HEPES | Fisher BP310 | 238.3 | 0.025 |
| Conductivity | 12 mS/cm | | |
| Osmolarity | ~278 mOsm/L | | |

TABLE 7

Electroporation Medium 1 Composition

| Solute | brand/Cat# | MW | Mole in 1L (M) |
|---|---|---|---|
| KCl Potassium chloride | Fluka, 60129 | 74.55 | 0.02 |
| Na$_2$HPO$_4$ Sodium phosphate dibasic | Sigma, S3397 | 141.96 | 0.008 |
| MgCl$_2$ Magnesium chloride | Sigma, M8266 | 95.211 | 0.001 |
| D-(+)-Glucose glucose | Sigma, G7021 | 180.156 | 0.18 |
| HEPES | Fisher BP310 | 238.3 | 0.025 |
| Conductivity | 4 mS/cm | | |
| Osmolarity | ~275 mOsm/L | | |

The results of electroporating the cells in Table 5 according to the given parameters is provided below in Table 8.

TABLE 8

Electroporation Results

| Cell line | Target | Parameters and Current Performance | | | |
|---|---|---|---|---|---|
| EC.7 | Linearized | Cell Density | 40-100 × 10$^6$ cells/ml | Flow rate | 100 × 10$^6$ cells/minutes |
| | | DNA conc. | 100-300 μg/ml | # of cell processed | 100 × 10$^6$ cells |
| | | Viability | >80% | Efficiency | ~10$^8$-10$^9$ IFU/ml at V1 |

TABLE 8-continued

Electroporation Results

| Cell line | Target | Parameters and Current Performance | | | |
|---|---|---|---|---|---|
| CHO-S | pMAX-GFP/ PD-L1 protein | Cell density | 100-200 × $10^6$ cells/ml | Flow rate | 150 × $10^6$ cells/minutes |
| | | DNA conc. | 200-300 µg/ml | # of cell processed | 40-1000 × $10^6$ cells |
| | | Viability | >90% (48 hr) >70% (14 days) | Efficiency | RSBC6 IgG titer > 0.5 mg/ml N-844-2 titer > 0.35 mg/ml |
| Primary CD4/CD8 T cell | mRNA/ pMAX-GFP/ CAR CD-19 | Cell Density | 10-100 × $10^6$ cells/ml | Flow rate | 100 × $10^6$ cells/minutes |
| | | DNA conc. | 50-100 µg/ml | # of cell processed | 10 × $10^6$ cells |
| | | Viability | >90% | Efficiency | >99% (Trilink mRNA-GFP 24 hr) >25% (DNA Stable Transfection) |
| haNK | mRNA | Cell Density | 30 × $10^6$ cells/ml | Flow rate | 127 × $10^6$ cells/minutes |
| | | DNA conc. | 60 µg/ml | # of cell processed | 300 × $10^6$ cells |
| | | Viability | >90% | Efficiency | >95% (Trilink 24 hr) |
| Primary NK | mRNA GFP/CAR | Cell Density | 100 × $10^6$ cells/ml | Flow rate | 100 × $10^6$ cells/minutes |
| | | DNA conc. | 100 µg/ml | # of cell processed | 10 × $10^6$ cells |
| | | Viability | <5% drop compared to control | Efficiency | >90% (Trilink GFP 24 hr) |
| Activated NK (aNK) | DNA | Cell Density | 50 × $10^6$ cells/ml | Flow rate | 50 × $10^6$ cells/minutes |
| | | DNA conc. | 200 µg/ml | # of cell processed | 30 × $10^6$ cells |
| | | Viability | <50% drop compared to control | Efficiency | >10% (Stable Transfection) |
| Dendritic Cell | mRNA/ pMAX-GFP | Cell Density | 10 × $10^6$ cells/ml | Flow rate | 1000 × $10^6$ cells/minutes |
| | | DNA conc. | 100 µg/ml | # of cell processed | 2 × $10^6$ cells |
| | | Viability | <90% | Efficiency | >90% (Trilink mRNA-GFP 24 hr) |
| AD-MSCs | pMAX-GFP | Cell Density | 3 × $10^6$ cells/ml | Flow rate | 0.8 mL/min |
| | | DNA conc. | 100-300 µg/ml | # of cell processed | 3 × $10^6$ cells |
| | | Viability | <5% drop compared to control | Efficiency | >90% 24 hr |

In some embodiments, the numbers expressing quantities of ingredients, properties such as concentration, reaction conditions, and so forth, used to describe and claim certain embodiments are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments are approximations, the numerical values set forth in the specific examples are reported as precisely as practicable. The numerical values presented in some embodiments may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It should also be apparent to those skilled in the art that many more modifications besides those already described herein are possible without departing from the inventive concepts herein. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of loading cells with a cargo, comprising:
flowing the cells and the cargo into an electroporation chamber, wherein the electroporation chamber comprises:
  a first electrode;
  a second electrode;
  a first input allowing the flowing of the cells and the cargo into the electroporation chamber;
  a first output allowing passage of electroporated cells from the electroporation chamber; and
  a fluid channel region having a path defined therein between the first electrode and the second electrode for the cells and the cargo to flow;
  wherein the cells are suspended in an electroporation medium with a cell density of about $1\times10^6$ cells/ml to about $500\times10^6$ cells/ml; and
applying multiple electrical pulses to the cells and the cargo within the electroporation chamber,
wherein:
  (i) each electrical pulse has a form of an exponentially discharging waveform or a square waveform,
  (ii) the multiple electrical pulses are applied at a field strength of about 0.3 kV/cm to about 3 kV/cm;
  (iii) the field strength is applied at a voltage of about 15 V to about 100 V;
  (iv) a time duration between each electrical pulse is about 0.1 seconds to about 10 seconds; and
  (v) each electrical pulse has a pulse width of about 10 us to about 10,000 us.

2. The method of claim 1, wherein the flowing the cells and the cargo into the electroporation chamber comprises pumping the cells and the cargo into the electroporation chamber at a designated interval of time, and wherein a flow rate of the cells and the cargo is about 0.1 ml/min to about 15 ml/min.

3. The method of claim 1, wherein the multiple electrical pulses are 2 pulses to 10 pulses.

4. The method of claim 1, wherein the electroporation medium has a conductivity of 1 mS/m to about 20 mS/m and an osmolarity of about 50 mOsm/l to about 300 mOsm/l.

5. The method of claim 1, wherein the electroporation medium comprises one or more of a salt, a monosaccharide and a buffering agent, wherein the salt is selected from the group consisting of a metal halide salt, a phosphate salt, a metal sulfate salt, and a combination thereof.

6. The method of claim 1, wherein the first input is present in the first electrode, the second electrode, or the fluid channel region, and the first output is present in the first electrode, the second electrode, or the fluid channel region.

7. The method of claim 1, wherein the first input and the first output are both present in the first electrode or the first input and the first output are both present in the second electrode.

8. The method of claim 1, wherein the electroporation chamber further comprises a first outer input further allowing the flowing of the cells and the cargo into the electroporation chamber and a first outer output further allowing passage of the electroporated cells from the electroporation chamber.

9. The method of claim 1, wherein the first electrode is bounded by a first material and the second electrode is bounded by a second material.

10. The method of claim 9, wherein a first outer input is present in the first material and a first outer output is present in the second material or the first outer input is present in the second material and the first outer output is present in the first material.

11. The method of claim 9, wherein a first outer input and a first outer output are both present in the first material or the first outer input and the first outer output are both present in the second material.

12. The method of claim 1, wherein a width of the electroporation chamber is about 0.01 mm to about 10 mm.

13. The method of claim 1, wherein the path is linear, curved, branched, or a combination thereof.

14. The method of claim 1, wherein the path is horizontal with respect to the first electrode and the second electrode.

15. The method of claim 14, wherein the cells within the electroporation chamber flow coplanar in the path along the length of the electroporation chamber.

16. The method of claim 1, wherein the first electrode and the second electrode are each a solid electrode or a mesh electrode.

17. The method of claim 1, wherein the first electrode, the second electrode, or both comprise a plurality of solid metal plates, wherein each solid metal plate is configured to apply an independent field strength.

18. The method of claim 1, wherein the cargo is a nucleic acid.

19. The method of claim 18, wherein the nucleic acid is an RNA or a DNA.

20. The method of claim 1, wherein the cargo is RNA and the electroporated cells are T cells with a viability of at least about 80% and an efficiency of at least about 90%.

21. The method of claim 1, wherein the cells are mammalian cells.

22. The method of claim 21, wherein the mammalian cells are selected from the group consisting of NK cells, EC-7 cells, T cells, CHO-S cells, dendritic cells, embryonic cells, stem cells, epithelial cells, lymphocytes, macrophages, gamete cells, and fibroblasts.

23. The method of claim 22, wherein the NK cells are haNK cells, primary NK cells, or activated NK cells; the T cells are CD4 and CD8 T cells; and the stem cells are AD-MSC cells.

24. The method of claim 1, wherein the cells are selected from the group consisting of NK cells, T cells, EC-7 cells, CHO-S cells, dendritic cells, and stem cells; and
wherein:
  (i) the field strength is applied at the voltage of about 20 V to about 50 V;
  (ii) the pulse width is about 20 us to about 700 us; and
  (iii) the cell density of the cells in the electroporation medium is about $5\times10^6$ cells/ml to about $300\times10^6$ cells/ml.

25. The method of claim 24, wherein the cargo is DNA and the electroporated cells are EC-7 cells with a viability of at least 70%.

26. The method of claim 24, wherein the cargo is DNA and the electroporated cells are CHO-S cells with a viability of at least about 70%.

27. The method of claim 24, wherein the cargo is RNA or DNA and the electroporated cells are NK cells with a viability of at least about 80% and an efficiency of at least about 80%.

28. The method of claim 24, wherein the cargo is RNA and the electroporated cells are dendritic cells with a viability of at least about 80% and an efficiency of at least about 80%.

29. The method of claim 24, wherein the cargo is DNA and the electroporated cells are stem cells with a viability of at least about 70% and an efficiency of at least about 80%.

30. The method of claim 22, wherein the mammalian cells are embryonic cells.

31. The method of claim 22, wherein the mammalian cells are stem cells.

32. The method of claim 22, wherein the mammalian cell are epithelial cells.

33. The method of claim 22, wherein the mammalian cells are lymphocytes.

34. The method of claim 22, wherein the mammalian cells are macrophages.

35. The method of claim 22, wherein the mammalian cells are gamete cells.

36. The method of claim 22, wherein the mammalian cells are fibroblasts.

37. The method of claim 31, wherein the stem cells are AD-MSC cells.

38. The method of claim 1, wherein the cells are bacteria cells or yeast cells.

* * * * *